United States Patent [19]

Krastinat

[11] 4,243,678
[45] Jan. 6, 1981

[54] ACYLHYDROCARBYLAMINOALKANOIC ACIDS, COMPOSITIONS AND USES

[75] Inventor: Walter Krastinat, Constance, Fed. Rep. of Germany

[73] Assignee: Byk Gulden Lomberg Chemische Fabrik GmbH, Constance, Fed. Rep. of Germany

[21] Appl. No.: 969,701

[22] Filed: Dec. 15, 1978

[30] Foreign Application Priority Data

Dec. 30, 1977 [LU] Luxembourg .............................. 78865
Jun. 14, 1978 [CH] Switzerland ........................... 6504/78
Jun. 14, 1978 [CH] Switzerland ........................... 6505/78

[51] Int. Cl.$^3$ .................... A01N 37/12; C07C 101/44; C07C 101/16; C07C 101/04
[52] U.S. Cl. ................................... 424/319; 562/561; 562/553; 424/309; 562/567; 562/454; 560/38; 562/433; 560/19; 560/39; 560/10; 560/9; 560/20; 560/21; 560/22; 560/43; 560/250; 560/251; 560/117; 560/118; 560/155; 560/170; 560/172; 562/443; 562/444; 562/448; 562/449; 562/453; 562/456; 562/457; 562/437; 562/435; 562/426; 562/427; 562/499; 562/500; 562/507; 562/556
[58] Field of Search ............... 562/453, 454, 457, 433, 562/443, 444, 448, 456; 424/319, 309; 560/19, 41, 43, 250, 251

[56] References Cited

U.S. PATENT DOCUMENTS

| | | | |
|---|---|---|---|
| 3,763,216 | 10/1973 | Bertrand .............................. | 562/455 |
| 3,780,095 | 12/1973 | Klamm et al. ...................... | 562/455 |
| 3,839,433 | 10/1974 | Wasley ................................ | 562/455 |
| 4,016,287 | 4/1977 | Eberhardt et al. .................. | 424/319 |
| 4,034,111 | 7/1977 | Schoetensack et al. ............ | 424/319 |
| 4,093,738 | 6/1978 | Hubele ............................... | 562/457 |

*Primary Examiner*—James H. Reamer
*Attorney, Agent, or Firm*—Berman, Aisenberg & Platt

[57] ABSTRACT

Compounds of the formula

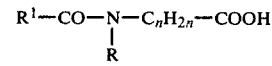

wherein
R is (a) optionally-substituted and optionally-hydrogenated biphenylyl, (b) optionally-substituted and optionally-hydrogenated bicyclic aryl having from 8 to 12 ring carbon atoms or (c) a radical of the formula

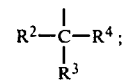

$R^1$ is aliphatic hydrocarbyl, alicyclic hydrocarbyl or optionally-substituted phenyl;
$R^2$ is —H or lower aliphatic hydrocarbyl;
$R^3$ is —H, lower alkyl, cycloalkyl, optionally-substituted phenyl or, with $R^4$, alkylene;
$R^4$ is lower alkyl, cycloalkyl, optionally-substituted phenyl, optionally-(nuclearly)-substituted phenalkyl or, with $R^3$, alkylene;
or $R^2$, $R^3$ and $R^4$, together with the carbon to which each is bound, are adamantyl; and
n is 3, 4 or 5;

and salts thereof with a base are pharmacologically active. Esters thereof are valuable intermediates for the preparation of the pharmacologically-active compounds. Physiologically-acceptable embodiments are administered, e.g., in the form of an appropriate pharmaceutical composition to warm-blooded animals for protection against and treatment for stomach, intestine, pancreas, bile and liver disorders. Syntheses of pharmacologically-active components, transforming toxic embodiments to physiologically-acceptable principles, compounding such principles into pharmaceutical compositions and using such principles for preventing and treating the noted disorders are discussed.

100 Claims, No Drawings

ACYLHYDROCARBYLAMINOALKANOIC ACIDS, COMPOSITIONS AND USES

BACKGROUND

Benzyl-[N-(lower alkyl)]-γ-aminobutyrates or (lower alkyl)-N-phenyl-γ-aminobutyrates are used for the treatment of gastric ulcers [JA-PS 38(63)-15368 or JA-PS 38(63)-7324]. N-(benzoyl or alkanoyl)-N-alkyl-γ-aminobutyric acid is claimed (U.S. Pat. No. 4,016,287) to be useful for inhibiting sebaceous gland excretion and combatting skin inflammation. N-(2-alkoxybenzoyl)aminoacids are said to possess an antipyretic and analgesic action (DT-OS No. 24 07 016). Trialkoxybenzoyl-aminoalkanoic acids possess great importance in the treatment of cardiopathies, for example cardiac infarct, cardiac ischaemia or cardiac arrhythmia (U.K. Pat. No. 1,275,189, U.K. Pat. No. 1,331,607, U.S. Pat. No. 3,743,550, U.S. Pat. No. 3,693,827, U.S. Pat. No. 3,726,913, U.S. Pat. No. 3,697,563 and U.S. Pat. No. 3,769,334). N-propionyl-ε-aminocaproic acid is used as an active principle for cosmetic preparations for the treatment of anomalies in the grain of the skin which are related to disorders in the formation of connective or fibrous tissue (U.K. Pat. No. 1,206,386). 4-[methylbenzoylamino]butyric acid and 6-[methylbenzoylamino]-hexanoic acid-(1) are described in Beilstein's "Handbuch der organischen Chemie", (EIII9, 1150 and 1158). A description of the production of 5-(N-methylacetamido)valeric acid is found in *J. Chem. Soc.* (London), C 1969, 1863. N-benzoyl-N-phenyl-α-amino acids are said to inhibit inflammation and to possess analgesic effects (DT-OS No. 17 68 173), whereas, during the investigation of N-benzoylanilinoalkanecarboxylic acids [D. Evans et al, *J. Med. Chem.*, 12 (1969) 1006–10], the corresponding butyric acids showed no inflammation inhibiting activity. U.S. Pat. No. 3,780,095 claims N-acyl-anilinoalkanoic acids with a choleretic effect and to which further activities are also attributed (U.S. Pat. No. 4,034,111). α-phenylbenzylidene-ω-aminoalkanoic acids and their derivatives are said to be used in agents which have an anti-epileptic effect (DT-OS No. 2 634 288). Naphthylaminoalkanoic acids and their esters are said to have a central-depressive and strongly-sedative action (DT-OS No. 1 543 802).

A new class of acylhydrocarbylaminoalkanoic acids, which is neither mentioned in nor rendered obvious by the aforesaid publications, has now been synthesized. It has also been found that these acylhydrocarbylaminoalkanoic acids possess interesting and particularly advantageous pharmacological properties.

SUMMARY OF THE INVENTION

The invention concerns A. pharmacologically-active compounds and particularly those (readily and conventionally prepared from other such compounds) which are physiologically acceptable, B. pharmaceutical compositions, an active principle of which is a physiologically-acceptable compound (A) and C. the use of a physiologically-acceptable compound (A) for protection against or treatment of a stomach, intestine, pancreas, bile or liver disorder. The active compounds (A) are:

1. Acids of the formula $$R^1-CO-N(R)-C_nH_{2n}-COOH \quad (I),$$

2. Salts of such acids with an organic or inorganic base.

Esters of such acids with an alkanol, a phenalkanol or a nuclearly-substituted phenalkanol are valuable intermediates. In each of these compounds n is 3, 4 or 5, and the amino nitrogen is separated by from 3 to 5 carbon atoms from the HOOC— group. The compounds are otherwise of the following types:

(a) R is adamantyl-(1)
 (i) $R^1$ is lower aliphatic hydrocarbyl,
 (ii) $R^1$ is alicyclic hydrocarbyl having from 3 to 10 ring carbon atoms,
 (iii) $R^1$ is phenyl, and
 (iv) $R^1$ is substituted phenyl;
(b) is

wherein
 $R^2$ is —H, lower alkyl, lower alkenyl or lower alkynyl;
 $R^3$ is —H, lower alkyl, cycloalkyl, phenyl, substituted phenyl or, together with $R^4$, alkylene;
 $R^4$ is lower alkyl, cycloalkyl, phenyl, substituted phenyl, phenalkyl, substituted phenalkyl or, together with $R^3$, alkylene;
 $R^4$ has at least 3 carbon atoms when $R^4$ is lower alkyl, $R^2$ is —H or methyl, $R^3$ is —H and $R^1$ is lower alkyl, phenyl or substituted phenyl; and
 $R^1$ is, independently, each of the meanings (i) through (iv) indicated under (a);

(c) R is biphenylyl, substituted biphenylyl, at least partially-hydrogenated biphenylyl or substituted (at least partially-hydrogenated)-biphenylyl [hereinafter referred to as (D-E) or represented as in formula Ic], and $R^1$ is, independently, each of the meanings of (i) through (iv) indicated under (a); and (d) R is bicyclic aryl (with from 8 to 12 ring carbon atoms and both rings of which have at least two carbon atoms in common), substituted bicyclic aryl, at least partially-hydrogenated bicyclic aryl or substituted (at least partially-hydrogenated)bicyclic aryl [hereinafter referred to as (FZG) or represented as in formula Id], and $R^1$ is, independently, each of the meanings of (i) through (iv) indicated under (a).

DEFINITIONS

Throughout the disclosure and claims all terms (unless otherwise defined) are accorded their ordinary and accepted meanings. A number of terms are hereinafter defined and are used throughout the text with the following definitions in the absence of a clear indication to the contrary.

acid binding agent (proton acceptor)—a substance that gains a hydrogen ion, a base, e.g. an alkali-metal hydroxide, such as sodium hydroxide and potassium hydroxide; an alkali-metal carbonate, such as sodium carbonate and potassium carbonate; or a tertiary amine, such as pyridine, triethylamine and ethyldiisopropylamine.

acyclic—aliphatic.

acyl—an acid radical, such as that formed by removing the —OH of a carboxylic acid [R—CO—OH] or of a carbonic acid [RO—CO—OH], wherein R is an organic residue such as aliphatic hydrocarbyl, alicyclic hydrocarbyl and optionally-substituted phenyl; includes radicals of mono- and polybasic carboxylic acids and of carbonic acid monoalkyl esters, in which the alkyl is preferably lower alkyl, e.g. propionyl and ethoxycarbonyl.

acyloxy—acyl-O, e.g. acetoxy, propionyloxy and butyryloxy.

adamantyl—adamantyl-(1)

alicyclic—cycloaliphatic; pertaining to a closed chain or ring of (substituted or unsubstituted, saturated or unsaturated) carbon atoms; the closed chain or ring has, e.g., from 3 to 10 (preferably 5 to 7 or 8) ring members, but is not so restricted, and any unsaturation is of aliphatic, rather than aromatic, character; alicyclic or cycloaliphatic hydrocarbon radicals include, e.g., cyclopropyl, cyclobutyl, cyclopentyl, cyclohexyl, cycloheptyl and their unsaturated analogues, such as 2-cyclopentenyl, 3-cyclohexenyl and 2,4-cyclohexadien-1-yl; particularly useful alicyclics are hydrocarbon radicals with from 3 to 10 ring carbon atoms, for example cyclopropyl, cyclobutyl, cyclopentyl, cyclohexyl, cycloheptyl or cyclooctyl, of which those with from 5 to 7 or 8 ring carbon atoms are preferred.

aliphatic hydrocarbon radical—hydrocarbyl that has an open chain of carbon atoms, whether normal or forked, saturated or unsaturated; it is preferably "lower" and ordinarily, monovalent, e.g. alkyl, alkenyl and alkynyl; unsaturation is either mono (as in allyl) or multiple (as in butadienyl), and multiple unsaturation can (but need not) be conjugated; includes straight-chain or branched alkyl radicals with, e.g., from 1 to 7 carbon atoms; straight-chain alkyl is, e.g., methyl, ethyl, propyl, butyl, pentyl, hexyl or heptyl, of which those with from 1 to 5, particularly those with from 1 to 3 (especially those with 1 or 2), carbon atoms are preferred; branched alkyl with, e.g., from 3 to 7 carbon atoms is, for example, isopropyl, isobutyl, sec.-butyl or tert.-butyl, of which those with from 3 to 5, carbon atoms are preferred; unsaturated aliphatic hydrocarbon radicals are, e.g., alkenyl and alkynyl with from 2 to 7 carbon atoms, for example ethenyl, ethynyl, 1-propenyl, 1,3-butadienyl and 2-butynyl, of which 1-propenyl and ethynyl are preferred.

alkali metal—a metal, such as lithium, sodium and potassium, in Group IA of the Periodic Table.

alkaline-earth metal—a metal, such as magnesium and calcium, in Group IIA of the Periodic Table.

alkanoic acid—saturated (preferably lower) hydrocarbyl aliphatic carboxylic acid, e.g. acetic acid, propionic acid and butyric acid.

alkanol—hydroxy-substituted, preferably monohydroxy-substituted, lower alkane, e.g. methanol, ethanol, isopropanol and butanol.

alkanoyl—acyl of an alkanoic acid; alkyl (ordinarily lower) carbonyl and preferably having from 2 to 5 carbon atoms, e.g. acetyl, propionyl and butyryl.

alkanoyloxy—alkanoyl-O-, e.g. acetoxy, propionyloxy and butyryloxy.

alkenyl—olefinically-unsaturated monovalent acyclic hydrocarbyl, such as ethenyl, 1-propenyl and 1,3-butadienyl, having, e.g., from 2 to 7 carbon atoms and no acetylenic unsaturation.

alkinyl—(cf. alkynyl).

alkoxy—alkyloxy; alkyl-O-; e.g. ethoxy and isopropoxy.

alkyl—saturated monovalent acyclic hydrocarbyl having, e.g., from 1 to 7 carbon atoms; either straight-chained, e.g. methyl, ethyl, propyl, butyl, pentyl, hexyl and heptyl, especially those with from 1 to 5, and preferably those with 1 or 2, carbon atoms, or branched (having from 3 to 7 carbon atoms), e.g. isopropyl, isobutyl, sec.-butyl and tert.-butyl, especially those with from 3 to 5 carbon atoms.

alkylene—saturated divalent acyclic hydrocarbyl having, e.g., from 2 to 8, preferably from 4 to 7, carbon atoms and having free valence bonds on different carbon atoms, e.g. tetramethylene and pentamethylene.

alkylmercapto—alkyl-S-, e.g. ethylmercapto and propylmercapto.

alkynyl (alkinyl)—acetylenically-unsaturated monovalent acyclic hydrocarbyl, such as ethynyl and 2-butynyl, having, e.g., from 2 to 7 carbon atoms and no olefinic unsaturation.

amine—a compound, such as ethylenediamine, dimethylamine, diethylamine, morpholine, piperidine, piperazine, N-(lower alkyl)piperazine (e.g. N-methylpiperazine), methylcyclohexylamine, benzylamine and quinoline, derived from ammonia by, e.g., replacing 1, 2 or all 3 hydrogen atoms by a corresponding number of independently-selected organic radicals.

amino—free amino, —$NH_2$. For substituted amino one or both hydrogen atoms are, independently, replaced by monovalent organic radicals; e.g. lower alkyl, such as methyl, ethyl and isopropyl; alternatively, both hydrogen atoms are replaced by a divalent organic radical, e.g. alkylene, such as pentamethylene.

aminoalkanol—alkanolamine; an organic compound having both an amino group and an alcohol group, such as ethanolamine, diethanolamine, triethanolamine, tris-(hydroxymethyl)-aminomethane, 2-amino-2-methylpropanol and 2-amino-2-methyl-1,3-propanediol.

amino sugar—amino-substituted sugar, such as glucamine, N-methylglucamine, glucosamine and N-methylglucosamine.

aryl—an optionally-substituted carbocyclic aromatic radical having from 6 to 12 ring carbon atoms.

base—a compound which is a proton acceptor; either inorganic, such as sodium hydroxide, or organic, such as diethylamine, morpholine and quinoline.

basic amino acid—an amino acid with basic properties, e.g. those with more than one amino group, such as lysine, ornithine and arginine.

bicyclic aryl—a monovalent optionally-substituted carbocyclic aromatic radical having two rings which have from 8 to 12 ring carbon atoms and at least two ring carbon atoms in common, e.g. α-naphthyl, β-naphthyl, 5-indanyl, 2-pentalenyl, 5-azulenyl and 3-heptalenyl; there is a marked preference for those embodiments having only two ring-carbon atoms in common.

biphenylyl—2-, 3- or 4-biphenylyl.

Chirality center—a center with respect to which an object and its mirror image are not superposable, e.g. an asymmetric carbon atom.

cycloalkyl—saturated carbocyclic (homocyclic) monovalent radical, e.g. cyclohexyl, having from 3 to 10, preferably from 5 to 8, ring carbon atoms in a single ring.

derivative—a compound or group of elements (radical) which is obtained from a different compound or radical, respectively, by a simple chemical process.

earth metal—a metal, such as aluminum, in Group III of the Periodic Table.

electrophilic radical—cf. definition of functional acid derivative.

enantiomer—one of a pair of optical isomers which are related to each other as an object and its nonsuperimposable mirror image.

forked—branch-chained; having a side chain of one or more carbon atoms, e.g. 2-ethyl-3-methylbutyl.

functional derivative—a derivative which contains a radical with a replaceable hydrogen atom.

functional acid derivative—a derivative with a functional group, A, which is convertible by solvolysis into the free carboxyl group; illustrative are those wherein A is —CN or —C(=X)—Y,
X is =O, =S, =NH or substituted imino, e.g. lower alkylimino and hydroxyimino (=NOH),
Y is hydroxy (—OH) or a monovalent eliminable electrophilic radical, especially a free or substituted amino group, preferably monoalkylamino, dialkylamino, arylamino, hydroxyamino, hydrazino, a hydrazobenzene group, β-hydroxyethylamino; mercapto (—SH); substituted mercapto, preferably lower alkylthio; substituted hydroxy, preferably lower alkoxy; azido; chloro; bromo; morpholino; or piperidino; Y is not —OH when X is =O.

[Alkyl of alkylimino, monoalkylamino, dialkylamino, alkylthio and alkoxy is preferably alkyl with from 1 to 5 or 6 carbon atoms; aryl of arylamino is carbocyclic aryl having from 6 to 10 ring carbon atoms in one or two rings.]

halo—a monovalent halogen atom, e.g. chloro, fluoro, bromo and iodo, particularly chloro, fluoro and bromo, especially chloro and fluoro, and preferably chloro.

hydrocarbon—a radical (hydrocarbyl) or compound composed entirely of hydrogen and carbon atoms; either saturated or unsaturated; either aliphatic, alicyclic or aromatic.

hydrocarbyl—a radical which consists of a hydrocarbon from which one hydrogen atom has been removed; a radical consisting solely of carbon and hydrogen atoms, e.g. ethyl, vinyl, cyclohexyl and naphthyl.

hydrogenated—as applied to biphenylyl and bicyclic aryl, from at least two to at most all of the unsaturated ring carbon atoms are saturated, as, e.g., in p-cyclohexylphenyl, 2-cyclohexylphenyl, 4-phenylcyclohexyl and 1,2,3,4-tetrahydronaphthyl-(1).

inorganic base—a base having, e.g., an alkali metal, an alkaline-earth metal or an earth metal as cation.

leaving group—a group which can be split off easily; for acyl derivates $R^1$—CO— (e.g. $R^{10}$)—comprises hydroxy (—OH); halo, e.g. chloro or bromo; lower alkylsulfonyloxy, such as mesyloxy; optionally-substituted benzenesulfonyloxy, such as p-tolylsulfonyloxy; lower alkoxy, preferably methoxy or ethoxy; lower alkylmercapto, such as methylmercapto and ethylmercapto; or acyloxy ($R^1$—CO—O) wherein $R^1$ is lower aliphatic hydrocarbyl (such as lower alkyl, e.g. methyl), alicyclic hydrocarbyl having from 3 to 10 ring carbon atoms (such as cycloalkyl, e.g. cyclohexyl), phenyl or substituted phenyl (such as p-chlorophenyl).

for

(e.g. $R^{12}$) comprises, e.g., halo, such as iodo and, preferably, chloro or bromo; and trihalomethyl, such as trichloromethyl and tribromomethyl.

lower—having at most 8 carbon atoms.

normal—straight-chained, e.g. n-propyl, n-butyl and n-hexyl.

nuclearly-substituted—substituted on a ring, as opposed to being substituted on a chain; nuclearly-substituted benzyl means that the benzene ring bears at least one substituent, e.g. p-chlorobenzyl.

optionally hydrogenated—partially or completely hydrogenated or not hydrogenated at all; one or more double bonds are optionally saturated [e.g., 1-(1,4-dihydro)-naphthyl, 1-(1,2,3,4-tetrahydro)naphthyl, 2-(1,2,5,6-tetrahydro)naphthyl, 7-(1,4-dihydro)naphthyl, 1-perhydronaphthyl and 2-perhydronaphthyl]; when double bonds are present in more than one ring, such as in biphenylyl, one or more double bonds are removed from either ring [e.g., 2-(1,4-dihydro)biphenylyl, 4-phenylcyclohexyl and o-cyclohexylphenyl], from both rings [e.g., 4-cyclohexylcyclohexyl] or from neither ring [e.g., 2-biphenylyl]; for bicyclic aryl and for biphenylyl "optionally hydrogenated" includes, but is preferably less than, complete saturation.

optionally-substituted amino—unsubstituted amino, —$NH_2$, or such amino wherein one (monosubstituted) hydrogen atom is or both (disubstituted) hydrogen atoms are, independently, replaced, e.g., by alkyl having from 1 to 4, preferably 1 or 2, carbon atoms (e.g. ethylamino, dimethylamino and N-ethyl-N-methylamino), or by an acyl, such as alkanoyl with from 2 to 5 carbon atoms (e.g. acetylamino, propionylamino and N-acetyl-N-ethylamino), usually employed as an amino-protective group.

optionally-substituted phenyl—substituted or unsubstituted phenyl, particularly that of the formula

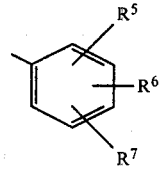

in which each of $R^5$, $R^6$ and $R^7$ is, independently, a hydrogen atom (—H), alkyl, such as those with from 1 to 4 (preferably 1 to 3 and especially 1) carbon atoms, e.g. methyl, ethyl and isopropyl; hydroxy (—OH); alkoxy, such as those with from 1 to 4 (preferably 1 to 3 and especially 1) carbon atoms, e.g. methoxy, ethoxy and isopropoxy; alkylmercapto, such as those with from 1 to 4 carbon atoms, e.g. methylmercapto, ethylmercapto and isopropylmercapto; halo, such as fluoro, chloro or bromo, particularly fluoro or chloro and, preferably, chloro; acyloxy, advantageously carboxylic acid acyloxy, inter alia that of the formula $R^1$—CO—O— wherein $R^1$ is aliphatic hydrocarbyl, alicyclic hydrocarbyl or optionally-substituted phenyl, particularly alkanoyloxy with from 2 to 7 carbon atoms, especially those with from 2 to 5 carbon atoms and, preferably, acetoxy; optionally-substituted amino, which is unsubstituted amino, —NH$_2$, or such amino wherein one (monosubstituted) hydrogen atom is or both (disubstituted) hydrogen atoms are, independently, replaced, e.g., by alkyl having from 1 to 4, preferably 1 or 2, carbon atoms (e.g. ethylamino, dimethylamino and N-ethyl-N-methylamino), or by an acyl, such as alkanoyl with from 2 to 5 carbon atoms (e.g. acetylamino, propionylamino and N-acetyl-N-ethylamino), usually employed as an amino-protective group; nitro (—NO$_2$); trifluoromethyl (—CF$_3$); trifluoromethoxy (—O—CF$_3$); or trifluoromethylmercapto (—S—CF$_3$).

optionally-substituted phenalkyl—unsubstituted phenalkyl wherein the alkyl has from 1 to 4 (preferably 1) carbon atoms, e.g. phenethyl, phenylpropyl and, preferably, benzyl, and such phenalkyl, e.g. "optionally-substituted phenyl" alkyl, which is nuclearly substituted (preferably monosubstituted or disubstituted) by one or more independently-selected substituents, preferably halo, e.g. chloro (p-chlorobenzyl or m-chlorobenzyl), fluoro (o-fluorobenzyl or p-fluorobenzyl) and bromo (p-bromobenzyl), lower alkyl, e.g. methyl (p-methylbenzyl), and lower alkoxy, e.g. methoxy (p-methoxybenzyl or 3,4-dimethoxybenzyl); the substituents are, optionally, in any number, combination and position possible on the phenyl ring.

organic base—a base, such as an organic nitrogen base, which is able to accept a proton.

organic nitrogen base—an organic nitrogen compound, which is able to accept a proton, e.g. an amine, an aminoalkanol, an amino sugar or a basic amino acid.

phenalkanol—hydroxy(lower)alkylbenzene, preferably monohydroxy(lower)alkylbenzene; substituted phenalkanols are limited to substitution on the benzene nucleus.

phenalkyl—(cf. phenylalkyl)

phenylalkyl (phenalkyl)—phenyl-substituted alkyl, the alkyl of which has from 1 to 4 carbon atoms, e.g. phenethyl, phenylpropyl and, preferably, benzyl.

protective group— for —COOH (cf. A) comprises a salt form (—COOM) with an inorganic or with an organic base (M), such salt being, e.g., an alkali-metal salt, such as a sodium or potassium salt; an alkaline-earth-metal salt, such as a calcium or magnesium salt; an ammonium salt; a salt form with a tertiary base, such as triethylamine and pyridine; a quaternary ammonium salt; an ester form with an alkanol, such as a methyl, propyl or butyl ester; or an ester form with a phenalkanol, such as a benzyl or phenethyl ester.

racemate—an optically inactive mixture of one or more pairs of enantiomers.

room temperature—20° C.

salt—pharmacologically-incompatible salt or, preferably, pharmacologically—, that is, biologically—, tolerated salt, the former being conventionally convertible into the latter; the salt cation is inorganic, e.g. an alkali metal, an alkaline-earth metal or an earth metal, or organic, such as that of a nitrogen base, e.g. an amine, an aminoalkanol, an amino sugar or a basic amino acid.

substituent—an atom or radical which is made part of a molecule by replacing another atom or radical.

substituted—a derivative; a molecular structure bearing one or more substituents; any substituent on a ring carbon atom is halo, lower alkyl, lower alkenyl, lower alkynyl, lower alkoxy, lower alkylmercapto, hydroxy (—OH), benzoyloxy, lower aliphatic hydrocarbyl carbonyloxy, alicyclic hydrocarbyl carbonyloxy having from 3 to 10 ring carbon atoms, amino (—NH$_2$), monosubstituted amino, disubstituted amino, nitro (—NO$_2$), trifluoromethyl (—CF$_3$), trifluoromethoxy (—OCF$_3$) or trifluoromethylmercapto (—SCF$_3$); any substituent of monosubstituted amino or of disubstituted amino is, independently, lower alkyl or alkanoyl.

DETAILS

The invention primarily concerns acylhydrocarbyl-($\gamma$-, $\Delta$- and $\epsilon$-)aminoalkanoic acids of the formulae:

(Ia)

(Ib)

(Ic)

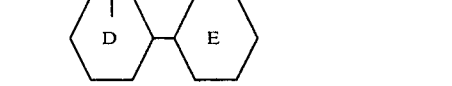
(Id)

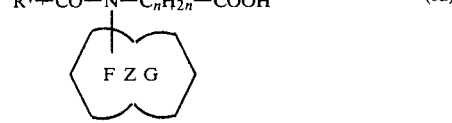

wherein
each of rings D, E and F is an aromatic carbocyclic ring or an at-least-partially hydrogenated counterpart thereof; each is unsubstituted or substituted by one or more substituents;

ring G is a completely unsaturated, partially unsaturated or completely saturated carbocyclic ring having at least two ring carbon atoms, Z, in common with ring F; it is unsubstituted or substituted by one or more substituents; and Z represents at least 2 (e.g., from 2 to 5), preferably 2, carbon atoms which are concurrently ring members of both ring F and ring G;

and their corresponding salts (preferably pharmacologically acceptable) with a base (either organic or inorganic).

In formulae Ia, Ib, Ic and Id:

$R^1$ is an aliphatic hydrocarbon radical, an alicyclic hydrocarbon radical, phenyl or substituted phenyl (the number and positions of substituents of any substituted phenyl in claimed compounds are limited only by practical considerations and do not, per se, constitute a critical aspect of the subject invention; however, phenyl rings with three or less substituents are preferred);

$R^2$ is a hydrogen atom (—H), lower alkyl, lower alkenyl or lower alkynyl;

$R^3$ is a hydrogen atom (—H), lower alkyl, cycloalkyl having from 3 to 10 ring carbon atoms, phenyl, substituted phenyl or, together with $R^4$, alkylene having from 2 to 8 carbon atoms;

$R^4$ is lower alkyl, cycloalkyl having from 3 to 10 carbon atoms, phenyl, substituted phenyl, phen(lower)alkyl, nuclearly-substituted phen(lower)alkyl or, together with $R^3$, alkylene having from 2 to 8 carbon atoms; $R^4$ has at least 3 carbon atoms when $R^4$ is lower alkyl, $R^2$ is —H or methyl, $R^3$ is —H and $R^1$ is lower alkyl, phenyl or substituted phenyl; and n is 3, 4 or 5.

Exemplary biphenylyl radicals (D-E) are, e.g., 2-, 3- and 4-biphenylyl radicals. Partially-hydrogenated biphenylyl radicals are, for example, 4-cyclohexylphenyl, 4-phenylcyclohexyl and 2-cyclohexylphenyl. Particularly-suitable substituents thereon are halo, for example fluoro, chloro or bromo, preferably chloro; alkyl with from 1 to 4 carbon atoms, preferably methyl; alkoxy with from 1 to 4 carbon atoms, preferably methoxy; optionally-substituted amino; hydroxy; or nitro.

Illustrative bicyclic aryl radicals with from 8 to 12 ring carbon atoms (FZG) are, for example, those which are derived from pentalene, indene, naphthalene, azulene, heptalene, biphenylene. Hydrogenated bicyclic aryl radicals are, e.g., dihydro, tetrahydro or hexahydro derivatives thereof, such as 1,4-dihydronaphthalene-(1) or -(2), 1,2,3,4-tetrahydronaphthalene-(1), indane-(5), 6,7,8,9-tetrahydro-5H-benzocycloheptene-(3) and 4,5,6,7,8,9-hexahydro-1H-cyclopentacyclooctene-(4). The bicyclic aryl radicals optionally have single or multiple substitution, in which case the substituents are, e.g., halogen atoms, for example fluoro or chloro; alkyl with from 1 to 4 carbon atoms; alkoxy with 1 to 4 carbon atoms; optionally-substituted amino; hydroxy or nitro groups. When calculating the number of carbon atoms of the aryl radical, no account is taken of the carbon atoms of the substituents.

Contemplated salts include salts of inorganic and organic bases. Pharmacologically-incompatible salts are converted by known methods into pharmacologically—, that is to say biologically—, tolerated salts, which are preferred. Illustrative cations for salt formation are, e.g., alkali metals, alkaline-earth metals or earth metals, but corresponding cations of organic nitrogen bases, such as amines, aminoalkanols, amino sugars or basic amino acids, are similarly useful.

Exemplary salts are those of lithium, sodium, potassium, magnesium, calcium, aluminum, ethylenediamine, dimethylamine, diethylamine, morpholine, piperidine, piperazine, N-(lower alkyl)piperazine (e.g. N-methylpiperazine), methylcyclohexylamine, benzylamine, ethanolamine, diethanolamine, triethanolamine, tris-(hydroxymethyl)-aminomethane, 2-amino-2-methyl-propanol, 2-amino-2-methyl-1,3-propandiol, glucamine, N-methylglucamine, glucosamine, N-methylglucosamine, lysine, ornithine, arginine and quinoline.

Particular embodiments (Ia* or Ib*) of the invention consist of acylhydrocarbyl-aminoalkanoic acids of formulae Ia and Ib, in which $R^1$ signifies aliphatic hydrocarbyl with from 1 to 5 carbon atoms, alicyclic hydrocarbyl with from 5 to 7 ring carbon atoms or optionally-substituted phenyl,

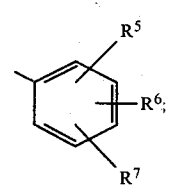

$R^2$ signifies a hydrogen atom (—H), alkyl with from 1 to 5 carbon atoms, alkenyl with from 2 to 5 carbon atoms, or alkynyl with from 2 to 5 carbon atoms;

$R^3$ signifies a hydrogen atom (—H) or alkyl with from 1 to 5 carbon atoms;

$R^4$ signifies alkyl with from 1 to 5 carbon atoms and with at least 3 carbon atoms when $R^2$ is —H or methyl and $R^3$ is —H, n signifies 3, 4 or 5;

$R^5$, $R^6$ and $R^7$ are the same or different; each is a hydrogen atom (—H), halo, alkyl with from 1 to 4 carbon atoms, alkoxy with from 1 to 4 carbon atoms, alkanoyloxy with from 2 to 5 carbon atoms, optionally-substituted amino, nitro, hydroxy or trifluoromethyl;

and their salts with an inorganic or organic base.

Preferred representatives of embodiments Ia* and Ib* are those in which $R^1$ signifies an aliphatic hydrocarbon radical with from 1 to 5 carbon atoms or a phenyl radical which is optionally substituted with $R^5$, $R^6$ and/or $R^7$; $R^2$ signifies a hydrogen atom (—H), alkyl with from 1 to 4 carbon atoms or ethynyl; $R^3$ signifies a hydrogen atom (—H) or alkyl with from 1 to 3 carbon atoms; $R^4$ signifies alkyl with from 1 to 5 carbon atoms and with at least 3 carbon atoms when $R^2$ is —H or methyl and $R^3$ is —H; n signifies 3, 4 or 5; $R^5$ signifies a hydrogen atom (—H); $R^6$ and $R^7$ are the same or different, each being a hydrogen atom (—H), halo, methyl, methoxy, optionally-substituted amino or trifluoromethyl; and their salts with an inorganic or organic base.

Particularly preferred representatives of embodiment Ia* and Ib* are those in which $R^1$ signifies an aliphatic hydrocarbon radical with from 1 to 5 carbon atoms or a phenyl radical substituted with $R^5$, $R^6$and/or $R^7$; $R^2$ signifies a hydrogen atom (—H), methyl or ethynyl; $R^3$ signifies a hydrogen atom (—H) or methyl; $R^4$ signifies alkyl with from 1 to 5 carbon atoms and with at least 3 carbon atoms when $R^2$ is —H or methyl and $R^3$ is —H; $R^5$ signifies a hydrogen atom (—H); $R^6$ signifies a hydrogen atom (—H), chloro, methoxy or trifluoromethyl; $R^7$ signifies a hydrogen atom (—H), chloro or methoxy; n signifies 4, 5 or, preferably, 3; and their salts with an inorganic or organic base.

Other embodiments (Ia and Ib) of the invention consist of acylhydrocarbylaminoalkanoic acids of formulae Ia and Ib, in which $R^1$ signifies aliphatic hydrocarbyl with from 1 to 5 carbon atoms, alicyclic hydrocarbyl with from 5 to 7 ring carbon atoms or a phenyl radical,

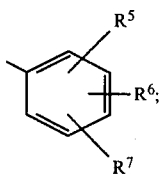

$R^2$ signifies a hydrogen atom (—H), alkyl with from 1 to 5 carbon atoms, alkenyl with from 2 to 5 carbon atoms, or alkynyl with from 2 to 5 carbon atoms;

$R^3$ signifies a hydrogen atom (—H), alkyl with from 1 to 5 carbon atoms, or cycloalkyl with from 5 to 7 ring carbon atoms;

$R^4$ signifies cycloalkyl with from 5 to 7 ring carbon atoms or $R^3$ and $R^4$, together, form an alkylene group, —$(CH_2)_q$, n signifies 3, 4 or 5, q signifies 4, 5, 6 or 7, and $R^5$, $R^6$ and $R^7$ are the same or different, each signifying a hydrogen atom (—H), halo, alkyl with from 1 to 4 carbon atoms, alkoxy with from 1 to 4 carbon atoms, alkanoyloxy with from 2 to 5 carbon atoms, optionally-substituted amino, nitro, hydroxy or trifluoromethyl;

and their salts with an inorganic or organic base.

Preferred representatives of embodiments Ia and Ib are those in which $R^1$ signifies an aliphatic hydrocarbon radical with from 1 to 5 carbo atoms or a phenyl radical substituted with $R^5$, $R^6$ and/or $R^7$; $R^2$ signifies a hydrogen atom (—H), alkyl with from 1 to 4 carbon atoms or ethynyl; $R^3$ signifies a hydrogen atom (—H), methyl or cyclohexyl; $R^4$ signifies cyclohexyl; or $R^3$ and $R^4$ together form an alkylene group, —$(CH_2)_q$; n signifies 3, 4 or 5; q signifies 4, 5, 6 or 7; $R^5$ signifies a hydrogen atom (—H); $R^6$ and $R^7$ are the same or different, each signfiying a hydrogen atom (—H), methyl, methoxy, optionally-substituted amino or trifluoromethyl; and their salts with an inorganic or organic bases.

Particularly preferred representatives of embodiments Ia and Ib are those in which $R^1$ signifies an aliphatic hydrocarbon radical with from 1 to 5 carbon atoms or a phenyl radical substituted with $R^5$, $R^6$ and/or $R^7$; $R^2$ signifies a hydrogen atom (—H), methyl or ethynyl; $R^3$ and $R^4$, together, form an alkylene group, —$(CH_2)_q$—; n signifies 4, 5 or, preferably, 3; q signifies 5 or 7; $R^5$ signifies a hydrogen atom (—H); $R^6$ signifies a hydrogen atom (—H), chloro, methoxy or trifluoromethyl; $R^7$ signifies a hydrogen atom (—H), chloro or methoxy; and their salts with an inorganic or organic base.

A further embodiment (Ib***) of the invention consists of acylhydrocarbylaminoalkanoic acids of formula Ib in which $R^1$ signifies an aliphatic hydrocarbon radical with from 1 to 5 carbon atoms, an alicyclic hydrocarbon radical with from 5 to 7 ring carbon atoms or optionally-substituted phenyl,

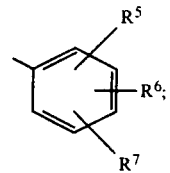

$R^2$ signifies a hydrogen atom (—H) or alkyl with from 1 to 5 carbon atoms;

$R^3$ signifies a hydrogen atom (—H), alkyl with from 1 to 5 carbon atoms or optionally-substituted phenyl,

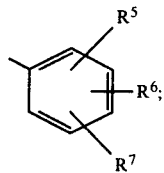

$R^4$ signifies optionally-substituted phenyl,

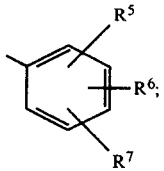

or optionally-substituted phenalkyl,

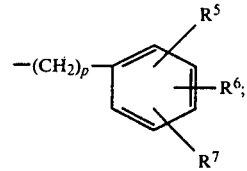

n signifies 3, 4 or 5;

p signifies 1, 2, 3 or 4;

$R^5$, $R^6$ and $R^7$ are the same or different, each signifying a hydrogen atom (—H), halo, alkyl with from 1 to 4 carbon atoms, alkoxy with from 1 to 4 carbon atoms, alkanoyloxy with from 2 to 5 carbon atoms, optionally-substituted amino, nitro, hydroxy or trifluoromethyl;

and their salts with an inorganic or organic base.

Preferred representatives of embodiment Ib*** are those in which $R^1$ signifies an aliphatic hydrocarbon radical with from 1 to 5 carbon atoms, or a phenyl radical substituted with $R^5$, $R^6$ and/or $R^7$; $R^2$ signifies a hydrogen atom (—H) or alkyl with from 1 to 4 carbon atoms; $R^3$ signifies a hydrogen atom (—H), alkyl with from 1 to 3 carbon atoms or a phenyl radical substituted with $R^7$; $R^4$ signifies a phenyl radical substituted with $R^7$ or a benzyl radical substituted with $R^7$; $R^5$ signifies a hydrogen atom (—H); $R^6$ and $R^7$ are the same or different, each signifying a hydrogen atom (—H), halo, methyl, methoxy, optionally-substituted amino or trifluoromethyl; and n signifies 3, 4 or 5;

and their salts with an inorganic or organic base.

Particularly preferred representatives of embodiment Ib*** are those in which $R^1$ signifies an aliphatic hydrocarbon radical with from 1 to 5 carbon atoms or a phenyl radical substituted with $R^5$, $R^6$ and/or $R^7$; $R^2$ signifies a hydrogen atom (—H); $R^3$ signifies a hydrogen atom (—H), methyl, or a phenyl radical substituted with $R^7$; $R^4$ signifies a phenyl radical substituted with $R^7$ or a benzyl radical substituted with $R^7$; $R^5$ signifies a hydrogen atom (—H); $R^6$ signifies a hydrogen atom (—H), chloro, methoxy or trifluoromethyl; $R^7$ signifies a hydrogen atom (—H), chloro or methoxy; n signifies 4, 5 or, preferably, 3;
and their salts with an inorganic or organic base.

Alternative embodiments (Ib****) of the invention consist of acylhydrocarbylaminoalkanoic acids of formula Ib, in which $R^1$ signifies aliphatic hydrocarbyl with from 1 to 5 carbon atoms, alicyclic hydrocarbyl with from 5 to 7 ring carbon atoms or optionally-substituted phenyl,

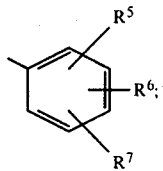

$R^2$ signifies alkenyl with from 2 to 5 carbon atoms or alkynyl with from 2 to 5 carbon atoms;
$R^3$ signifies a hydrogen atom (—H) or alkyl with from 1 to 5 carbon atoms;
$R^4$ signifies optionally-substituted phenyl,

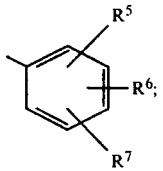

or optionally-substituted phenalkyl,

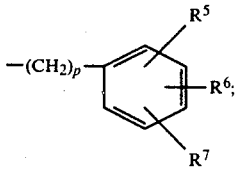

n signifies 3, 4 or 5;
p signifies 1, 2, 3 or 4;
$R^5$, $R^6$ and $R^7$ are the same or different, each signifying a hydrogen atom (—H), halo, alkyl with from 1 to 4 carbon atoms, alkoxy with from 1 to 4 carbon atoms, alkanoyloxy with from 2 to 5 carbon atoms, optionally-substituted amino, nitro, hydroxy or trifluoromethyl;
and their salts with an inorganic or organic base.

Preferred representatives of embodiment Ib**** are those in which $R^1$ signifies an aliphatic hydrocarbon radical with from 1 to 5 carbon atoms or a phenyl radical substituted with $R^5$, $R^6$ and/or $R^7$; $R^2$ signifies ethynyl; $R^3$ signifies a hydrogen atom (—H) or alkyl with from 1 to 3 carbon atoms; $R^4$ signifies a phenyl radical substituted with $R^7$ or a benzyl radical substituted with $R^7$; $R^5$ signifies a hydrogen atom (—H); $R^6$ and $R^7$ are the same or different, each signifying a hydrogen atom (—H), halo, methyl, methoxy, optionally-substituted amino or trifluoromethyl; and n signifies 3, 4 or 5; and their salts with an inorganic or organic base.

Particularly preferred representatives of embodiment Ib**** are those in which $R^1$ signifies an aliphatic hydrocarbon radical with from 1 to 5 carbon atoms or a phenyl radical substituted with $R^5$, $R^6$ and/or $R^7$; $R^2$ signifies ethynyl; $R^3$ signifies a hydrogen atom (—H) or methyl; $R^4$ signifies a phenyl radical substituted with $R^7$ or a benzyl radical substituted with $R^7$; $R^5$ signifies a hydrogen atom (—H); $R^6$ signifies a hydrogen atom (—H), chloro, methoxy or trifluoromethyl; $R^7$ signifies a hydrogen atom (—H), chloro or methoxy; n signifies 4, 5 or, preferably, 3; and their salts with an inorganic or organic base.

The embodiment Ib*** is preferred to the other embodiments. The embodiments Ia*, Ib*, Ia and Ib are preferred to the embodiment Ib****.

Illustrative compounds of formulae Ia and Ib are:
N-(2,6-dimethylbenzoyl)-4-[3-ethyl-1-pentyn-3-yl)amino]butyric acid,
N-(3,4-dichlorobenzoyl)-5-[(1-ethynylcyclohexyl-1)amino]-valeric acid,
N-(3-chloro-4-fluorobenzoyl)-4-[{1-(n-butyl)cyclopentyl-1}-amino]butyric acid,
N-isobutyryl-4-(tert.-butylamino)butyric acid,
N-propionyl-6[2-(3,4-dimethoxyphenyl)ethylamino]caproic acid,
N-(n-hexanoyl)-4-[adamantyl-(1)-amino]butyric acid,
N-(n-heptanoyl)-4-(n-butylamino)butyric acid,
N-crotonoyl-4-[(1-propylcyclohexyl-1)-amino]butyric acid,
N-(3-nitrobenzoyl)-4-[(4-chlorobenzyl)amino]butyric acid,
N-(2-acetoxybenzoyl)-4-[(1,1,3,3-tetramethylbutyl)amino]-butyric acid,
N-(2-bromobenzoyl)-4-[(3-ethyl-1-pentyn-3-yl)amino]-valeric acid,
N-(3-chlorobenzoyl)-4-[(1-ethynylcyclohexyl-1)-amino]butyric acid,
N-(cyclohexylcarbonyl)-4-[{1-(n-butyl)cyclopentyl-1}-amino]-caproic acid,
N-(2-chlorobenzoyl)-4-[(1-propylcyclohexyl-1)-amino]-butyric acid,
N-(2-fluorobenzoyl)-4-[(α-methylbenzyl)amino]butyric acid,
N-(3-nitrobenzoyl)-4-[(1,2-diphenylethyl)amino]butyric acid,
N-(4-nitrobenzoyl)-4-[(3,4-dimethoxybenzyl)amino]-butyric acid,
N-(3-trifluoromethylbenzoyl)-6-[(α-methylbenzyl)amino]caproic acid,
N-(3-toluoyl)-4-[benzhydrylamino]butyric acid,
N-isovaleroyl-5-[(α-methylbenzyl)amino]valeric acid.

Preferred compounds of this aspect of the invention are:
N-(p-chlorobenzoyl)-4-(1-phenylethylamino)butyric acid,
N-acetyl-4-benzhydrylaminobutyric acid,
N-(p-chlorobenzoyl)-4-benzhydrylaminobutyric acid,
N-(p-chlorobenzoyl)-4-benzylaminobutyric acid, and their salts with a base.

The acylhydrocarbylaminoalkanoic acids of formula Ib possess, on the carbon atom to which $R^2$, $R^3$ and $R^4$ are bound, a chirality center when $R^2$, $R^3$ and $R^4$ are different from one another. The invention includes the racemates, the individual enantiomers and their mixtures.

The compounds of formulae Ia and Ib possess valuable pharmacological properties which render them commercially useful. In warm-blooded animals they develop a stomach and liver protective action; in addition they bring about an increase in pancreas and liver (bile) secretion.

Because of their advantageous pharmacological activity the acylhydrocarbylaminoalkanoic acids of formulae Ia and Ib are suitable for the treatment (alleviating and reducing symptoms) and prohylaxis of diseases (which are attributable to stomach or intestine disorders or to reduced performance of the pancreas, the gall bladder and/or the liver), e.g. for treating gastric or intestinal ulcers, Billroth II, pancreatic insufficiently, sprue, indigestion and malabsorption of different aetiology, acute and chronic pancreatitis, indirect disturbances of the pancreatic function (supporting the secretin and pancreozymine production), as well as gall bladder and gall duct inflammation, disturbances in the flow of bile, motility disturbances of the gall ducts, a feeling of repletion, flatulence, constipation, upper abdominal complaint, hepato-biliary functional disorders, acute and chronic hepatitis, liver intoxication and fatty liver.

A further object of the invention is to provide pharmaceutical products which contain as active ingredient one or more physiologically-acceptable acylhydrocarbylaminoalkanoic acids of formulae Ia and/or of formula Ib, in which $R^1$ signifies aliphatic hydrocarbyl, alicyclic hydrocarbyl or optionally-substituted phenyl;

$R^2$ signifies a hydrogen atom (—H), alkyl, alkenyl or alkynyl;

$R^3$ signifies a hydrogen atom (—H), alkyl, cycloalkyl or optionally-substituted phenyl;

$R^4$ signifies alkyl, cycloalkyl, optionally-substituted phenyl or optionally-substituted phenylalkyl;

$R^4$ has at least 3 carbon atoms when $R^4$ is lower alkyl, $R^2$ is —H or methyl, $R^3$ is —H and $R^1$ is lower alkyl, phenyl or substituted phenyl, or $R^3$ and $R^4$ together signify alkylene, and n signifies 3, 4 or 5;

and/or their pharmacologically-compatible salts with an organic or inorganic base.

A further group of compounds (Ic*) of the invention comprises acylbiphenylylaminoalkanoic acids of formula Ic, in which $R^1$ signifies an aliphatic hydrocarbon radical with from 1 to 7 carbon atoms, an alicyclic hydrocarbon radical with from 3 to 10 ring carbon atoms or optionally-substituted phenyl,

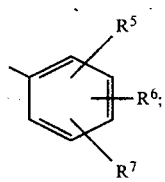

(D-E) signifies a group of the formula

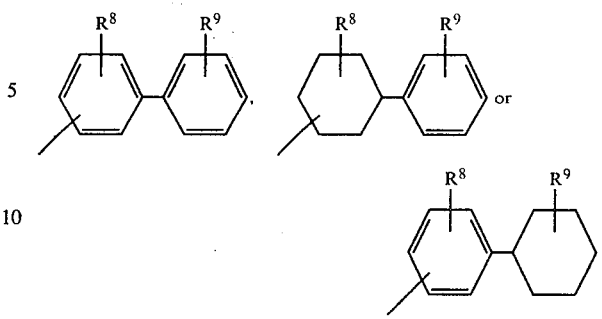

n signifies 3, 4 or 5;

$R^5$, $R^6$ and $R^7$ are the same or different and signify a hydrogen atom (—H), hydroxy (—OH), alkyl with from 1 to 4 carbon atoms, alkoxy with from 1 to 4 carbon atoms, alkanoyloxy with from 2 to 5 carbon atoms, nitro (—NO$_2$), halo or trifluoromethyl (—CF$_3$);

$R^8$ and $R^9$ are the same or different and signify a hydrogen atom (—H), halo, methyl (—CH$_3$), methoxy (—OCH$_3$), hydroxy (—OH) or nitro (—NO$_2$); and their salts (particularly pharmacologically-acceptable salts) with an inorganic or organic base.

Another group of compounds (Ic**) of the invention comprises acylbiphenylylaminoalkanoic acids of formula Ic, in which $R^1$ signifies an aliphatic hydrocarbon radical with from 1 to 5 carbon atoms, an alicyclic hydrocarbon radical with from 5 to 7 ring carbon atoms or optionally-substituted phenyl,

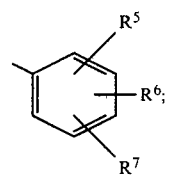

(D-E) signifies a group of the formula

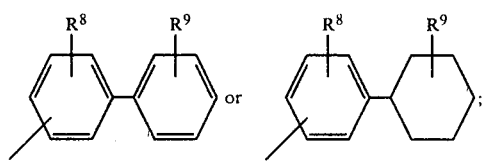

n signifies 3, 4 or 5;

$R^5$ signifies a hydrogen atom (—H);

$R^6$ and $R^7$ are the same or different and signify a hydrogen atom (—H), halo, hydroxy (—OH), methoxy, methyl, alkanoyloxy with from 2 to 5 carbon atoms, nitro or trifluoromethyl;

one of $R^8$ and $R^9$ signifies a hydrogen atom (—H); and the other signifies a hydrogen atom (—H), halo, methyl, methoxy, hydroxy or nitro;

and their salts (particularly pharmacologically-acceptable salts) with an inorganic or organic base.

A further group of compounds (Ic***) of the invention comprises acylbiphenylylaminoalkanoic acids of formula Ic, in which $R^1$ signifies an aliphatic hydrocarbon radical with from 1 to 3 carbon atoms or optionally-substituted phenyl,

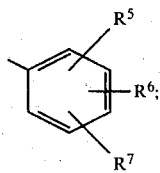

(D-E) signifies a group of the formula

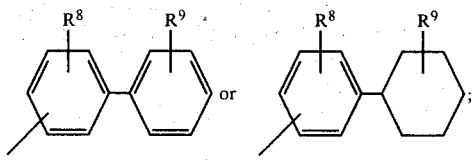

n signifies 3, 4 or 5;

$R^5$ signifies a hydrogen atom (—H);

$R^6$ and $R^7$ are the same or different and signify a hydrogen atom (—H), fluoro, chloro, hydroxy, methyl, methoxy, or trifluoromethyl, one of $R^8$ or $R^9$ signifies a hydrogen atom (—H); and the other signifies a hydrogen atom (—H), chloro or methoxy;

and their salts (particularly pharmacologically-acceptable salts) with an inorganic or organic base.

A preferred group of compounds (Ic****) of the invention comprises acylbiophenylylaminoalkanoic acids of formula Ic,
in which $R^1$ signifies an alkyl group with from 1 to 3 carbon atoms, alkenyl with 2 or 3 carbon atoms or optionally-substituted phenyl,

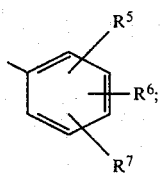

(D-E) signifies a group of the formula

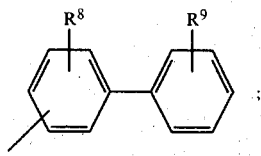

n signifies 3, 4 or 5;

$R^5$ signifies a hydrogen atom (—H);

$R^6$ signifies a hydrogen atom (—H), fluoro, chloro, hydroxy, methoxy or trifluoromethyl;

$R^7$ signifies a hydrogen atom (—H) or chloro;

one of $R^8$ and $R^9$ signifies a hydrogen atom (—H); and the other signifies a hydrogen atom (—H) or methoxy; and their pharmacologically-compatible salts with an inorganic or organic base.

Particularly preferred representatives of embodiments Ic* and Ic are those in which n is 3 or 5, and their pharmacologically-compatible salts with an inorganic or organic base. Further especially preferred representatives of embodiments Ic* and Ic**** are those in which (D-E) is a 2-biphenylyl radical, and their pharmacologically-compatible salts with an inorganic or organic base.

Illustrative compounds of formula Ic are:
4-[p-methoxy-N-(2'-fluorobiphenyl-2-yl)benzamido]-butyric acid,
4-[2,4-dichloro-N-(6-methylbiphenyl-2-yl)benzamido]-butyric acid,
4-[N-(2'-ethylbiphenyl-2-yl)-n-butyramido]butyric acid,
4-[3-fluoro-4-methyl-N-(3,2'-dimethylbiphenyl-2-yl)benzamido]-butyric acid,
4-[3,5-dimethoxy-N-(4-chlorobiphenyl-3-yl)benzamido]butyric acid,
4-[N-(4,4'-dimethylbiphenyl-3-yl)hexanoylamido]-butyric acid,
4-[m-trifluoromethyl-N-(6-ethoxybiphenyl-3-yl)benzamido]-butyric acid,
4-[o-bromo-N-(2'-methoxybiphenyl-4-yl)benzamido]-butyric acid,
4-[3-methoxy-4-methyl-N-(4'-methoxybiphenyl-4-yl)benzamido]-butyric acid,
5-[4-methyl-3-nitro-N-(biphenyl-2-yl)benzamido]valeric acid,
5-[m-chloro-N-(4'-methoxybiphenyl-4-yl)benzamido]-valeric acid,
5-[p-fluoro-N-(6-ethoxybiphenyl-3-yl)benzamido]valeric acid,
5-[p-methoxy-N-(2'-fluorobiphenyl-2-yl)benzamido]-valeric acid,
5-[N-(4'-chlorobiphenyl-4-yl)methacryloylamido]valeric acid,
6-[o-methoxy-N-(6-methylbiphenyl-2-yl)benzamido]caproic acid,
6-[3,5-dichloro-N-(4,4'-dimethylbiphenyl-3-yl)benzamido]-caproic acid,
6-[2,4-dimethyl-N-(4'-chlorobiphenyl-4-yl)benzamido]-caproic acid,
6-[3-methoxy-4-methyl-N-(2'-fluorobiphenyl-2-yl)benzamido]-caproic acid,
6-[4-nitro-N-(biphenyl-2-yl)benzamido]caproic acid,
6-N-(4'-ethoxybiphenyl-4-yl)isovaleroylamido]caproic acid.

Preferred compounds of this aspect of the invention are:
4-[p-chloro-N-(biphenyl-2-yl)benzamido]butyric acid,
4-[N-(biphenyl-2-yl)acetamido]butyric acid,
4-[p-fluoro-N-(biphenyl-2-yl)benzamido]butyric acid,
4-[N-(biphenyl-2-yl)cortonoylamido]butyric acid,
6-[p-chloro-N-(biphenyl-2-yl)benzamido]caproic acid,
and their salts with a base, particularly pharmacologically-compatible salts.

Like compounds Ia and Ib, compounds Ic display valuable pharmacological properties which make them commercially useful. In warm-blooded animals they develop a stomach and liver protective action; in addition they bring about an increase in pancreas and liver (bile) secretion. They also inhibit glucose formation from lactate and pyruvate in the liver. For those compounds Ic with short chains (n=3) stomach- and liver-protective action, as well as the increase in secretion, predominates. Action on glucose metabolism is more pronounced for compounds Ic with longer chains (n=4 or, especially, 5).

Because of their advantageous activity, pharmacologically-acceptable acylbiphenylylaminoalkanoic acids (Ic) and their physiologically-acceptable salts with bases are useful for treating and for prophylaxis of diseases which are attributable to stomach or intestine disorders or to reduced performance of the pancreas, bile and/or liver. These compounds are useful, e.g., for treating gastric or intestinal ulcers, Billroth II, pancreatic insufficienty, sprue, indigestion and malabsorption of different aetiology, acute and chronic pacreatitis, indirect disorders of the pancreatic function (supporting production of secretin and pancreozymin), as well as gall-bladder and bile-duct inflammations, bile-flow disorders, motility disorders of the bile ducts, a feeling of repletion, flatulence, constipation, upper abdominal complaint, hepato-biliar functional disorders, acute and chronic hepatitis, intoxication of the liver, fatty degeneration (or infiltration) of the liver, diabetes (maturity-onset diabetes), insulin-deficiency diabetes in the form of "brittle diabetes" and late diabetic damage.

Pharmaceutical products contain one or more physiologically-acceptable acylbiphenylylaminoalkanoic acids Ic,
in which
$R^1$ signifies an aliphatic or alicyclic hydrocarbon radical or optionally-substituted phenyl;
(D-E) signifies optionally-substituted and/or optionally-hydrogenated biphenylyl;
n signifies 3, 4 or 5;
and/or their pharmacologically-compatible salts with an inorganic or organic base.

Exemplary compounds (Id*) of the invention comprise acyl(bicyclic aryl)aminoalkanoic acids of formula Id, in which
$R^1$ signifies an aliphatic hydrocarbon radical with from 1 to 7 carbon atoms, an alicyclic hydrocarbon radical with from 5 to 7 ring carbon atoms or optionally-substituted phenyl,

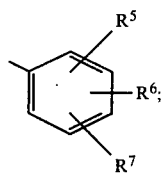

(FZG) signifies an indenyl, indanyl, naphthyl, dihydronaphthyl or tetrahydronaphthyl radical substituted with $R^8$ and $R^9$;
n signifies 3, 4 or 5;
$R^5$, $R^6$ and $R^7$ are the same or different and signify a hydrogen atom (—H), halo, alkyl with from 1 to 4 carbon atoms, alkoxy with from 1 to 4 carbon atoms, alkanoyloxy with from 2 to 5 carbon atoms, nitro (—NO$_2$), hydroxy (—OH) or trifluoromethyl (—CF$_3$);
$R^8$ and $R^9$ are the same or different and signify a hydrogen atom (—H), halo, methyl, lower alkoxy, nitro or trifluoromethyl;
and their salts (particularly pharmacologically-acceptable salts) with an inorganic or organic base.

Preferred (FZG) radicals substituted with $R^8$ and $R^9$ are 5-indanyl, 1-naphthyl or 1,2,3,4-tetrahydronaphthyl-(1) radicals.

Further compounds (Id**) of the invention comprise acyl(bicyclic aryl)aminoalkanoic acids of formula Id, in which
$R^1$ signifies an aliphatic hydrocarbon radical with from 1 to 5 carbon atoms or phenyl substituted with $R^5$, $R^6$ and $R^7$;
(FZG) signifies a group of the formula

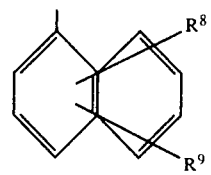

n signifies 3, 4 or 5;
$R^5$, $R^6$ and $R^7$ are the same or different and signify a hydrogen atom (—H), halo, methyl, methoxy, nitro, hydroxy or trifluoromethyl;
$R^8$ and $R^9$ are the same or different and signify a hydrogen atom (—H), chloro, ethoxy, methoxy or nitro;
and their salts (particularly pharmacologically-acceptable salts) with an inorganic or organic base.

Other compounds (Id***) of the invention comprise acyl(bicyclic aryl)aminoalkanoic acids of formula Id, in which
$R^1$ signifies an aliphatic hydrocarbon radical with from 1 to 5 carbon atoms or a phenyl radical substituted with $R^5$, $R^6$ and $R^7$;
(FZG) signifies a group of the formula

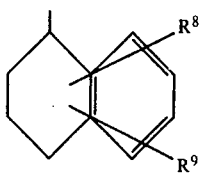

n signifies 3, 4 or 5;
$R^5$, $R^6$ and $R^7$ are the same or different and signify a hydrogen atom (—H), halo, methyl, methoxy, nitro, hydroxy or trifluoromethyl;
$R^8$ and $R^9$ are the same or different and represent a hydrogen atom (—H), chloro, methoxy or nitro;
and their salts (particularly pharmacologically-acceptable salts) with an inorganic or organic base.

Still further compounds (Id****) of the invention comprise acyl(bicyclic aryl)aminoalkanoic acids of formula Id,
in which
$R^1$ signifies an aliphatic hydrocarbon radical with from 1 to 5 carbon atoms or a phenyl radical substituted with $R^5$, $R^6$ and $R^7$;
(FZG) signifies a group of the formula

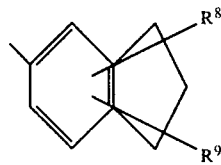

n signifies 3, 4 or 5;
$R^5$, $R^6$ and $R^7$ are the same or different and represent a hydrogen atom (—H), halo, methyl, methoxy, nitro, hydroxy or trifluoromethyl;
$R^8$ and $R^9$ are the same or different and represent a hydrogen atom (—H), chloro, methoxy or nitro;
and their salts (particularly pharmacologically-acceptable salts) with an inorganic or organic base.

Preferred compounds of formula Id are those in which $R^1$ represents an alkyl group with from 1 to 3 carbon atoms or a substituted phenyl radical; $R^5$ signifies a hydrogen atom (—H); $R^6$ represents a hydrogen atom (—H), chloro, methoxy, hydroxy or trifluoromethyl; $R^7$ represents a hydrogen atom (—H) or chloro; $R^8$ represents a hydrogen atom (—H) or methoxy; $R^9$ represents a hydrogen atom (—H); and n is 3, 4 or 5.

Particularly preferred compounds of formula Id are those in which $R^1$ signifies an alkyl group with from 1 to 3 carbon atoms or a substituted phenyl radical; $R^5$ signifies a hydrogen atom (—H); $R^6$ signifies a hydrogen atom (—H), chloro, methoxy or trifluoromethyl; $R^7$ signifies a hydrogen atom (—H) or chloro; each of $R^8$ and $R^9$ signifies a hydrogen atom (—H); and n signifies 3 or 5.

Representative compounds of formula Id are, for example:
4-[p-methoxy-N-(4-chloro-1-naphthyl)benzamido]butyric acid,
4-[m-trifluoromethyl-N-(2-methyl-1-naphthyl)benzamido]butyric acid,
4-[3,5-dichloro-N-(2-methoxy-1-naphthyl)benzamido]butyric acid,
4-[o-fluoro-N-(4-methyl-1-naphthyl)benzamido]butyric acid,
4-[N-(4-methoxy-1-naphthyl)-n-butyramido]butyric acid,
4-[3-methoxy-4-methyl-N-(1-naphthyl)benzamido]butyric acid,
4-[N-(4-hydroxy-1-naphthyl)-p-toluoylamido]butyric acid,
4-[3-fluoro-4-methyl-N-(4-nitro-1-naphthyl)benzamido]butyric acid,
4-[3,4-diethoxy-N-(1-naphthyl)benzamido]butyric acid,
4-[4-methyl-3-nitro-N-(7-methoxy-1-naphthyl)benzamido]butyric acid,
4-[N-(4-bromo-1-naphthyl)hexanamido]butyric acid,
4-[N-(3,4-dinitro-1-naphthyl)acetamido]butyric acid,
4-[N-(3-bromo-4-methyl-1-naphthyl)isovalerylamido]butyric acid,
4-[4-chloro-3-nitro-N-(4-ethoxy-1-naphthyl)benzamido]valeric acid,
4-[2,4-dichloro-N-(4-chloro-1-naphthyl)benzamido]valeric acid,
5-[N-(4-methoxy-1-naphthyl)-m-toluoylamido]valeric acid,
5-[N-(5-nitro-1-naphthyl)propionamido]valeric acid,
6-[3,4-dichloro-N-(1-naphthyl)benzamido]caproic acid,
6-[4-methyl-3-nitro-N-(4-ethoxy-1-naphthyl)benzamido]caproic acid,
6-[N-(1-naphthyl)methacryloylamido]caproic acid,
6-[N-(5-methoxy-2-naphthyl)crotonoylamido]caproic acid,
4-[N-(5-methoxy-1,2,3,4-tetrahydro-1-naphthyl)hexanamido]-butyric acid,
4-[N-(7-methoxy-1,2,3,4-tetrahydro-2-naphthyl)propionamido]-butyric acid,
6-[N-(6,7-dimethoxy-1,2,3,4-tetrahydro-2-naphthyl)acetamido]-caproic acid,
4-[3,4-dichloro-N-(5,6,7,8-tetrahydro-1-naphthyl)benzamido]-butyric acid,
4-[N-(1-indanyl)acetamido]butyric acid,
4-[p-chloro-N-(2-indanyl)benzamido]butyric acid,
6-[3,4-dichloro-N-(2-indanyl)benzamido]caproic acid,
4-[3,4-dimethoxy-N-(4-indanyl)benzamido]butyric acid,
6-[3-fluoro-4-methyl-N-(4-indanyl)benzamido]caproic acid, and
6-[N-(5-indanyl)isovalerylamido]caproic acid.

Particularly interesting compounds of formula Id are:
4-[N-(α-naphthyl)acetamido]butyric acid,
4-[m-trifluoromethyl-N-(α-naphthyl)benzamido]-butyric acid,
4-[5-chloro-2-methoxy-N-(α-naphthyl)benzamido]-butyric acid,
5-[p-chloro-N-(α-naphthyl)benzamido]valeric acid,
6-[p-chloro-N-(α-naphthyl)benzamido]caproic acid,
5-[N-(α-naphthyl)isobutyramido]valeric acid,
4-[N-(6-methoxy-1,2,3,4-tetrahydro-1-naphthyl)propionamido]-butyric acid,
4-[3,4-dichloro-N-(indan-5-yl)benzamido]butyric acid,
5-[p-chloro-N-(indan-5-yl)benzamido]valeric acid
and their parmacologically-compatible salts.

The compounds of formula Id display valuable pharmacological properties which make them commercially useful. In warm-blooded animals they develop, in the main, a stomach-protective action and an increase in pancreatic secretion; in addition they exert an effect (antiheptotoxic effect and choleresis) on the liver and gall. They also inhibit formation of glucose from lactate and pyruvate in the liver. Protective action on the stomach and liver and an increase in secretion predominate with the use of compounds Id having short chains (n=3). The action on glucose metabolism is more strongly pronounced with the use of compounds Id having longer chains (n=4 or, especially, 5).

Because of their advantageous activity pharmacologically-acceptable acyl(bicyclic aryl)aminoalkanoic acids Id and their physiologically-acceptable salts are suitable for the treatment of prophylaxis of diseases which are attributable to disorders of the stomach or intestine or to reduced performance of the pancreas, bile and/or liver. These compounds are useful, e.g., for treating gastric or intestinal ulcers, Billroth II, pancreatic insufficiency, indigestions and malabsorptions, sprue, pancreatitis, indirect disorders of the pancreatic function (supporting production of secretin and pancreozymin), as well as gall-bladder and bile-duct inflammations, bile-flow disorders, motility disorders of the bile ducts, a feeling of repletion, flatulence, constipation, upper abdominal complaints, hepatobiliar functional disorders, acute and chronic hepatitis, intoxication of the liver, fatty degeneration (or infiltration) of the liver, diabetes (maturity onset diabetes), insulin-deficiency diabetes in the form of "brittle diabetes" and late diabetic damage.

Pharmaceutical preparations contain one or more physiologically-acceptable acyl(bicyclic aryl)aminoalkanoic acids Id,
in which
$R^1$ signifies an aliphatic or alicyclic hydrocarbon radical or an optionally-substituted phenyl group;
(FZG) signifies an optionally-substituted and/or optionally-hydrogenated bicyclic arcyl radical with from 8 to 12 ring carbon atoms;
n signifies 3, 4 or 5;
and/or their pharmacologically-compatible salts with an inorganic or organic base.

Illustrative pharmaceutical products are those which contain any pharmacologically-acceptable aminoalkanoic acid of formula I or of any previously-noted and more-limited embodiment and/or their pharmacologically-compatible salts with an inorganic or organic base.

The pharmaceutical products are produced from compounds of formula I (which are novel) according to known processes. As pharmaceutical products, the new compounds are used as such or in combination with suitable pharmaceutical carrier, excipient and/or filler. When the new pharmaceutical preparations contain [in addition to active principle(s)] pharmaceutical carrier, excipient and/or filler, the active-principle content of the preparations is from 1 to 95, preferably from 15 to 85, percent by weight of the total preparation weight.

In accordance with the invention the active principles are administered (in the field of human and veterinary medicine) in any dosage form and by any suitable route, for example, systemic, provided that the formation or maintenance of adequate blood or tissue levels or local concentrations of active principle is ensured. This is carried out either by oral, rectal or parenteral administration in suitable doses. More advantageously, the pharmaceutical preparation of the active principle is employed in the form of a unit dose which is designed for the particular mode of administration actually used. A unit dose is, for example, in the form of a tablet, a pill, a capsule, a suppository, or a measured volume of a powder, a granulate, a solution, an emulsion, a suspension, a sol or a gel.

"Unit dose", in the sense of the present invention, is a physically-determined unit which contains an individual quantity of the active component in combination with a pharmaceutical carrier; the active-principle content of a unit dose corresponds to a fraction or multiple of the individual therapeutic dose. An individual dose preferably contains the quantity of active principle which is administered in a single application and which usually corresponds to a whole, a half, a third or a quarter of the daily dose. If (for an individual therapeutic administration) only a fraction, such as a half or a quarter, of the unit dose is required, the unit dose is advantageously divisible, for example in the form of a table with a notch for breaking.

The pharmaceutical preparations according to the invention, if they occur in unit doses and are intended for application, for example, to human beings, contain from 0.5 to 1000 mg, advantageously from 1 to 500 or even to 750 mg and especially from 5 to 400 or 500 mg of active principle of formula I.

Generally speaking, it is advantageous, both in human medicine and in veterinary medicine, to administer the active principle or principles in oral administration in a daily dose of from 0.01 to 40, preferably from 0.1 to 30 and especially from 0.2 to 20, mg/kg of body weight, possibly in the form of several, preferably 2 to 3, individual administrations, in order to achieve the desired results. An individual administration contains the active principle or principles in quantities of from 0.01 to 20, preferably from 0.1 to 15 and especially from 0.2 to 10, mg/kg of body weight.

In a parenteral treatment, for example intramuscular or intravenous application, similar dosages are used. With this therapy one administers from 50 to 1000 mg of active principle.

The therapeutic administration of the pharmaceutical preparation is carried out in the case of long-term medication generally at fixed points of time, such as from 1 to 4 times a day, for example after each meal and/or in the evening. In the case of acute attacks the medication is administered at varying points of time. Under certain circumstances it may be necessary to differ from the said dosages, namely: according to the nature, the body weight and the age of the patient to be treated, the nature and severity of the disease, the nature of the preparation and the application of drug, as well as the period of time or intervals within which administration takes place. Thus in some cases it may be sufficient to manage with less than the previously-mentioned quantity of active principle, whereas in other cases the noted quantity of active principle must be exceeded. The determination of the optimum dosage and type of application of active principle necessary in each case is, at any time, carried out by the expert on the basis of his technical knowledge.

The pharmaceutical preparations consist, as a rule, of pharmacologically-acceptable active principle according to the invention and non-toxic pharmaceutically-compatible drug excipients which are used in admixture or as diluent in solid, semi-solid or liquid form or as an encapsulating agent, for example in the form of a capsule, a tablet coating, a bag or other container, for the therapeutically-active component. An excipient serves, for example, as a vehicle for the uptake of the medicament by the body, as a formulation aid, as a sweetening agent, as a flavor corrector, as coloring material or as a preservative. Carriers are, in each instant, adapted by a specialist in the disease to be treated with the pharmaceutical preparation.

For oral use the active principle is, for example, in the form of tablets, pills, hard and soft capsules (for example of gelatin), dispersible powder, granulates, aqueous and oily suspensions, emulsions, solutions or syrups.

Tablets optionally contain inert diluents, for example calcium carbonate, calcium phosphate, sodium phosphate or lactose; granulating and distributing agents, for example maize starch or alginates; binders, such as starch, gelatin or gum acacia; and lubricants, such as aluminum or magnesium stearate, talcum or silicone oil. They are also optionally provided with a coating which is, e.g., designed in such a way that it gives a delayed solution and resorption of the drug in the gastro-intestinal tract and therefore ensures, for example, better compatibility, protraction or retarding. Gelatin capsules optionally contain the pharmaceutical product mixed with a solid diluent, for example calcium carbonate or kaolin, or an oily diluent, for example olive oil, groundnut oil or liquid paraffin.

Aqueous suspensions contain, e.g., suspension agents, for example sodium carboxymethylcellulose, methylcellulose, hydroxypropylcellulose, sodium alginate, polyvinylpyrrolidone, gum tragacanth or gum acacia; dispersants and wetting agents, for example polyoxyethylene stearate, heptadecaethylene oxycetanol, polyoxyethylene sorbitol monooleate, polyoxyethylene sorbitan monooleate or lecithin; preservatives, such as methyl or propyl hydroxybenzoates; flavoring materials; sweetening agents, for example saccharin, lactose, sodium cyclamate, dextrose or invert sugar syrup.

Oily suspensions contain, for example, groundnut oil, olive oil, sesame oil, coconut oil or liquid paraffin and thickeners, such as beeswax, paraffin wax or cetyl alcohol; they also optionally contain sweeteners, flavoring materials and anti-oxidants.

Powders and granulates, which are dispersible in water, contain, e.g., the pharmaceutical products in admixture with dispersants, wetting agents and suspending agents, for example those previously mentioned, as well as suspension agents, flavoring materials and coloring materials.

Emulsions contain, for example, olive oil, groundnut oil or liquid paraffin, as well as emulsifiers, such as gum acacia, gum tragacanth, phosphatides, sorbitan monooleate, polyoxyethylene sorbitan monooleate, and sweeteners and flavoring materials.

For rectal use of the pharmaceutical products, one uses suppositories, which are produced with the help of binders which melt at rectal temperature, for example cocoa butter or polyethyleneglycols.

For parenteral use of the pharmaceutical products, one uses sterile injectable aqueous suspensions, isotonic saline solutions or other solutions which contain, e.g., dispersants or wetting agents and/or pharmacologically-compatible diluents, for example propyleneglycol or butyleneglycol.

The active principle or principles are optionally formulated with one or more of the said carrier materials or additives also in a micro-encapsulated form.

When an aminoalkanoic acid of formula I (according to the invention) and/or a salt thereof is used for the treatment of diseases which are based on disorders of the stomach or intestine or on reduced performance of the pancreas, bile and/or liver, the pharmaceutical preparation optionally contains one or more other pharmacologically-active components of other groups of pharmaceutical products, such as antacids, for example aluminum hydroxide and magnesium aluminate; tranquilizers, such as benzodiazepines, for example Diazepam; spasmolytics, such as Bietamiverin and Camylofin; anticholinergics, such as Oxyphencyclimine and Phencarbamide; despumation agents, such as dimethylpolysiloxane; laxatives, such as Bisacodyl; swelling agents, possibly also ferments, bile acids, antibiotics, vitamins, amino acids or fatty acid mixtures.

When aminoalkanoic acid of formula I and/or a salt thereof is formulated as an antidiabetic product, the pharmaceutical preparation optionally contains one or more pharmacologically-active components belonging to different groups of pharmaceutical products, such as additional antidiabetics (sulfonamides, sulfonyl ureas, etc.), for example carbutamide, tolbutamide, chlorpropamide, glibenclamide, glibornuride, glisoxepide, gliquidone and glymidine, or hypolipidaemics, such as clofibrinic acid and nicotinic acid, as well as their derivatives and salts, for example clofibrate, etofibrate and aluminum clofibrate.

Aminoalkanoic acids of formula I and their salts with bases are conventionally synthesized from known starting materials or from starting materials which are readily prepared by one of ordinary skill in the art from available compounds. Illustrative syntheses include:

(a) acylating an aminoalkanoic acid of the formula

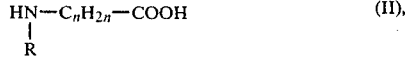

optionally with protection of the carboxyl group, with an acyl derivative of the formula $$R^1-CO-R^{10} \qquad (III),$$

wherein

R, $R^1$ and n have their previously-ascribed meanings, and $R^{10}$ signifies a leaving group, e.g. hydroxy (—OH), halo (chloro or bromo), lower alkylsulfonyloxy (e.g. mesyloxy), benzenesulfonyloxy, substituted benzenesulfonyloxy (e.g. p-tolylsulfonyloxy), lower alkoxy (preferably methoxy or ethoxy), lower alkylmercapto (e.g. methylthio and ethylthio) or $R^1$—CO—O—; and, subsequently, optionally converting the resulting reaction product into one of its salts;

(b) hydrogenating an aminoalkanoic acid of the formula

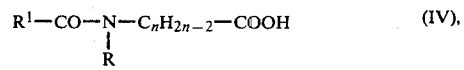

wherein R, $R^1$ and n have their previously-ascribed meanings, optionally with protection of the carboxyl group, and, subsequently, converting the resulting product into one of its salts if the salt form is desired;

(c) reacting an aminoalkanoic acid of the formula

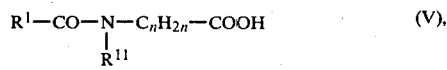

wherein $R^1$ and n have their previously-ascribed meanings, and $R^{11}$ is a hydrogen atom (—H), an alkaline-earth metal (e.g. calcium and magnesium) or, preferably, an alkali metal (e.g. sodium, potassium and lithium), optionally with protection of the carboxyl group, with a compound of the formula $$R-R^{12} \qquad (VI),$$

wherein

R is adamantyl or —C($R^2$)($R^3$)($R^4$) and $R^2$, $R^3$ and $R^4$ have their previously-ascribed meanings, and $R^{12}$ is a leaving group, such as halo (e.g. chloro, bromo and iodo) and trihalomethyl (e.g. trichloromethyl and tribromomethyl), and subsequently converting the resulting reaction product into one of its salts if so desired and (d) solvolyzing a functional aminoalkanoic acid derivative of the formula

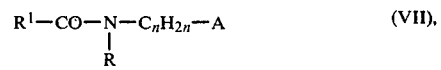

wherein

R, $R^1$ and n have their previously-ascribed meanings, and

A is a functional derivative of a carboxyl group, such as —CN or —C(=X)—Y,

X is =O, =S, =NH or substituted imino, (such as hydroxyimino or lower alkylimino, e.g. methylimino), and Y is —OH (but not when X is =O) or a mono-valent eliminable electrophilic radical, such as, free or substituted amino, hydrazino, mercapto, substituted mercapto, substituted hydroxy, lower alkoxy, azido, halo, morpholino or piperidino, and converting the resulting product to one of its salts if so desired.

When the aminoalkanoic acids of formula II (with protection of the carboxyl group) are reacted, those representatives the protective groups of which do not react with acyl derivatives III are used. Suitable representatives are, for example, salts of inorganic or organic bases, such as alkali or alkaline-earth metal salts, ammonium salts, salts of tertiary-nitrogen bases (e.g. triethylamine and pyridine) or quaternary ammonium salts, or esters of alkanols (including those with from 1 to 5 carbon atoms) or phenalkanols, such as methyl, propyl, butyl, benzyl or phenethyl esters.

The reaction of an aminoalkanoic acid II with an acyl derivative III is carried out according to known methods. The reaction is carried out in suitable solvents, such as water; hydrocarbons, e.g. benzene, toluene and xylene; ethers, e.g. tetrahydrofuran, dioxan and 1,2-dimethoxyethane; ketones, e.g. ethylmethylketones; amides, e.g. dimethylformamide; or sulfoxides, e.g. dimethylsulfoxide. Expediently, the acylation is carried out (when $R^{10}$ is a halo leaving group) in the presence of an acid-binding agent (proton acceptor). If the acyl derivatives III are acid anhydrides, that is when $R^{10}$ signifies $R^1$—CO—O—, it is also sufficient to heat the compounds II and III in an inert solvent.

The reaction temperature can be varied within wide limits, for example from $-20°$ to $+100°$ C., temperatures (10° to 30° C.) around room temperature being preferred. When the compounds II are acylated with the protection of the carboxyl group, then (after the acylation) the protective group is split off again in the usual manner. When a salt is used as a protective group, liberation of the obtained acid I is carried out by reaction with a suitable mineral acid, such as hydrochloric acid or sulfuric acid. When esters are used as protective groups, acylation is followed by saponification of the reaction product to form compounds of formula I. The saponification is preferably carried out with an alcoholic (e.g. ethanolic) alkali-metal hydroxide (e.g. potassium hydroxide) solution at room temperature, optionally with the addition of an inert diluent, such as dioxan or benzene.

Compounds of formula II are produced according to various known processes. Thus they are obtained by reacting haloalkanoic acids of formula VIII, optionally with protection of the carboxyl group as an ester group, with a primary amine of formula IX

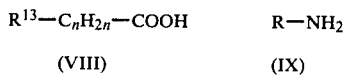

(VIII)        (IX)

in which n and R have their previously-ascribed meanings, and $R^{13}$ signifies halo, preferably chloro or bromo. The reaction is advantageously carried out in the presence of an inert solvent, for example benzene, cyclohexane or diethylether, with the addition of a proton acceptor. As such, an excess of amine IX, which alternatively serves as solvent, is preferably used for the reaction. If desired, however, it is also possible to use a different proton acceptor.

Starting compounds II are also obtained by reacting an amino acid of the formula

in which n has its previously-ascribed meaning, preferably with protection of the carboxyl group, with a compound of formula VI.

If the production of II is carried out from an amino acid X, whose carboxyl group is protected, the protective group is expediently only split off after the reaction of the intermediate product II, obtained with acyl derivative III, so as to obtain end-product I.

Compounds II are also obtained by reacting an alkenoic acid derivative of the formula

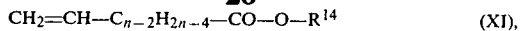

(in which n has its previously-ascribed meaning, and $R^{14}$ signifies an alkyl group with from 1 to 5 carbon atoms or a benzyl group) with an amine of formula IX. The reaction is expediently carried out in the presence of an inert solvent, such as a hydrocarbon, for example benzene, toluene or xylene; an ether, for example tetrahydrofuran, dioxan or 1,2-dimethoxyethane; a ketone, for example methylethylketone; an amide, for example dimethylformamide; a sulfoxide, for example dimethylsulfoxide, a nitrile, for example acetonitrile. Expediently, the reactants are heated in a solvent, for example, by boiling under reflux. The protective group $R^{14}$ is expediently split off only after the reaction of the resultant compound II with the acyl derivative III so as to obtain an end product I.

Compounds II are also obtained by solvolysis of functional aminoalkanoic acid derivatives of the formula

(in which A, R and n have their previously-ascribed meanings) by means of processes which are known to the technician. Expedient forms of execution are described under process variant (d).

Starting products II are also obtained by reacting amines IX qwith lactones of the formula

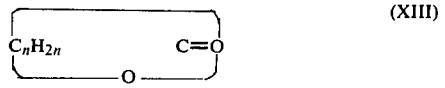

(in which n has its previously-ascribed meaning) in known manner. The reaction is carried out, for example, by heating the reactants IX and XIII in inert solvents, such as ethers, for example diethyl ether and tetrahydrofuran, or nitriles, for example acetonitrile, e.g., to the boiling point of the solvent. The obtained acid is then optionally converted into a corresponding ester, for example by heating in an appropriate alcohol in the presence of a mineral acid, such as hydrochloric acid or sulfuric acid.

Compounds II are also abtained by solvolysis of lactams of the formula

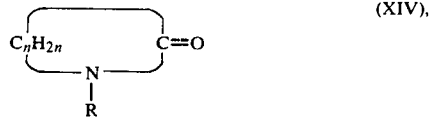

in which R and n have their previously-ascribed meanings. The solvolysis is carried out, for example, as hydrolysis by heating a lactam XIV to a temperature of from 80° to 110° C. with an aqueous or aqueous-alcoholic alkali-metal hydroxide (e.g. sodium hydroxide) solution, or as alcoholysis by heating a lactam (XIV) with an alcohol, such as methanol or ethanol, in the presence of a mineral acid, such as sulfuric acid, to the boiling point.

The intermediate products II are, alternatively, obtained by hydrogenation of iminoalkanoic acids of the formula

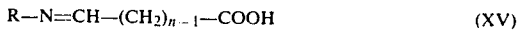

(in which R and n have their previously-ascribed meanings) optionally with protection of the carboxyl group, in known manner. The hydrogenation is carried out, for example, with Raney nickel under hydrogen pressures of from 1 to 250 atmospheres at room temperature in absolute ethanol.

Acids XV are available by the reaction of an amine IX with an oxo-acid ester of the formula $$O=CH-(CH_2)_{n-1}-CO-O-R^{15} \qquad (XVI)$$

in which n has its previously-noted meaning, and $R^{15}$ signifies an alkyl group with from 1 to 5 carbon atoms or a benzyl group.

Hydrogenation according to the process variant (b) is carried out by conventional methods. Thus, aminoalkenoic acids IV are hydrogenated with hydrogen in the presence of a transition-metal or noble-metal catalyst or the corresponding oxides or complexes in inert solvent. Suitable metals are, for example, platinum, palladium, iridium and rhodium. A summary of suitable hydrogenation processes is found, inter alia, in Kirk-Othmer, 11, 418–462; Ullmann, 10, 109–114, 541–555; 14, 630–649. The splitting off of any protective group which may be present is also conventionally effected.

Alkenoic acids IV are obtained, for example, from haloalkenoic acid esters of the formula $$R^{16}-C_nH_{2n-2}-CO-O-R^{15} \qquad (XVII),$$

(in which $R^{15}$ and n have their previously-noted meanings, and $R^{16}$ is halo, preferably bromo) by amination with an amine of formula IX, acylation with an acyl derivative III and, optionally, subsequent saponification. The production is carried out by means of processes which are in themselves known, halogenation and amination, for example, analogous to those described in *J. Heterocycl. Chem.*, 8 (1971) 21; acylation and saponification, inter alia, as described in the present application.

Hydrocarbylation of acylaminoalkanoic acids V (process variant c) is conventionally carried out. For example, compounds V are de-protonated in a suitable inert anhydrous solvent, such as benzene, toluene, xylene, tetrahydrofuran, dimethylglycol, dimethylformamide or dimethylsulfoxide, with an alkali-metal hydride or amide, such as sodium hydride or amide, and then treated with a hydrocarbyl derivative VI, in which $R^{12}$ signifies halo (preferably chloro or bromo), alkylsulfonyloxy, such as mesyloxy, or a benzensulfonyloxy, such as p-tolylsulfonyloxy. When dimethylsulfoxide is used, it is also possible to use potassium hydroxide as the de-protonating agent (cf. Isele and Lüttringhaus, *Synthesis*, 1971, 266).

Haloalkanoic acids VIII, amines IX and lactams XIV are known compounds or are produced by analogy processes; for example, the haloalkanoic acids VIII are accessible by the solvolysis, such as hydrolysis or alcoholysis, of corresponding lactones, followed by halogenation; the amines IX are obtained by reducing corresponding nitro compounds (prepared by nitration); or lactams XIV are accessible by N-hydrocarbylation of corresponding N-unsubstituted lactams.

The solvolysis according to process variant (d) is carried out conventionally.

Preferred representatives of functional acid derivatives VII are those in which

A represents a —CN group or a

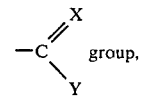
group, and in which

X signifies an oxygen atom, a sulfur atom or an iminio group and

Y signifies amino, monoalkylamino, dialkylamino, phenylamino, alkoxy, alkylthio, chloro or bromo.

Particularly preferred representatives of functional acid derivative VII are the corresponding acid amines, alkyl esters of the acid and nitriles, that is to say those compounds of the formula VII in which A represents a —CO—NH$_2$, —CO—NH—R$^{14}$, —CO—NR$^{14}$$_2$, —CO—O—R$^{14}$ or —CN group, and R$^{14}$ has its previously-ascribed meaning. They constitute valuable intermediate products for the production of compounds I and of their salts.

For solvolysis of functional carboxylic acid derivatives VII a water-splitting medium (which consists wholly or partly of water or of an agent which splits off water under hydrolysis conditions) is used. The reaction is, e.g., carried out as a homogeneous reaction, usually in the presence of a polar organic solvent or of a solubilizer. Advantageously-employed solvents include, for example, low-molecular alcohols, dioxan, acetone, low-molecular carboxylic acids, N-methylpyrrolidone, sulfolan or dimethylsulfoxide. However, it is also possible to carry out the hydrolysis as a heterogeneous reaction. The pH of the medium which splits off water depends upon the chemical nature of the acid derivative employed and also on the nature of the compound of formula I desired; it can therefore be neutral, acid or basic. It is adjusted to the desired value by means of acid, base or buffer.

The hydrolysis temperature is between 0° C. and the boiling point of the medium which splits off water, generally between 0° and 150° C., especially between 20° and 120° C. The hydrolysis temperature depends individually also on whether the operation is carried out under pressure or without pressure. The reaction time is between 10 minutes and 20 hours, according to the charge, reaction temperature and other reaction parameters. After the hydrolysis has been completed, an acid I is isolated by usual methods, for example by recrystallization or by acidification of its solution, possibly while concentrating the solution. For purification it is possible to extract its alkaline solution with an organic solvent, for example diethylether, benzene, chlorobenzene, chloroform or methylene chloride, which is not miscible with the alkaline solution.

The carboxylic acid derivative VII is obtained by methods which are known to the technician. For example, it is obtained by reacting a functional haloalkanoic acid derivative of the formula $$R^{13}-(CH_2)_n-A \qquad (XVIII)$$

(in which $R^{13}$, n and A have their previously-noted meanings) with an amine IX, followed by acylation with an acyl derivative III. Alternatively, an acylaminoalkanoic acid derivative of the formula

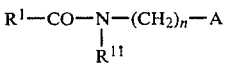

(in which $R^1$, $R^{11}$, A and n have their previously-ascribed meanings) is reacted with a compound VI.

Conversion of acids of formula I into their salts is carried out by direct alkaline hydrolysis of the acid derivatives of formula VII. As alkaline reactants the particular inorganic or organic base (whose salt is desired) is used. However, the salts are optionally obtained by reacting the acids of formula I with a stoichiometric equivalent of a corresponding base, for example sodium hydroxide or sodium alcoholate; readily-soluble salts are converted by double decomposition into sparingly-soluble salts; or any salts are converted into salts which are pharmacologically compatible.

Further exemplary compounds, prepared by the previously-described procedures, are:

N-(2,4-diethylbenzoyl)-5-[adamantyl-(1)-amino]valeric acid

N-(2,4,6-trimethylbenzoyl)-6-[adamantyl-(1)-amino]caproic acid

N-(2,4,6-trichlorobenzoyl)-4-[adamantyl-(1)-amino]butyric acid

N-crotonoyl-4-[adamantyl-(1)-amino]butyric acid

N-(p-fluorobenzoyl)-6-cyclohexylmethylaminocaproic acid

N-hexylcarbonyl-4-[adamantyl-(1)-amino]butyric acid

N-benzoyl-4-[adamantyl-(1)-amino]butyric acid

N-acetyl-4-[adamantyl-(1)-amino]butyric acid lithium salt

N-benzoyl-5-(2-biphenylylamino)valeric acid

N-(4-chloro-2-ethylbenzoyl)-6-[adamantyl-(1)-amino]caproic acid

N-(5-hydroxy-3-propylbenzoyl)-5-inden-4-ylaminovaleric acid potassium salt

N-(m-chlorobenzoyl)-4-[adamantyl-(1)-amino]butyric acid

N-(3-cyclohexylcarbonyl)-5-[adamantyl-(1)-amino]valeric acid

N-(sec.-butylcarbonyl)-6-(p-trifluoromethylbenzylamino)-caproic acid

N-pivaloyl-4-[1,2,5,6-tetrahydronaphthyl-(2)-amino]butyric acid.

The following examples provide a further explanation and illustration of the invention without restricting it. The abbreviations, M.P. and B.P., signify melting point and boiling point, respectively. All temperatures are in degrees Centigrade.

EXAMPLE 1

N-(p-chlorobenzoyl-4-[(1,1,3,3-tetramethylbutyl-)amino]butyric acid $R^1$=p-chlorophenyl, $R^2=R^3=$—$CH_3$, $R^4=$—$CH_2$—$C(CH_3)_3$, n=3

(a) Ethyl N-(p-chloro)benzoyl-4-[(1,1,3,3-tetramethylbutyl-)amino]butyrate 19.5 g of ethyl 4-bromobutyrate, 25.9 g of 1,1,3,3-tetramethylbutylamine and 20 ml of cyclohexane are stirred together for 14 days at room temperature. The salt [ethyl 4-(1,1,3,3-tetramethylbutylamino)butyrate hydrobromide] which separates out, is filtered off and washed with cyclohexane. The filtrates are concentrated by evaporation, and all the volatile components are driven off from the residue under a pressure of approximately 0.5 mm Hg and at a bath temperature of at most 50°.

The residue is dissolved in 30 ml of benzene and, after the addition of 8.8 g of ethyldiisopropylamine, 12.0 g of p-chlorobenzoyl chloride are added dropwise with stirring at room temperature. After half an hour the salt (which separates out) is filtered off; the filtrate is then concentrated by evaporation, and the evaporation residue is recrystallized from cyclohexane to obtain 22.0 g (57.6% of theory) of ethyl N-(p-chloro)benzoyl-4-[(1,1,3,3,-tetramethylbutyl)amino]butyrate, M.P. 79° to 81°.

(b) N-(p-chloro)benzoyl-4-[(1,1,3,3-tetramethylbutyl-)amino]butyric acid

A mixture of 17.0 g of ethyl N-(p-chloro)benzoyl-4-[(1,1,3,3-tetramethylbutyl)amino]butyrate in 100 ml of benzene is mixed with a solution of 3.5 g of potassium hydroxide in 20 ml of ethanol. The mixture is stirred for 20 hours at room temperature. The solvent is evaporated off in vacuo at a bath temperature of a maximum of 50°, and the residue is dissolved in water. The aqueous solution is extracted once with diethylether in order to remove impurities and unreacted initial material before acidifying the aqueous solution with dilute hydrochloric acid. The resultant precipitate is filtered off, dried and recrystallized from benzene/ligroin to obtain 13.3 g (83.6% of theory) of N-(p-chloro)-benzoyl-4-[(1,1,3,3-tetramethylbutyl)amino]butyric acid, M.P. 141° to 143° C.

EXAMPLE 2

N-(p-fluoro)benzoyl-4-[(1,1,3,3-tetramethylbutyl-)amino]butyric acid $R^1$=p-fluorophenyl, $R^2=R^3=$—$CH_3$, $R^4=$—$CH_2$—$C(CH_3)_3$, n=3.

Analogously to Example 1, ethyl N-(p-fluoro)benzoyl-4-[(1,1,3,3-tetramethylbutyl)amino]butyrate is obtained as a viscous oil by reacting the reaction product of ethyl 4-bromobutyrate and 1,1,3,3-tetramethylbutylamine with p-fluorobenzoyl chloride, the saponification of which gives N-(p-fluoro)benzoyl-4-[(1,1,3,3-tetramethylbutyl)amino]-butyric acid (M.P. 114° to 117°).

EXAMPLE 3

N-(p-chloro)benzoyl-4-(tert.butylamino)butyric acid $R_1$=p-chlorophenyl, $R^2=R^3=R^4=$—$CH_3$, n=3.

Analogously to Example 1, ethyl N-(p-chloro)benzoyl-4-(tert.-butylamino)butyrate (M.P. 62° to 63°) is obtained by reacting the reaction product of ethyl 4-bromobutyrate and tert.-butylamine with p-chlorobenzoyl chloride, the saponification of which yields N-(p-chloro)benzoyl-4-(tert.-butylamino)butyric acid (M.P. 126° to 127°).

EXAMPLE 4

N-(3,4,5-trimethoxy)benzoyl-6-(tert.butylamino)caproic acid $R^1$=3,4,5-trimethoxyphenyl, $R^2=R^3=R^4=$—$CH_3$, n=5

Analogously to Example 1, ethyl N-(3,4,5-trimethoxy)benzoyl-6-(tert.-butylamino)caproate (a viscous oil which cannot be distilled without decomposition) is obtained by reacting the reaction product of ethyl 6- bromocaproate and tert.-butylamine with 3,4,5-trimethoxybenzoyl chloride, the saponification of which yields N-trimethoxybenzoyl-6-(tert.-butylamino)caproic acid (M.P. 83° to 85°).

EXAMPLE 5

N-(p-chloro)benzoyl-4-[(1,1-dimethylpropyl)amino]butyric acid $R^1$ = p-chlorophenyl, $R^2 = R^3 =$ —$CH_3$, $R^4 =$ —$C_2H_5$, n = 3

Analogously to Example 1 ethyl N-(p-chloro)benzoyl-4-[(1,1-dimethylpropyl)amino]butyrate (M.P. 65° to 67°) is obtained by reacting the reaction product of ethyl 4-bromobutyrate and 1,1-dimethylpropylamine with p-chlorobenzoyl chloride, the saponification of which yields N-(p-chloro)-benzoyl-4-[(1,1-diemthylpropyl)amino]butyric acid (M.P. 79° to 81°).

EXAMPLE 6

N-(2,4-dichloro)benzoyl-4-[(1,1-dimethylpropyl)amino]butyric acid $R^1$ = 2,4-dichlorophenyl, $R^2 = R^3 =$ —$CH_3$, $R^4 =$ —$C_2H_5$, n = 3

Analogously to Example 1, ethyl N-(2,4-dichloro)-benzoyl-4-[(1,1-dimethylpropyl)amino]butyrate (M.P. 75° to 77°) is obtained by reacting the reaction product of ethyl 4-bromobutyrate and 1,1-dimethylpropylamine with 2,4-dichlorobenzoyl chloride, the saponification of which yields 2,4-dichlorobenzoyl-4-[(1,1-dimethylpropyl)amino]-butyric acid (M.P. 124° to 126°).

EXAMPLE 7

N-(n-butyryl)-4-[(1,1-dimethylpropyl)amino]butyric acid $R^1$ = n—$C_3H_7$, $R^2 = R^3 =$ —$CH_3$, $R^4 =$ —$C_2H_5$, n = 3

19.5 g of ethyl 4-bromobutyrate, 26.1 g of 1,1-dimethylpropylamine and 20 ml of cyclohexane are stirred together at room temperature for 10 days. The resultant precipitate is filtered off and the filtrate concentrated by evaporation. After all the volatile components have been removed at a bath temperature of 50° and a pressure of 0.5 mm Hg, the residue is stirred with 41 g of n-butyric anhydride, 33.4 ml of pyridine and 100 ml of benzene for 5 hours at room temperature. The mixture is concentrated by evaporation at a pressure of 10 mm Hg and a bath temperature of 90°. The residue, taken up in 100 ml of benzene, is mixed with a solution of 1.7 g of potassium hydroxide in 20 ml of ethanol. After standing for 20 hours at room temperature, the solvent is evaporated off at reduced pressure, and the residue is dissolved in water; the aqueous solution is washed once with diethylether and then acidified with dilute hydrochloric acid. The precipitate which separates out and is at first oily is filtered off, dried and recrystallized from ethyl acetate/cyclohexane to obtain 8.9 g (36.6% of theory) of N-(n-butyryl)-4-[(1,1-dimethylpropyl)amino]butyric acid (M.P. 70° to 72°).

EXAMPLE 8

N-(p-chloro)benzoyl-4-[(2-methyl-3-butyn-2-yl)amino]butyric acid $R^1$ = p-chlorophenyl, $R^2 =$ —C≡CH, $R^3 = R^4 =$ —$CH_3$, n = 3

Analogously to Example 1, ethyl N-(p-chloro)benzoyl-4-[(2-methyl-3-butyn-2-yl)amino]butyrate (M.P. 68° to 70°) is obtained by reacting the reaction product of ethyl 4-bromobutyrate and 2-methyl-3-butyn-2-ylamine with p-chlorobenzoyl chloride, the saponification of which yields N-(p-chloro)benzoyl-4-[(2-methyl-3-butyn-2-yl)amino]butyric acid (M.P. 102° to 104°).

EXAMPLE 9

N-(p-chloro)benzoyl-4-[(3-ethyl-1-pentyn-3-yl)amino]butyric acid $R^1$ = p-chlorophenyl, $R^2 =$ —C≡CH, $R^3 = R^4 =$ —$C_2H_5$, n = 3

Analogously to Example 1 ethyl N-(p-chloro)benzoyl-4-[(3-ethyl-1-pentyn-3-yl)amino]butyrate (M.P. 73° to 75°) is obtained by reacting the reaction product of ethyl 4-bromobutyrate and 3-ethyl-1-pentyn-3-ylamine with p-chlorobenzoyl chloride, the saponification of which gives N-(p-chloro)benzoyl-4-[(3-ethyl-1-pentyn-3-yl)amino]butyric acid (M.P. 92° to 94°).

EXAMPLE 10

N-(p-chloro)benzoyl-4-[(1-ethynylcyclohexyl-1)-amino]butyric acid $R^1$ = p-chlorophenyl, $R^2 =$ —C≡CH, $R^3$ and $R^4 =$ —$(CH_2)_5$—, n = 3

Analogously to Example 1, ethyl N-(p-chloro)benzoyl-4-[(1-ethynylcyclohexyl-1)-amino]butyrate (M.P. 84° to 86°) is obtained by reacting the reaction product of ethyl 4-bromobutyrate and 1-ethynylcyclohexylamine with p-chlorobenzoyl chloride, the saponification of which gives N-(p-chloro)benzoyl-4-[(1-ethynylcyclohexyl-1)-amino]butyric acid (M.P. 120° to 122°).

EXAMPLE 11

N-acetyl-4-[(1-ethynylcyclohexyl-1)-amino]butyric acid $R^1 =$ —$CH_3$, $R^2 =$ —C≡CH, $R^3$ and $R^4 =$ —$(CH_2)_5$—, n = 3

Analogously to Example 1 ethyl N-acetyl-4-[(1-ethynylcyclohexyl-1)-amino]butyrate (M.P. 73° to 75°) is obtained by reacting the reaction product of ethyl 4-bromobutyrate and 1-ethynylcyclohexylamine with acetyl chloride, the saponification of which gives N-acetyl-4-[(1-ethynylcyclohexyl-1)-amino]butyric acid (M.P. 103° to 105°).

EXAMPLE 12

N-(p-chloro)benzoyl-4-[(1-propylcyclohexyl-1)-amino]butyric acid $R^1$ = p-chlorophenyl, $R^2$ = n—$C_3H_7$, $R^3$ and $R^4 =$ —$(CH_2)_5$—, n = 3

Analogously to Example 1 ethyl N-(p-chloro)benzoyl-4-[{1-(n-propyl)cyclohexyl-1}-amino]butyrate (a viscous oil which cannot be distilled without decomposition) is obtained by reacting the reaction product of ethyl 4-bromobutyrate and 1-(n-propyl)cyclohexylamine with p-chlorobenzoyl chloride, the saponification of which gives N-(p-chloro)benzoyl-4-[{1-(n-propyl)-cyclohexyl-1}-amino]butyric acid (M.P. 110° to 112°).

EXAMPLE 13

N-(p-chloro)benzoyl-4-[{1-(n-butyl)cyclopentyl-1}-amino]butyric acid $R^1$ = p-chlorophenyl, $R^2$ = n—$C_4H_9$, $R^3$ and $R^4 =$ —$(CH_2)_4$—, n = 3

Analogously to Example 1 ethyl N-(p-chloro)benzoyl-4-[{1-(n-butyl)cyclopentyl-1}-amino]butyrate (M.P. 85° to 87°) is obtained by reacting the reaction product of ethyl 4-bromobutyrate and 1-(n-butyl)cyclopentylamine with p-chlorobenzoyl chloride, the saponification of which gives N-(p-chloro)benzoyl-4-[{1-(n-butyl)cyclopentyl-1}-amino]-butyric acid (M.P. 91° to 93°).

EXAMPLE 14

N-(p-chloro)benzoyl-4-(1-adamantyl)aminobutyric acid $R^1$ = (p-chloro)phenyl, $R^2$ and $R^3$ and

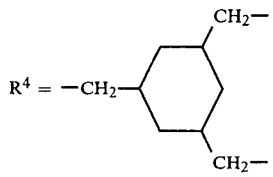

n = 3

Analogously to Example 1, ethyl N-(p-chloro)benzoyl-4-[(1-adamantyl)amino]butyrate (M.P. 103° to 105°) is obtained by reacting the reaction product of ethyl 4-bromobutyrate and 1-aminoadamantane with p-chlorobenzoyl chloride, the saponification of which gives N-(p-chloro)benzoyl-4-[(1-adamantyl)amino]-butyric acid (M.P. 164° to 166°).

EXAMPLE 15

N-(p-chloro)benzoyl-4-cyclooctylaminobutyric acid $R^1$ = p-chlorophenyl, $R^2$ = —H, $R^3$ and $R^4$ = —$(CH_2)_7$—, n = 3

Analogously to Example 1, ethyl N-(p-chloro)benzoyl-4-cyclooctylaminobutyrate (an oil which cannot be distilled without decomposition) is obtained by reacting the reaction product of ethyl 4-bromobutyrate and cyclooctylamine with p-chlorobenzoyl chloride, the saponification of which yields N-(p-chloro)benzoyl-4-cyclooctylaminobutyric acid (M.P. 109° to 110°).

EXAMPLE 16

N-benzoyl-4-(n-butylamino)butyric acid $R^1$ = phenyl, $R^2$ = $R^3$ = —H, $R^4$ = n—$C_3H_7$, n = 3

15.5 g of n-butylpyrrolidone is heated for 20 hours under reflux in a mixture of 15 g of sodium hydroxide in 100 ml of water. Into the solution (which is cooled to 0° and vigorously agitated) there is slowly introduced (drop by drop) 23.1 g of benzoyl chloride, which is then stirred for a further 5 hours; while further cooling, 5 N hydrochloric acid is added until the reaction mixture becomes acid. The precipitated deposit, which still contains benzoic acid, is separated and recrystallized several times from ligroin to obtain 13.6 g (47% of theory) of N-benzoyl-4-(n-butyl)aminobutyric acid (M.P. 62° to 64°).

EXAMPLE 17

N-(p-chloro)benzoyl-5-(n-butylamino)valeric acid $R^1$ = p-chlorophenyl, $R^2$ = $R^3$ = —H, $R^4$ = n—$C_3H_7$, n = 4

(a) 1-(n-butyl)-δ-valerolactam

To a solution of 49.6 g of δ-valerolactam in 300 ml of anhydrous dimethylsulfoxide one adds 33.6 g of finely-powdered potassium hydroxide and then one adds (drop by drop), while stirring and with occasional cooling, 82.2 g of 1-bromobutane within 1 hour. The mixture is stirred for a further 3 hours at 70° C. and then cooled, mixed with 1.5 liters of water and then extracted with diethyl ether. The ether phase is washed with water, dried and evaporated to dryness. The evaporation residue is distilled in vacuo to obtain 42.5 g (54.7% of theory) of 1-(n-butyl)-δ-valerolactam (B.P. 122°/13 mm Hg).

(b) N-(p-chloro)benzoyl-5-(n-butylamino)valeric acid 18.0 g of 1-(n-butyl)-δ-valerolactam, 14.0 g of sodium hydroxide and 280 ml of water are heated together for 8 hours to boiling point under reflux. The solution is then cooled and adjusted to a pH of 7.5 with dilute hydrochloric acid. Then while stirring and continuously checking the pH, one simultaneously adds (drop by drop) 22.3 g of p-chlorobenzoyl chloride and 22.0 g of 25% aqueous sodium hydroxide solution, the pH being maintained between 7 and 8. After unreacted initial material and also impurities have been removed by extraction with diethyl ether, the aqueous solution is acidified with dilute hydrochloric acid and the oily deposit which separates out is taken up in methylene chloride. The residue remaining after drying and distilling off the methylene chloride is recrystallized from ethyl acetate/petrol ether to obtain 22.4 g (62% of theory) of N-(p-chloro)benzoyl-5-(n-butylamino)valeric acid (M.P. 64.5° to 65.5°).

EXAMPLE 18

N-(p-chloro)benzoyl-4-benzylaminobutyric acid $R^1$ = p-chlorophenyl, $R^2$ = $R^3$ = —H, $R^4$ = phenyl, n = 3

27.0 g of N-benzylpyrrolidone is heated to boiling under a reflux for 30 hours with 350 ml of 5% sodium hydroxide solution. After cooling, the solution is adjusted to a pH of 8 with dilute hydrochloric acid, and unreacted initial material is extracted with diethyl ether. To the clear aqueous solution 19.7 g of p-chlorobenzoyl chloride is added slowly (drop by drop) while stirring, while (at the same time) adding dilute caustic soda solution in order to maintain the pH at between 7 and 8. After ending the addition of acid chloride, the solution is stirred for a further 30 minutes at pH 8 and then acidified to pH 3 with dilute hydrochloric acid. The deposit which is precipitated is taken up in ethyl acetate; the ethyl acetate phase is dried with magnesium sulfate and concentrated by evaporation. After the addition of petrol ether and cooling, the product crystallizes out to yield 31 g (61% of theory) of N-(p-chloro)benzoyl-4-benzylaminobutyric acid (M.P. 101° to 102°).

EXAMPLE 19

N-(p-chloro)benzoyl-4-benzhydrylaminobutyric acid $R^1$ = p-chlorophenyl, $R^2$ = —H, $R^3$ = $R^4$ = phenyl, n = 3

(a) Ethyl 4-benzhydrylaminobutyrate 19.5 g of ethyl 4-bromobutyrate, 55 g of benzhydrylamine and 30 ml of cyclohexane are stirred at room temperature for 12 days. The resultant crystal paste is diluted with diethyl ether, filtered at the pump and the filtrate concentrated by evaporation. The residue (after evaporation) is distilled in vacuo. The first run which distils over at 100° to 110° (0.02 mm Hg) is excess benzhydrylamine. The main distillate obtained is 21.1 g (71% of theory) of ethyl 4-benzylhydrylaminobutyrate [B.P. 150° to 155° (0.02 mm Hg)].

(b) Ethyl N-(p-chloro)benzoyl-4-benzhydrylaminobutyrate 6.8 g of p-chlorobenzoyl chloride is added drop by drop to a solution of 10.5 g of ethyl 4-benzhydrylaminobutyrate and 5 g of ethyl diisopropylamine in 100 ml of benzene accompanied by cooling and agitation. After a further 2 hours the precipitate is filtered off, the filtrate is evaporated, and the residue on evaporation is recrystallized from ligroin to yield 9.5 g (61.7% of theory) of ethyl N-(p-chloro)benzoyl-4-benzhydrylaminobutyrate (M.P. 68° to 69°).

(c) N-(p-chloro)benzoyl-4-benzhydrylaminobutyric acid 9.1 g of N-(p-chloro)benzoyl-4-benzhydrylaminobutyrate is dissolved in 90 ml of benzene and, after addition of a solution of 1.8 g of potassium hydroxide in 20 ml of ethanol, is stirred at room temperature for 20 hours. The solvent is then distilled off in vacuo, and the residue dissolved in water. The aqueous alkaline solution is washed once with diethyl ether and then acidified with dilute hydrochloric acid. The precipitated product is filtered off, dried and recrystallized from ligroin to yield 8.0 g (94% of theory) of N-(p-chloro)-benzoyl-4-benzhydrylaminobutyric acid (M.P. 110° to 111°).

EXAMPLE 20

N-acetyl-4-benzhydrylaminobutyric acid $R^1$=—$CH_3$, $R^2$=—H, $R^3$=$R^4$=phenyl, n=3

Analogously to Example 19, 10.8 g of ethyl 4-benzhydrylaminobutyrate and 5.2 g of ethyl diisopropylamine are dissolved in 100 ml of benzene and reacted with 3.1 g of acetyl chloride. As reaction product one obtains 11.4 g (92.5% of theory) of ethyl N-acetyl-4-benzhydrylaminobutyrate as a viscous non-distillable oil. The saponification of this ester yields 9.2 g (88% of theory) of N-acetyl-4-benzhydrylaminobutyric acid (M.P. 173° to 174°).

EXAMPLE 21

N-(p-chloro)benzoyl-4-(1-phenylethylamino)butyric acid $R^1$=p-chlorophenyl, $R^2$=—H, $R^3$=—$CH_3$, $R^4$=phenyl, n=3

Analogously to Example 1, ethyl N-(p-chloro)benzoyl-4-(1-phenylethylamino)butyrate (viscous non-distillable oil) is obtained by reacting the reaction product of ethyl 4-bromobutyrate and dl-(1-phenylethyl)amine with p-chlorobenzoyl chloride, the saponification of which yields N-(p-chloro)benzoyl-4-(1-phenylethylamino)butyric acid (M.P. 110° to 112°).

EXAMPLE 22

N-(p-chloro)benzoyl-6-(1-phenylethylamino)caproic acid $R^1$=p-chlorophenyl, $R^2$=—H, $R^3$=—$CH_3$, $R^4$=phenyl n=5

Analogously to Example 1, ethyl N-(p-chloro)benzoyl-6-(1-phenylethylamino)caproate (viscous non-distillable oil) is obtained by reacting the reaction product of ethyl 6-bromocaproate and dl-(1-phenylethyl)amine with p-chlorobenzoyl chloride, the saponification of which yields N-(p-chloro)benzoyl-6-(1-phenylethylamino)caproic acid (M.P. 132° to 133°).

EXAMPLE 23

N-(p-chloro)benzoyl-4-homoveratrylaminobutyric acid $R^1$=p-chlorophenyl, $R^2$=$R^3$=—H, $R^4$=3,4-dimethoxybenzyl, n=3

Analogously to Example 1 ethyl N-(p-chloro)benzoyl-4-homoveratrylaminobutyrate (viscous non-distillable oil) is obtained by reacting the reaction product of ethyl 4-bromobutyrate and homoveratrylamine with p-chlorobenzoyl chloride, the saponification of which yields N-(p-chloro)-benzoyl-4-homoveratrylaminobutyric acid (M.P. 101° to 103°).

EXAMPLE 24

N-(p-chloro)benzoyl-4-[(1,2-diphenylethyl)amino]butyric acid $R^1$=p-chlorophenyl, $R^2$=—H, $R^3$=phenyl, $R^4$=benzyl, n=3

Analogously to Example 1, ethyl N-(p-chloro)benzoyl-4-[(1,2-diphenylethyl)amino]butyrate (viscous non-distillable oil) is obtained by reacting the reaction product of ethyl 4-bromobutyrate and 1,2-diphenylethylamine with p-chlorobenzoyl chloride, the saponification of which yields N-(p-chloro)benzoyl-4-[(1,2-diphenylethyl)amino]butyric acid (M.P. 121° to 122°).

EXAMPLE 25

Sodium N-(p-chloro)benzoyl-4-[(1,1,3,3-tetramethylbutyl)amino]butyrate 3.5 g of N-(p-chloro)benzoyl-4-[(1,1,3,3-tetramethylbutyl)amino]butyric acid is dissolved in 35 ml of boiling isopropyl alcohol, and to this there is added a hot solution of 0.23 g of sodium metal in 17.5 ml of isopropyl alcohol. After cooling, the solution is mixed with the same volume of diethyl ether. After several hours the crystalline sodium N-(p-chloro)benzoyl-4-[(1,1,3,3-tetramethylbutyl)amino]butyrate is filtered off, washed with isopropyl alcohol/ether and dried. The yield is almost quantitative. The salt melts without a sharp melting point at 187° to 190°.

EXAMPLE 26

N-(p-chloro)benzoyl-4-benzylaminobutyric acid (a) 4-benzylaminobutyronitrile 32.2 g of benzylamine, 14.8 g of 4-bromobutyronitrile and 30 ml of cyclohexane are stirred at room temperature for 12 hours. After the addition of diethyl ether the separated benzylamine hydrobromide is filtered off; the ether phase is washed with water, dried and concentrated by evaporation. The residue is distilled in vacuo to yield 11.5 g (66% of theory) of 4-benzylaminobutyronitrile (B.P. 114° to 120°/0.05 mm Hg).

(b) N-(p-chloro)benzoyl-4-benzylaminobutyronitrile 9.0 g of p-chlorobenzoyl chloride are added drop by drop at room temperature to a well-agitated mixture of 9.0 g of 4-benzylaminobutyronitrile, 6.7 g of ethyldiisopropylamine and 60 ml of benzene. After the addition has been completed, the stirring is continued for a further 2 hours. The reaction mixture is mixed with diethyl ether and cooled in iced water; the separated salt is filtered off. The filtrate is concentrated by evaporation, and the residue is recrystallized from ethyl acetate/petrol ether to yield 10.0 g (62% of theory) of N-(p- chloro)benzoyl-4-benzylaminobutyronitrile (M.P. 48° to 50°).

(c) N-(p-chloro)benzoyl-4-benzylaminobutyric acid

A solution of 0.5 g of N-(p-chloro)benzoyl-4-benzylaminobutyronitrile in 5 ml of absolute ethanol is saturated with hydrochloric acid gas at 0°. The solution is heated to 70° for 30 minutes and then concentrated by evaporation; the residue is mixed with water and extracted with diethyl ether. The residue of the ether extract is dissolved in 3 ml of benzene and mixed with a solution of 0.2 g of potassium hydroxide in 4 ml of ethanol. After standing for 2 days, the clear solution is concentrated by evaporation, and the residue is dissolved in water. The aqueous solution is first extracted with diethyl ether in order to remove impurities and is then acidified to a pH of 3 with dilute hydrochloric acid. The precipitate, which is deposited, is taken up in methylene chloride. The residue remaining after distilling off the methylene chloride is recrystallized from ethyl acetate/petrol ether to yield 0.4 g of N-(p-chloro)benzoyl-4-benzylaminobutyric acid (M.P. 101° to 102°), the IR and NMR spectra of which are identical with those of the substance produced according to Example 18.

EXAMPLE 27

N-(p-chloro)benzoyl-4-benzylaminobutyric acid (a) N-(p-chloro)benzoyl-4-aminobutyric acid To a solution of 10.3 g of 4-aminobutyric acid and 4.0 g of sodium hydroxide in 150 ml of water one adds slowly (drop by drop while stirring) at room temperature 17.5 g of p-chlorobenzoyl chloride. By adding (at the same time) dilute caustic soda solution, a pH of 7 to 8 is maintained. The aqueous solution is washed once with diethyl ether and then acidified with dilute hydrochloric acid. The resultant precipitate is taken up in methylene chloride; the residue remaining after evaporating off the solvent is washed with diethyl ether to obtain 21.5 g (89% of theory) of N-(p-chloro)benzoyl-4-aminobutyric acid (M.P. 107° to 108°).

(b) Benzyl N-(p-chloro)benzoyl-4-benzylaminobutyrate

In a solution of 7.25 g of N-(p-chloro)benzoyl-4-aminobutyric acid and 30 ml of dimethylsulfoxide there are suspended 4.0 g of potassium hydroxide powder. Into this suspension 9.1 g of benzyl chloride is slowly added (drop by drop) while stirring. The mixture is stirred at room temperature for a further 7 hours and then mixed with 100 ml of water. The reaction product is extracted with diethyl ether; the ether phase is washed with water, dried and concentrated by evaporation. The crude product is purified by chromatography over a silica gel column with methylene chloride as eluent to obtain 5.8 g (46% of theory) of benzyl N-(p-chloro)benzoyl-4-benzylaminobutyrate as a colorless viscous oil. The NMR spectrum confirms the structure.

(c) N-(p-chloro)benzoyl-4-benzylaminobutyric acid (cis form)

A solution of 2.0 g of benzyl N-(p-chloro)benzoyl-4-benzylaminobutyrate in 20 ml of benzene is mixed with a solution of 0.4 g of potassium hydroxide in 5 ml of ethanol. After allowing the resulting reaction mixture to stand for 20 hours at room temperature, the solvent is evaporated off, and the residue is dissolved in water. The aqueous solution is washed with diethyl ether and then acidified to a pH of 3 with dilute hydrochloric acid. The precipitate is filtered off and recrystallized from ethyl acetate/ligroin to obtain 1.35 g (86% of theory) of N-(p-chloro)benzoyl-4-benzylaminobutyric acid (M.P. 111° to 112°).

This is the cis form of the title compound. If one heats this for a few minutes to 230° and then recrystallizes once again from ethyl acetate/ligroin, one obtains crystals (with a melting point of 101° to 102°) which are identical with those of compounds produced according to Example 18 and Example 26.

EXAMPLE 28

N-(p-chloro)benzoyl-4-(tert.-butylamino)butyric acid (a) Ethyl N-(p-chloro)benzoyl-4-tert.butylamino)crotonate To a suspension of 8.4 g of ethyl-4-(tert.-butylamino)-crotonate hydrochloride in 70 ml of benzene there is added (drop by drop) while cooling 11.7 g of ethyldiisopropylamine and then 7.9 g of p-chlorobenzoyl chloride. The mixture is stirred at room temperature for a further 5 hours and filtered; the filtrate is concentrated by evaporation. The residue is recrystallized from ligroin to obtain 10.0 g of ethyl N-(p-chloro)-benzoyl-4-(tert.-butylamino)crotonate (M.P. 77° to 78°).

(b) N-(p-chloro)benzoyl-4-(tert.butylamino)crotonic acid

A solution of 8.0 g of ethyl N-(p-chloro)benzoyl-4-(tert.-butylamino)crotonate in 20 ml of benzene is mixed with a solution of 2.0 g of potassium hydroxide in 15 ml of ethanol. The mixture is stored at room temperature for 20 hours and then concentrated in a rotary evaporator. The evaporation residue is dissolved in water; the aqueous solution is washed with diethyl ether and then acidified with dilute hydrochloric acid. The precipitate, which is formed, is recrystallized from cyclohexane to obtain 6.1 g of N-(p-chloro)benzoyl-4-(tert.-butylamino)crotonic acid (M.P. 113° to 114°).

(c) N-(p-chloro)benzoyl-4-(tert.butylamino)butyric acid 5.0 g of N-(p-chloro)benzoyl-4-(tert.-butylamino)-crotonic acid is dissolved in 100 ml of tetrahydrofuran and, after the addition of 3.0 g of palladium charcoal (5% Pd), is treated in a hydrogenation apparatus with hydrogen. After the termination of the taking up of hydrogen, it is filtered off from the catalyst and the solvent evaporated. The residue is recrystallized from ethanol/water (1:1) to obtain 4.9 g of N-(p-chloro)benzoyl-4-(tert.-butylamino)butyric acid (M.P. 126° to 127°). The melting point of a mixture with the substance produced according to Example 3 shows no depression.

EXAMPLE 29

N-(p-chloro)benzoyl-4-[(p-methoxybenzyl)amino]-butyric acid $R^1$=p-chlorophenyl, $R^2=R^3$=—H, $R^4$=p-methoxyphenyl, n=3

Analogously to Example 18 1-(p-methoxybenzyl)-pyrrolidone is heated with sodium hydroxide solution and then reacted with p-chlorobenzoyl chloride to obtain N-(p-chloro)benzoyl-4-[(p-methoxybenzyl)amino]-butyric acid, M.P. 128.5° to 129.5°.

EXAMPLE 30

N-(p-chloro)benzoyl-5-benzylaminovaleric acid $R^1$=p-chlorophenyl, $R^2=R^3=$—H, $R^4$=phenyl, n=4

Analogously to Example 18, 1-benzyl-δ-valerolactam is heated with sodium hydroxide solution and then reacted with p-chlorobenzoyl chloride to obtain N-(p-chloro)benzoyl-5-benzylaminovaleric acid, M.P. 93° to 94°.

EXAMPLE 31

N-(m-trifluoromethyl)benzoyl-4-[(1,1,3,3-tetramethylbutyl)amino]butyric acid $R^1$=α,α,α-trifluoro-m-tolyl, $R^2=R^3=$—CH$_3$, $R^4=$—CH$_2$—C(CH$_3$)$_3$, n=3

Analogously to Example 1, ethyl N-(m-trifluoromethylbenzoyl)-4-[(1,1,3,3-tetramethylbutyl)amino]butyrate is obtained as a viscous oil by reacting the reaction product of ethyl 4-bromobutyrate and 1,1,3,3-tetramethylbutylamine with m-trifluoromethylbenzoyl chloride, the saponification of which yields N-(m-trifluoromethyl)benzoyl-4-[(1,1,3,3-tetramethylbutyl)amino]butyric acid (M.P. 86° to 87°).

EXAMPLE 32

N-crotonoyl-4-[(1,1,3,3-tetramethylbutyl)amino]-butyric acid $R^1=$—CH=CH—CH$_3$, $R^2=R^3=$—CH$_3$, $R^4=$—CH$_2$—C(CH$_3$)$_3$, n=3

Analogously to Example 1, ethyl N-crotonoyl-4-[(1,1,3,3-tetramethylbutyl)amino]butyrate is obtained as a viscous oil by reacting the reaction product of ethyl 4-bromobutyrate and 1,1,3,3-tetramethylbutylamine with crotonic acid chloride, the saponification of which yields N-crotonoyl-4-[(1,1,3,3-tetramethylbutyl)amino]-butyric acid (M.P. 92° to 93°).

EXAMPLE 33

N-propionyl-4-benzhydrylaminobutyric acid $R^1=$—C$_2$H$_5$, $R^2=$—H, $R^3=R^4$=phenyl, n=3

(a) Ethyl N-propionyl-4-benzhydrylaminobutyrate

Analogously to Example 19, 9.0 g of ethyl 4-benzhydrylaminobutyrate and 4.3 g of diisopropylethylamine in 100 ml of benzene are reacted with 3.1 g of propionyl chloride. The reaction product is recrystallized from ethyl acetate/ligroin (1:1) to obtain 9.9 g (92.5% of theory) of ethyl N-propionyl-4-benzhydrylaminobutyrate (M.P. 83° to 85°).

(b) N-propionyl-4-benzhydrylaminobutyric acid

The saponification of 9.3 g of ethyl N-propionyl-4-benzhydrylaminobutyrate in 100 ml of benzene with a solution of 2.2 g of potassium hydroxide in 20 ml of ethanol (analogously to Example 19) yields [after recrystallization of the reaction product from ethyl acetate/ligroin (1:1)] 7.8 g (91% of theory) of N-propionyl-4-benzhydrylaminobutyric acid, M.P. 151.5° to 152.5°.

EXAMPLE 34

N-(5-chloro-2-methoxybenzoyl)-4-benzhydrylaminobutyric acid $R^1$=5-chloro-2-methoxyphenyl, $R^2=$—H, $R^3=R^4$=phenyl, n=3

Analogously to Example 19, 8.9 g of ethyl 4-benzhydrylaminobutyrate and 4.3 g of ethyl diisopropylamine are dissolved in 80 ml of benzene and reacted with a solution of 6.8 g of 5-chloro-2-methoxybenzoic acid chloride in 20 ml of benzene. As reaction product one obtains 13.8 g (99% of theory) of ethyl N-(5-chloro-2-methoxybenzoyl)-4-benzhydrylaminobutyrate as a viscous non-distillable oil. The saponification of this ester yields 11.1 g (85.6% of theory) of N-(5-chloro-2-methoxybenzoyl)-4-benzhydrylaminobutyric acid (M.P. 176° to 178°).

EXAMPLE 35

N-acetyl-6-benzhydrylaminocaproic acid $R^1=$—CH$_3$, $R^2=$—H, $R^3=R^4$=phenyl, n=5

(a) Ethyl 6-benzhydrylaminocaproate 22.3 g of ethyl 6-bromocaproate, 55 g of benzhydrylamine and 30 ml of cyclohexane are stirred at room temperature for 20 days. Preparation analogously to Example 19 yields 22.5 g (69% of theory) of ethyl-6-benzhydrylaminocaproate [B.P. 162° to 167° (0.02 mm Hg)].

(b) N-acetyl-6-benzhydrylaminocaproic acid

Analogously to Example 19, 8 g of ethyl 6-benzhydrylaminocaproate and 3.5 g of ethyl diisopropylamine are dissolved in 100 ml of benzene and reacted with 2.1 g of acetyl chloride. As reaction product one obtains 9 g of ethyl N-acetyl-6-benzhydrylaminocaproate as a viscous non-distillable oil. The saponification of this ester gives 7.3 g (87.5%) of N-acetyl-6-benzhydrylaminocaproic acid (M.P. 119° to 120°).

EXAMPLE 36

N-isobutyryl-6-benzhydrylaminocaproic acid $R^1=$—CH(CH$_3$)$_2$, $R^2=$—H, $R^3=R^4$=phenyl, n=5

Analogously to Example 19, 7 g of ethyl 6-benzhydrylaminocaproate and 3.1 g of ethyl diisopropylamine are dissolved in 100 ml of benzene and reacted with 2.5 g of isobutyryl chloride. As reaction product one obtains 7.8 g of ethyl N-isobutyryl-6-benzhydrylaminocaproate as a viscous non-distillable oil. The saponification of this ester yields 6.1 g (77%) of N-isobutyryl-6-benzhydrylaminocaproic acid (M.P. 106° to 107°).

EXAMPLE 37

N-acetyl-5-benzhydrylaminovaleric acid $R^1=$—CH$_3$, $R^2=$—H, $R^3=R^4$=phenyl, n=4

(a) Ethyl 5-benzhydrylaminovalerate 25.1 g of ethyl 5-bromovalerate, 66 g of benzhydrylamine and 30 ml of cyclohexane are stirred at room temperature for 15 days. Processing analogously to Example 19 yields 23.4 (62.6%) of ethyl 5-benzhydrylaminovalerate [B.P. 158° to 163° (0.01 mm Hg)].

(b) N-acetyl-5-benzhydrylaminovaleric acid

Analogously to Example 19, 9 g of ethyl 5-benzhydrylaminovalerate and 4.1 g of ethyl diisopropylamine are dissolved in 100 ml of benzene and reacted with 2.5 g of acetyl chloride. As reaction product one obtains 10 g of ethyl N-acetyl-5-benzhydrylaminovalerate as a viscous non-distillable oil. The saponification of this ester gives 7.4 g (78.7%) of N-acetyl-5-benzhydrylaminovaleric acid (M.P. 135° to 136°).

EXAMPLE 38

N-crotonoyl-5-benzhydrylaminovaleric acid $R^1 = -CH=CH-CH_3$, $R^2 = -H$, $R^3 = R^4 =$ phenyl, $n = 4$ Analogously to Example 19, 7 g of ethyl 5-benzhydrylaminovalerate and 3.2 g of ethyldiisopropylamine are dissolved in 100 ml of benzene and reacted with 2.6 g of crotonyl chloride. As reaction product one obtains 8.5 g of ethyl N-crotonoyl-5-benzhydrylaminovalerate as a viscous non-distillable oil. The saponification of this ester yields 6 g (76%) of N-crotonoyl-5-benzhydrylaminovaleric acid (M.P. 88° to 89°).

EXAMPLE 39

N-(p-chloro)benzoyl-4-[L(−)-(α-methylbenzyl)amino]-butyric acid $R^1 =$ p-chlorophenyl, $R^2 = -H$, $R^3 = -CH_3$, $R^4 =$ phenyl, $n = 3$ Analogously to Example 1, ethyl N-(p-chloro)benzoyl-4-L(−)-(α-methylbenzylamino)butyrate (viscous, non-distillable oil) is obtained by reacting the reaction product of ethyl 4-bromobutyrate and L(−)-α-methylbenzylamine with p-chlorobenzoylchloride, the saponification of which gives N-(p-chloro)benzoyl-4-[L(−)-(α-methylbenzyl)amino]butyric acid (M.P. 93° to 94°; $[\alpha]_D - 142.5°$).

EXAMPLE 40

N-salicyloyl-4-benzhydrylaminobutyric acid $R^1 =$ o-hydroxyphenyl, $R^2 = -H$, $R^3 = R^4 =$ phenyl, $n = 3$ 13.3 g of ethyl 4-benzhydrylaminobutyrate (Example 19a) and 6.4 g of ethyldiisopropylamine are dissolved in 80 ml of benzene. A solution of 9.8 g of 0-acetylsalicycloyl chloride in 20 ml of benzene is added dropwise thereto while cooling and stirring. The mixture is mixed with diethyl ether after a further 4 hours; the precipitated salt is filtered off; and the filtrate is concentrated by evaporation. The evaporation residue is purified by chromatography over a silica gel column with methylene chloride as eluent to obtain 18.6 g (90.5 percent of theory) of ethyl N-(o-acetoxy)benzoyl-4-benzhydrylaminobutyrate in the form of a colorless, viscous, non-distillable oil. This oil is dissolved in 200 ml of benzene. A solution of 5.7 g of potassium hydroxide in 30 ml of ethanol is added. The reaction mixture is kept for 20 hours at room temperature, diluted with diethyl ether and then extracted with water. The aqueous phase is acidified with dilute hydrochloric acid. The resulting precipitate is filtered off, dried and recrystallized from ethyl acetate/ligroin to obtain 13.0 g (82.5 percent of theory) of N-salicyloyl-4-benzhydrylaminobutyric acid (M.P. 162° to 163°).

EXAMPLE 41

Ampoules with 600 mg of N-(p-chlorobenzoyl)-4-(1-phenylethylamino)butyric acid, size of batch 250 kg

| | |
|---|---|
| N-(p-chlorobenzoyl)-4-(1-phenyl-ethylamino)butyric acid | 15 kg |
| Caustic soda solution (10% by wt. NaOH) | approx. 17 kg |
| 1,2-propyleneglycol | 25 kg |
| Sodium pyrosulfite | 0.0625 kg |
| Double-distilled water | to make up to 250 kg |

25.0 kg of 1,2-propyleneglycol and 150.0 kg of water are placed in a vessel, 15.000 kg of N-(p-chlorobenzoyl)-4-(1-phenylethylamino)butyric acid are added and then there is added slowly, while stirring, caustic soda solution. When everything has dissolved, the resulting solution is adjusted with caustic soda solution of a pH of from 7.5 to 8.0. Sodium pyrosulfite is added and the mixture stirred until everything has dissolved. It is made up to 250 kg with the rest of the water. The solution is packed in 10-ml ampoules and sterilized in an autoclave for 30 minutes at 120° C.

EXAMPLE 42

Ampoules containing 600 mg of N-(p-chloro)benzoyl)-4-benzhydrylaminobutyric acid, size of batch 250 kg.

| | |
|---|---|
| N-(p-chloro)benzoyl-4-benzhydryl-aminobutyric acid | 15 kg |
| Caustic soda solution (10% by wt. NaOH) | approx. 15 kg |
| 1,2-propyleneglycol | 50 kg |
| Double-distilled water | to make up to 250 kg |

50 kg of 1,2-propyleneglycol and 150 kg of water are placed in a vessel. Then N-(p-chloro)benzoyl-4-benzhydrylaminobutyric acid is added while stirring. 15 kg of caustic soda solution are added, and the resulting mixture is then adjusted to a pH of 8.0. This is made up to 250 kg with water. The solution is packed into 10-ml ampoules and sterilized in an autocalve for 30 minutes at 120°.

EXAMPLE 43

Tablets containing 50 mg of N-(p-chloro)benzoyl-4-benzylaminobutyric acid

| | |
|---|---|
| N-(p-chloro)benzoyl-4-benzylaminobutyric acid | 25 kg |
| Lactose | 35 kg |
| Maize starch | 26 kg |
| Polyvinylpyrrolidone (mol. wt. approx. 25,000) | 2.5 kg |
| Carboxymethylcellulose | 8 kg |
| Talcum | 2.5 kg |
| Magnesium stearate | 1 kg |
| | 100 kg |

The N-(p-chloro)benzoyl-4-benzylaminobutyric acid, the lactose and the maize starch are granulated with polyvinylpyrrolidone in approximately 6 liters of water. The granulate is sieved through a sieve with a mesh width of 1.25 mm and, after drying, the carboxymethylcellulose, the talcum and the magnesium stearate are added. The dry granulate is pressed into tablets with a diameter of 8 mm, a weight of 250 mg and a hardness of 5 to 6 kg.

In a similar way tablets are produced with N-acetyl-4-benzhydrylaminobutyric acid or N-(p-chloro)benzoyl-4-(1-phenylethylamino)butyric acid.

EXAMPLE 44

Tablets containing 100 mg of N-(p-chloro)benzoyl-4-[(1,2-diphenylethyl)amino]butyric acid

| | |
|---|---|
| N-(p-chloro)benzoyl-4-[(1,2-diphenyl-ethyl)amino]butyric acid | 40 kg |
| Lactose | 24 kg |
| Maize starch | 16 kg |
| Polyvinylpyrrolidone (mol. wt. approx. 25,000) | 4 kg |
| Carboxymethylcellulose | 10 kg |

-continued

| | |
|---|---|
| Talcum | 4 kg |
| Magnesium stearate | 2 kg |
| | 100 kg |

The N-(p-chloro)benzoyl-4-[(1,2-diphenylethyl)-amino]butyric acid, the lactose and the maize starch are granulated with the polyvinylpyrrolidone is approximately 5.5 liters of water and forced through a sieve with a mesh width of 1.25 mm. After drying, the carboxymethylcellulose, the talcum and the magnesium stearate are added. The granulate is pressed on an eccentric tabletting machine into tablets of 9 mm. diameter, 250 mg weight and a hardness of from 4 to 5 kg.

In a similar manner N-(p-chloro)benzoyl-6-(1-phenylethylamino)caporic acid or N-(p-chloro)benzoyl-4-(1-adamantyl)aminobutyric acid is pressed into tablets with and active principle content of 100 mg.

EXAMPLE 45

Tablets containing 300 mg of N-(p-chloro)benzoyl-4-cyclooctylaminobutyric acid.

| | |
|---|---|
| N-(p-chloro)benzoyl-4-cyclooctylaminobutyric acid | 60 kg |
| Lactose | 12 kg |
| Maize starch | 8 kg |
| Polypyrrolidone (mol. wt. approx. 25,000) | 4 kg |
| Carboxymethylcellulose | 10 kg |
| Talcum | 4 kg |
| Magnesium stearate | 2 kg |
| | 100 kg |

N-(p-chloro)benzoyl-4-cyclooctylaminobutyric acid, the lactose and the maize starch are granulated with the polyvinylpyrrolidone in approximately 6 liters of water and pressed through a sieve with a mesh width of 1.25 mm. After drying the carboxymethylcellulose, the talcum and the magnesium stearate are added. The granulate is pressed on a rotary pelleting machine into tablets with a diameter of 11 mm, a weight of 500 mg and a hardness of 6 to 7 kg.

EXAMPLE 46

10,000 capsules with an active principle content of 50 mg are produced from the following ingredients:

| | |
|---|---|
| 500 g of N-(p-chloro)benzoyl-4-benzhydrylaminobutyric acid | |
| 495 g of microcrystalline cellulose | |
| 5 g of amorphous silica | |
| 1000 g | |

The active principle in finely-powdered form, the cellulose and the silica are thoroughly mixed and packed into hard gelatin capsules of size 4.

Pharmacology

Acylhydrocarbylamino acids of formulae Ia and Ib and their pharmacologically-acceptable salts exert a marked influence on the pancreatic secretion of narcotized rats; they influence the bile secretion of narcotized rats and exert an antihepatotoxic activity on wakeful rats, in which they are found to be superior to known commercial preparations, such as Piprozolin.

In the tablets which follow the compounds investigated are characterized by a serial number which is allocated as follows:

| Serial No. | Name of Compound |
|---|---|
| 1 | Piprozoline |
| 2 | N-(p-chloro)benzoyl-4-(tert.-butylamino)-butyric acid |
| 3 | N-(p-chloro)benzoyl-4-[(2-methyl-3-butyn-2-yl)-amino]butyric acid |
| 4 | N-(p-chloro)benzoyl-4-[(3-ethyl-1-pentyn-3-yl)-amino]butyric acid |
| 5 | N-(p-chloro)benzoyl-4-[(1-ethynylcyclohexyl-1)-amino]butyric acid |
| 6 | N-(p-chloro)benzoyl-4-(1-adamantyl)aminobutyric acid |
| 7 | N-(p-chloro)benzoyl-4-[(1,1,3,3-tetramethyl-butyl)amino]butyric acid |
| 8 | N-acetyl-4-[(1-ethynylcyclohexyl-1)-amino]-butyric acid |
| 9 | N-(p-chloro)benzoyl-4-homoveratrylamino-butyric acid |
| 10 | N-(p-chloro)benzoyl-4-(1-phenylethylamino)-butyric acid |
| 11 | N-(2,4-dichloro)benzoyl-4-[(1,1-dimethylpropyl)-amino]butyric acid |
| 12 | N-(p-chloro)benzoyl-4-benzhydrylaminobutyric acid |
| 13 | N-(p-chloro)benzoyl-6-(1-phenylethylamino)-caproic acid |
| 14 | N-acetyl-4-benzhydrylaminobutyric acid |
| 15 | N-(p-chloro)benzoyl-4-benzylaminobutyric acid |
| 16 | N-(p-fluoro)benzoyl-4-(1,1,3,3-tetramethyl-butyl)aminobutyric acid |
| 17 | N-(p-chloro)benzoyl-4-[(1,2-diphenylethyl)-amino]butyric acid |
| 18 | N-(p-chloro)benzoyl-4-cyclooctylaminobutyric acid |

Table I reflects data from investigations of the pancreatic secretion of narcotized rats after intraduodenal application ($ED_{50}$) and the lethal action on the mouse ($LD_{50}$) after intraperitoneal application of representative compounds of formulae Ia and Ib according to the invention and also the therapeutic quotient ($TQ = LD_{50}/DE_{50}$).

TABLE I

Pancreatic Secretion, Toxicity and Therapeutic Quotient

| Serial No. | Toxicity $LD_{50}$ (mg/kg) (mouse, i.p.) | Pancreatic Secretion $ED_{50}^+$ (mg/kg) (rat, i.d.) | TQ ($LD_{50}/ED_{50}$) |
|---|---|---|---|
| 1 | 1070++ | 35 | 31 |
| 5 | 190 | 2 | 95 |
| 6 | 200 | 1 | 200 |
| 7 | 220 | 2 | 110 |
| 8 | >>1000 | 10 | >>100 |
| 9 | 780 | 5 | 156 |
| 10 | 1200 | ~20 | ~60 |
| 12 | 250 | ~0.1 | ~2500 |
| 13 | 220 | 2 | 110 |
| 14 | 1100 | ~5 | ~220 |
| 15 | 350 | 1.5 | 233 |
| 16 | 400 | ~10 | ~40 |
| 17 | 160 | ~1 | ~160 |
| 18 | 150 | 2.5 | 60 |

$^+ED_{50}$ = dose which brings about an increase in the pancreatic secretion (liquid volume; 30-min. fraction) by a maximum of 50%.
$^{++}LD_{50}$ (p.o.) cited from Herrmann et al, Arzneim.-Forsch. 27 (1977) 467.

Table II reflects data from investigations of the bile secretion (choleresis) of narcotized rats after intraduodenal application ($ED_{50}$) and lethal action on the mouse ($LD_{50}$) after intraperitoneal application of representative compounds of formula Ib according to the invention and also the therapeutic quotient ($TQ = LD_{50}/ED_{50}$).

TABLE II

Bile Secretion, Toxicity and Therapeutic Quotient

| Serial No. | Toxicity LD$_{50}$ (mg/kg) (mouse, i.p.) | Bile Secretion ED$_{50}$+++(mg/kg) (rat, i.d.) | TQ (LD$_{50}$/ED$_{50}$) |
|---|---|---|---|
| 1 | 1070++ | 40 | 27 |
| 2 | 850 | 15 | 57 |
| 3 | >1000 | 25 | >40 |
| 4 | 200 | ~5 | ~40 |
| 5 | 190 | 6 | 32 |
| 9 | 780 | 18 | 43 |
| 10 | 1200 | ~15 | ~80 |
| 11 | 190 | 6 | 32 |
| 14 | 1100 | 5 | 220 |
| 16 | 400 | 7 | 57 |
| 17 | 160 | 5 | 32 |

+++ED$_{50}$ = the dose which brings about an increase in the bile secretion (liquid volume; 30-min. fraction) by a maximum of 50%
++LD$_{50}$ (p.o.) cited from Herrmann et al, Arzneim.-Forsch., 27 (1977) 467.

Table III reflects data from investigations on the antihepatotoxic action (ED$_{50}$) of compounds of formula Ib according to the invention after oral application on wakeful rats and the lethal action after intraperitoneal application on the mouse (LD$_{50}$), as well as the therapeutic quotient (TQ=LD$_{50}$/ED$_{50}$).

TABLE III

Antihepatotoxic Effect, Toxicity and Therapeutic Quotient

| Serial No. | Toxicity LD$_{50}$ (mg/kg) (mouse, i.p.) | Antihepatotoxic Effect ED$_{50}$++++ (mg/kg) (rat, p.o.) | TQ (LD$_{50}$/ED$_{50}$) |
|---|---|---|---|
| 1 | 1070++ | >300 | <3.6 |
| 3 | >1000 | 100 | >10 |
| 9 | 780 | 100 | 7.8 |
| 10 | 1200 | ~10 | ~120 |
| 12 | 250 | 10 | 25 |
| 14 | 1100 | 10 | 110 |
| 17 | 160 | 10 | 16 |
| 18 | 150 | 8 | 18.8 |

++++ED$_{50}$ = the dose which shortens the hexobarbital narcosis by 50% of rats with liver damage from CCl$_4$.
++LD$_{50}$ (p.o.) cited from Hermann et al., Arzneim.-Forsch., 27 (1977) 467.

EXAMPLE 47

4-[p-chloro-N-(biphenyl-2-yl)benzamido]butyric acid

R$^1$=p-chlorophenyl, R=biphenyl-2-yl, n=3

(a) Ethyl 4-(biphenyl-2-yl)aminobutyrate 30.0 g of 2-aminobiphenyl, 23.4 g of ethyl diisopropylamine and 35.4 g of ethyl 4-bromobutyrate are heated together to 150° for 3 hours while stirring. After cooling, the reaction product is stirred with diethyl ether, the precipitated salt is filtered off, and the residue (remaining after evaporating off the ether) is recrystallized from isopropyl alcohol to obtain 32.0 g (63.7% of theory) of ethyl 4-(biphenyl-2-yl)aminobutyrate, MP 60° to 62°.

(b) Ethyl 4-[p-chloro-N-(biphenyl-2-yl)benzamido]butyrate 9.8 g of p-chlorobenzoyl chloride is added drop by drop at room temperature (while stirring and within 30 minutes) to a solution of 16.0 g of ethyl 4-(biphenyl-2-yl)-aminobutyrate and 7.3 g of ethyl diisopropylamine in 70 ml of benzene. After a further hour, the precipitate is filtered off, the filtrate is evaporated, and the evaporation residue is recrystallized from cyclohexane to obtain 18.0 g (75.6% of theory) of ethyl 4-[(p-chloro-N-(biphenyl-2-yl)benzamido]butyrate, MP 100° to 102°.

(c) 4-[p-chloro-N-(biphenyl-2-yl)benzamido]butyric acid 15.0 g of ethyl 4-[p-chloro-N-(biphenyl-2-yl)benzamido]-butyrate is dissolved in 100 ml of benzene and, after the addition thereto of a solution of 2.8 g of potassium hydroxide in 20 ml of ethanol, is then stirred at room temperature for 5 hours. The solvent is then distilled off in vacuo, and the obtained residue is dissolved in water. The resulting aqueous solution is acidified with dilute hydrochloric acid, and the precipitate, which separates out, is taken up in methylene chloride. The residue remaining, after drying and distilling off the methylene chloride, is recrystallized from an ethanol/water mixture (2:1) to obtain 10.1 g (72.1% of theory) of 4-[p-chloro-N-(biphenyl-2-yl)benzamido]butyric acid, MP 135° to 137°.

EXAMPLE 48

4-[m-trifluoromethyl-N-(biphenyl-2-yl)benzamido]-butyric acid

R$^1$=α,α,α-trifluoro-m-tolyl, R=biphenyl-2-yl, n=3

(a) Ethyl 4-[m-trifluoromethyl-N-(biphenyl-2-yl)benzamido]butyrate

Analogously to Example 47b, 11.8 g of ethyl 4-(biphenyl-2-yl)aminobutyrate and 5.4 g of ethyldiisopropylamine are reacted in 70 ml of benzene with 8.7 g of m-trifluoromethylbenzoyl chloride. The reaction product is recrystallized from a mixture of isopropyl alcohol and water (1:1) to obtain 16.0 g (84.4% of theory) of ethyl-4-[m-trifluoromethyl-N-(biphenyl-2-yl)benzamido]-butyrate, MP 65° to 67°.

(b) 4-[m-trifluoromethyl-N-(biphenyl-2-yl)benzamido]-butyric acid 16.0 g of ethyl-4-[m-trifluoromethyl-N-(biphenyl-2-yl)-benzamido]butyrate in 50 ml of benzene are mixed with a solution of 3.4 g of potassium hydroxide in 25 ml of ethanol and stirred at room temperature for 8 hours. When further processed analogously to Example 47c, 13.7 g (91.3% of theory) of 4-[m-trifluoromethyl-N-(biphenyl-2-yl)benzamido]butyric acid, MP 156° to 157°, are obtained.

EXAMPLE 49

4-[p-fluoro-N-(biphenyl-2-yl)benzamido]butyric acid

R$^1$=p-fluorophenyl, R=biphenyl-2-yl, n=3

(a) Ethyl 4-[p-fluoro-N-(biphenyl-2-yl)benzamido]butyrate

Analogously to Example 47b), 10.0 g of ethyl 4-(biphenyl-2-yl)aminobutyrate and 4.6 g of ethyldiisopropylamine in 50 ml of benzene are reacted with 5.6 g of p-fluorobenzoyl chloride. The reaction product is recrystallized from cyclohexane to obtain 12.1 g (84.6% of theory) of ethyl 4-[p-fluoro-N-(biphenyl-2-yl)-benzamido]butyrate, MP 83° to 84°.

(b) 4-[p-fluoro-N-(biphenyl-2-yl)benzamido]butyric acid 11.2 g of ethyl 4-[p-fluoro-N-(biphenyl-2-yl)benzamido]-butyrate in 50 ml of benzene is mixed with a solution of 2.2 g of potassium hydroxide in 20 ml of ethanol and stirred at room temperature for 8 hours.

When processed analogously to Example 47c), 7.1 g (71.7% of theory) of 4-[p-fluoro-N-(biphenyl-2-yl)benzamido]butyric acid, MP 120° to 122°, are obtained.

EXAMPLE 50

4-[5-chloro-2-methoxy-N-(biphenyl-2-yl)benzamido]butyric acid $R^1$ = 5-chloro-2-methoxyphenyl, R = biphenyl-2-yl, n = 3

Analogously to Example 47, 10.0 g of ethyl 4-(biphenyl-2-yl)aminobutyrate and 4.6 g of ethyldiisopropylamine in 50 ml of benzene are reacted with a solution of 7.3 g of 5-chloro-2-methoxybenzoyl chloride in 20 ml of benzene to obtain, as reaction product, 15.0 g (94.1% of theory) of ethyl 4-[5-chloro-2-methoxy-N-(biphenyl-2-yl)benzamido]butyrate as a viscous non-distillable oil. The saponification of this ester yields 12.4 g (88% of theory) of 4-[5-chloro-2-methoxy-N-(biphenyl-2-yl)benzamido-9 butyric acid, MP 160° to 162°.

EXAMPLE 51

4-[N-(biphenyl-2-yl)acetamido]butyric acid $R^1$ = —$CH_3$, R = biphenyl-2-yl, n = 3

Analogously to Example 47, 16.0 g of ethyl 4-(biphenyl-2-yl)aminobutyrate and 7.3 g of ethyldiisopropylamine in 70 ml of benzene are reacted with 4.4 g of acetyl chloride to obtain, as reaction product, 14.0 g (76.2% of theory) of ethyl 4-[N-(biphenyl-2-yl)acetamido]butyrate as a viscous non-distillable oil. The saponification of this ester and recrystallization of the crude product obtained from isopropyl alcohol yields 10.1 g (79.0% of theory) of 4-[N-(biphenyl-2-yl)acetamido]butyric acid, MP 124° to 125°.

EXAMPLE 52

4-[N-(biphenyl-2-yl)crotonoylamido]butyric acid

Analogously to Example 47, 10.0 g of ethyl 4-(biphenyl-2-yl)aminobutyrate and 4.6 g of ethyldiisopropylamine in 70 ml of benzene are reacted with 3.8 g of crotonyl chloride to obtain, as reaction product, 10.1 g (81.5% of theory) of ethyl 4-[N-(biphenyl-2-yl)crotonoylamido]butyrate as a viscous non-distillable oil. The saponification of this ester and recrystallization of the crude product obtained from isopropyl alcohol yields 5.1 g (55% of theory) of 4-[N-(biphenyl-2-yl)crotonoylamido]butyric acid, MP 127° to 128°.

EXAMPLE 53

5-[(p-chloro-N-(biphenyl-2-yl)benzamido]valeric acid $R^1$ = p-chlorophenyl, R = biphenyl-2-yl, n = 4

50.0 g of 2-aminobiphenyl, 38.2 g of ethyldiisopropylamine and 61.9 g of ethyl 5-bromovalerate are reacted analogously to Example 47a) to obtain 80.0 g of ethyl 5-(biphenyl-2-yl)aminovalerate as a non-crystallizing oil.

30.0 g of this ester is reacted, analogously to Example 47b), with 13.1 g of ethyldiisopropylamine and 17.1 g of p-chlorobenzoyl chloride in 70 ml of benzene; the ethyl 5-[p-chloro-N-(biphenyl-2-yl)benzamido]valerate obtained as an oily intermediate product is then saponified analogously to Example 47c) to obtain 22.1 g (53.7% of theory) of 5[p-chloro-N-(biphenyl-2-yl)benzamido]valeric acid, MP 170° to 173°.

EXAMPLE 54

5-[o-hydroxy-N-(biphenyl-2-yl)benzamido]valeric acid $R^1$ = o-hydroxyphenyl, R = biphenyl-2-yl, n = 4

15.0 g of ethyl 5-(biphenyl-2-yl)aminovalerate is reacted, analogously to Example 47b), with 6.6 g of ethyldiisopropylamine and 10.0 g of o-acetoxybenzoylchloride in 70 ml of benzene to obtain, as reaction product, 17.0 g (73.4% of theory) of ethyl 5-[o-acetoxy-N-(biphenyl-2-yl)-benzamido]valerate as a viscous non-distillable oil. The saponification of this ester yields 9.1 g (63.2% of theory) of 5-[o-hydroxy-N-(biphenyl-2-yl)benzamido]valeric acid, MP 138° to 139°.

EXAMPLE 55

6-[p-chloro-N-(biphenyl-2-yl)benzamido]caproic acid $R^1$ = p-chlorophenyl, R = biphenyl-2-yl, n = 5

20.0 g of 2-aminobiphenyl, 15.3 g of ethyldiisopropylamine and 26.3 g of ethyl 6-bromocaproate are reacted, analogously to Example 47a), to obtain 36.0 g of ethyl 6-(biphenyl-2-yl)aminocaproate as a non-crystallizing oil. 18.0 g of this ester are reacted, analogously to Example 47b), with 7.5 g of ethyldiisopropylamine and 10.1 g of p-chlorobenzoyl chloride in 70 ml of benzene. The resulting reaction product is purified chromatographically over a silica gel column (eluent: methylene chloride) to obtain 11.5 g (44.2% of theory) of ethyl 6-[p-chloro-N-(biphenyl-2-yl)benzamido]caproate as a viscous non-distillable oil. Saponification of this ester yields 8.1 g (75.1% of theory) of 6-[p-chloro-N-(biphenyl-2-yl)benzamido]caproic acid, MP 93° to 95°.

EXAMPLE 56

6-[5-chloro-2-methoxy-N-(biphenyl-2-yl)benzamido]caproic acid 8.0 g of ethyl 6-(biphenyl-2-yl)aminocaproate and 3.3 g of ethyldiisopropylamine in 50 ml of benzene are reacted with a solution of 5.3 g of 5-chloro-2-methoxybenzoyl chloride in 20 ml of benzene, analogously to Example 47a), to obtain, as reaction product, 11.1 g (90% of theory) of ethyl 6-[5-chloro-2-methoxy-N-(biphenyl-2-yl)benzamido]caproate as a viscous non-distillable oil. The saponification of this ester yields 7.0 g (67% of theory) of 6-[5-chloro-2-methoxy-N-(biphenyl-2-yl)benzamido]-caproic acid, MP 164° to 165°.

EXAMPLE 57

6-[N-(biphenyl-2-yl)isobutyramido]caproic acid $R^1$ = —$CH(CH_3)_2$, R = biphenyl-2-yl, n = 5

Analogously to Example 56, 10.0 g of ethyl 6-(biphenyl-2-yl)aminocaproate, 4.2 g of ethyldiisopropylamine and 3.4 isobutyryl chloride in 70 ml of benzene yields 8.9 g (72.6% of theory) of ethyl 6-[N-(biphenyl-2-yl)isobutyramido]-caproate as a viscous non-distillable oil. The saponification of this ester yields 6.1 g (74% of theory) of 6-[N-(biphenyl-2-yl)isobutyramido]caproic acid, MP 120° to 121°.

EXAMPLE 58

4-[p-chloro-N-(biphenyl-4-yl)benzamido]butyric acid $R^1$ = p-chlorophenyl, R = biphenyl-4-yl, n = 3

(a) Ethyl 4-(biphenyl-4-yl)aminobutyrate 24.0 g (57.3% of theory) of ethyl 4-(biphenyl-4-yl)-aminobutyrate, MP 82° to 84°, are obtained analogously to Example 47a), from 25.0 g of 4-aminobiphenyl, 19.2 g of ethyldiisopropylamine and 28.9 g of ethyl 4-bromobutyrate.

(b) 4-[p-chloro-N-(biphenyl-4-yl)benzamido]butyric acid

Analogously to Example 47b), 10.0 g of ethyl 4-(biphenyl-4-yl)aminobutyrate and 4.6 g of ethyldiisopropylamine in 70 ml of benzene are reacted with 6.2 g of p-chlorobenzoyl chloride to obtain 9.4 g (62.9% of theory) of ethyl 4-[p-chloro-N-(biphenyl-4-yl)benzamido]butyrate as a viscous non-distillable oil. Saponification of this ester, analogously to Example 47c), yields 7.0 g (79.7% of theory) of 4-[p-chloro-N-(biphenyl-4-yl)-benzamido]butyric acid, MP 192° to 194°.

EXAMPLE 59

4-[p-chloro-N-(6-methoxy-biphenyl-3-yl)benzamido]-butyric acid $R^1$ = p-chlorophenyl, R = 6-methoxybiphenyl-3-yl, n = 3

(a) Ethyl 4-(6-methoxy-biphenyl-3-yl)aminobutyrate 29.5 g of 5-amino-2-methoxybiphenyl, 19.2 g of ethyldiisopropylamine and 28.9 g of ethyl 4-bromobutyrate are heated together (while stirring) for 4 hours at 125°. After cooling, the resulting reaction product is stirred with diethyl ether and filtered from the precipitated salt. The residue (remaining after evaporating off the ether) is recrystallized from isopropyl alcohol to obtain 22.5 g (48.5% of theory) of ethyl 4-(6-methoxybiphenyl-3-yl)amiobutyrate, MP 71° to 72.

(b) 4-[p-chloro-N-(6-methoxybiphenyl-3-yl)benzamido]-butyric acid 8.0 g of ethyl 4-(6-methoxybiphenyl-3-yl)aminobutyrate and, 3.3 g of ethyldiisopropylamine in 50 ml of benzene are reacted, analogously to Example 47b), with 4.6 g of p-chlorobenzoyl chloride. The reaction product is dissolved in 50 ml of benzene and, after the addition thereto of a solution of 2.3 g of potassium hydroxide in 20 ml of ethanol, is then stirred for 8 hours at room temperature. After distilling off the solvent, the residue is dissolved in water; the resulting solution is acidified with dilute hydrochloric acid and extracted with diethyl ether. The residue (remaining after evaporating off the ether) is recrystallized from ethyl acetate/petrol ether (1:1) to obtain 8.1 g (73.5% of theory) of 4-[p-chloro-N-(6-methoxybiphenyl-3-yl)-benzamido]butyric acid, MP 114° to 116°.

EXAMPLE 60

4-[5-chloro-2-methoxy-N-(6-methoxybiphenyl-3-yl)benzamido]butyric acid $R^1$ = 5-chloro-2-methoxyphenyl, R = 6-methoxybiphenyl-3-yl, n = 3

Analogously to Example 59, reacting 7.0 g of ethyl 4-(6-methoxybiphenyl-3-yl)aminobutyrate with 4.6 g of 5-chloro-2-methoxybenzoyl chloride, followed by saponification of the intermediate product, yields 7.1 g (70.1% of theory) of 4-[5-chloro-2-methoxy-N-(6-methoxybiphenyl-3-yl)benzamido]-butyric acid, MP 155° to 156°.

EXAMPLE 61

6-[2,4-dichloro-N-(biphenyl-2-yl)benzamido]caproic acid $R^1$ = 2,4-dichlorophenyl, R = biphenyl-2-yl, n = 5

Following the procedure of Example 55, but substituting 2,4-dichlorobenzoyl chloride for p-chlorobenzoyl chloride, yields 6-[2,4-dichloro-N-(biphenyl-2-yl)benzamido]-caproic acid, MP 112° to 113°, from ethyl acetate/petrol ether (1:1).

EXAMPLE 62

4-[p-chloro-N-(1',2',3',4',5',6'-hexahydrobiphenyl-4-yl)benzamido]butyric acid $R^1$ = p-chlorophenyl, R = 1',2',3',4',5',6'-hexahydrobiphenyl-4-yl, n = 3

Following the procedure of Example 47(a–c), but substituting p-cyclohexylaniline for 2-amino-biphenyl, 4-[p-chloro-N-(1',2',3',4',5',6'-hexahydrobiphenyl-4-yl)-benzamido]butyric acid, MP 75° to 77°, is obtained from isopropyl alcohol/water (1:1).

EXAMPLE 63

5-[p-chloro-N-(biphenyl-2-yl)benzamido]valeric acid (a) 5-[N-(biphenyl-2-yl)amino]valeric acid A solution of 8.0 g of ethyl 5-(biphenyl-2-yl)aminovalerate (see Example 53) in 60 ml of benzene is mixed with a solution of 2.2 g of potassium hydroxide in 20 ml of ethanol. After allowing the resulting admixture to stand for 24 hours at room temperature, the solvent mixture is distilled off in vacuo. The residue is then dissolved in water; the obtained aqueous solution is washed with diethyl ether and then acidified with dilute hydrochloric acid. The formed precipitate, which is oily at first, is taken up in dichloromethane. The solvent is then distilled off and the residue recrystallized from ethyl acetate/petrol ether (1:1) to obtain 5.6 g (77.3% of theory) of 5-[N-(biphenyl-2-yl)amino]valeric acid, MP 73° to 75°.

(b) 5-[p-chloro-N-(biphenyl-2-yl)benzamido]valeric acid 5.4 g of 5-[N-(biphenyl-2-yl)amino]valeric acid is dissolved in 40 ml of 0.2 N caustic soda solution. Into the resulting clear solution (while vigorously stirring and constantly controlling the pH) 3.5 g of p-chlorobenzoyl chloride is added, drop by drop, while concurrently adding dilute caustic soda solution in order to maintain the pH at between 7 and 8. After the addition of acid chloride is complete, the solution is stirred for a further 30 minutes at pH 8 and then acidified to pH 3 with dilute hydrochloric acid. The precipitate, which is oily at first crystallizes after a time. It is filtered off and recrystallized from isopropyl alcohol to obtain 7.6 g (93% of thoery) of 5-[p-chloro-N-(biphenyl-2-yl)benzamido]valeric acid, MP 170° to 173°, which is identical with the compound obtained by the procedure of Example 53.

EXAMPLE 64

Ampoules containing 600 mg of 4-[p-chloro-N-(biphenyl-2-yl)benzamido]butyric acid; size of batch: 250 kg.

25.0 kg of 1,2-propyleneglycol and 150.0 kg of double-distilled water are placed in a vessel to which 15.0 kg of 4-[p-chloro-N-(biphenyl-2-yl)benzamido]butyric acid are added. Then, while stirring, caustic soda solution (10 percent by weight NaOH) is slowly added. When a solution is obtained, the pH is adjusted to from 7.5 to 8.0. Sodium pyrosulfite*) is added, and the resulting mixture is stirred until all components have dissolved. Using double-distilled water, the solution is made up to 250 kg. The solution is then charged into 10-ml ampoules and sterilized in an autoclave for 30 minutes at 120°.

(*) 0.0625 kg.

EXAMPLE 65

Ampoules containing 600 mg of 4-[N-(biphenyl-2-yl)-crotonoylamido]butyric acid; size of batch: 250 kg.

50.0 kg of 1,2-propyleneglycol and 150.0 kg of double-distilled water are placed in a vessel. While stirring, 15 kg of 4-[N-(biphenyl-2-yl)crotonoylamido]butyric acid are added thereto. Then caustic soda solution (10 percent by weight NaOH) is added, and the resulting mixture is adjusted to a pH of 8.0. Using double-distilled water, it is made up to 250 kg. The solution is charged into 10-ml ampoules and sterilized in an autoclave at 120° for 30 minutes.

EXAMPLE 66

Tablets containing 50 mg of 4-[p-fluoro-N-(biphenyl-2-yl)benzamido]butyric acid 25.0 kg of 4-[p-fluoro-N-(biphenyl-2-yl)benzamido]butyric acid, 35.0 kg of lactose and 26.0 kg of maize starch are granulated with 21.5 kg of polyvinylpyrrolidone (molecular weight: approx. 25,000) in about 6 liters of water. The granulate is passed through a sieve with a mesh width of 1.25 mm and, after drying, is admixed with 8.0 kg of carboxymethylcellulose, 2.5 kg of talcum and 1.0 kg of magnesium stearate. The dry granulate is pressed into tablets with a diameter of 8 mm, a weight of 250 mg and a hardness of from 5 to 6 kg.

In a similar manner tablets containing 4-[p-chloro-N-(biphenyl-2-yl)benzamido]butyric acid or 4-[N-(biphenyl-2-yl)crotonoylamido]butyric acid are prepared.

EXAMPLE 67

Tablets containing 100 mg of 4-[N-(biphenyl-2-yl)-acetamido]butyric acid 40.0 kg of 4-[N-(biphenyl-2-yl)acetamido]butyric acid, 24.0 kg of lactose and 16.0 kg of maize starch are granulated with 4.0 kg of polyvinylpyrrolidone (molecular weight: approx. 25,000) in about 5.5 liters of water and then pressed through a sieve with a mesh width of 1.25 mm. After drying, 10.0 kg of carboxymethylcellulose, 4.0 kg of talcum and 2.0 kg of magnesium stearate are admixed therewith. On an eccentric machine the resulting granulate is pressed into tablets with a diameter of 9 mm, a weight of 250 mg and a hardness of from 4 to 5 kg.

EXAMPLE 68

Tablets containing 300 mg of 4-[p-chloro-N-biphenyl-2-yl)benzamido]butyric acid 60.0 kg of 4-[p-chloro-N-(biphenyl-2-yl)benzamido]butyric acid, 12.0 kg of lactose and 8.0 kg of maize starch are granulated with 4.0 kg of polyvinylpyrrolidone (molecular weight: approx. 25,000) in about 6 liters of water and then pressed through a sieve with a mesh width of 1.25 mm. After drying, 10.0 kg of carboxymethylcellulose, 4.0 kg of talcum and 2.0 kg of magnesium stearate are admixed therewith. On a rotary pelleting machine the resulting granulate is pressed into tablets with a diameter of 11 mm, a weight of 500 mg and a hardness of from 6 to 7 kg.

Analogously, tablets are produced which contain 300 mg of 4-[p-chloro-N-(biphenyl-2-yl)benzamido]caproic acid.

EXAMPLE 69

10,000 capsules with an active-principle content of 50 mg are produced from the following components: 500 g of 4-[N-(biphenyl-2-yl)crotonoylamido]butyric acid, 495 g of microcrystalline cellulose and 5 g of amorphous silica. The active principle in finely-powdered form, the cellulose and the silica are thoroughly mixed and packed into hard gelatin (size 4) capsules.

Pharmacology

The acylbiphenylylaminoacids of formula Ic exert a marked protective action on the stomach and liver of rats and, in addition, increase the pancreatic and bile secretion of rats. For these effects they are superior to known commercial preparations, for example Piprozoline and Carbenoxolone. In addition, they bring about an inhibition of glucose formation from lactate and pyruvate in the liver of rats; for this purpose they are superior to known commercial preparations, such as Buformin and Phenformin.

In the tables which follow, the compounds investigated are characterized by a serial number which has been allocated as follows:

| Serial No. | Name of Compound |
|---|---|
| 1 | Piprozoline |
| 19 | Carbenoxolone |
| 20 | Buformin |
| 21 | Phenformin |
| 22 | 4-[N-(biphenyl-2-yl)acetamido]butyric acid |
| 23 | 4-[p-chloro-N-biphenyl-4-yl)benzamido]butyric acid |
| 24 | 6-[p-chloro-N-(biphenyl-2-yl)benzamido]caproic acid |
| 25 | 4-[m-trifluoromethyl-N-(biphenyl-2-yl)benzamido]butyric acid |
| 26 | 4-[p-fluoro-N-(biphenyl-2-yl)benzamido]butyric acid |
| 27 | 4-[N-(biphenyl-2-yl)crotonoylamido]butyric acid |
| 28 | 5-[p-chloro-N-(biphenyl-2-yl)benzamido]valeric acid |
| 29 | 6-[2,4-dichloro-N-(biphenyl-2-yl)benzamido]caproic acid |
| 30 | 6-[5-chloro-2-methoxy-N-(biphenyl-2-yl)benzamido]caproic acid |
| 31 | 4-[p-chloro-N-(biphenyl-2-yl)benzamido]butyric acid |
| 32 | 5-[o-hydroxy-N-(biphenyl-2-yl)benzamido]valeric acid |
| 33 | 4-[2-methoxy-5-chloro-N-(biphenyl-2-yl)benzamido]butyric acid |
| 34 | 6-[-N-(biphenyl-2-yl)isobutyramido]caproic acid |
| 35 | 4-[p-chloro-N-(6-methoxybiphenyl-3-yl)-benzamido]butyric acid |
| 36 | 4-[2-methoxy-5-chloro-N-(6-methoxybiphenyl-3-yl)benzamido]butyric acid |
| 37 | 4-[p-chloro-N-(1',2',3',4',5',6'-hexahydrobiphenyl-4-yl)benzamido]butyric acid. |

Table IV shows the stomach-protective action (reversal of the stomach ulcer caused by the ligature of the pylorus and administering 100 mg/kg of acetylsalicyclic acid per os) after intraduodenal application in the rat, the lethal action after intraperitoneal administration in the mouse and also the therapeutic quotient ($TQ=LD_{50}/ED_{50}$) of representative compounds of formula Ic according to the invention.

TABLE IV

Stomach Protection Action

| Serial No. | Toxicity $LD_{50}$ (mg/kg) (mouse, i.p.) | Antiulcerogenic Action/rat $ED_{50}$* mg/kg intraduodenally | TQ $LD_{50}/ED_{50}$ |
|---|---|---|---|
| 19 | 120 | 50 | 2.4 |
| 31 | 180 | 35 | 5.1 |
| 22 | 750 | 55 | 13.6 |
| 23 | 120 | ~15 | ~8 |
| 24 | 130 | ~40 | ~3.3 |
| 25 | 110 | 10 | 11 |
| 26 | 210 | ~55 | ~3.8 |
| 35 | 120 | <10 | >12 |
| 27 | 300 | ~55 | ~5.5 |
| 30 | >200 | 10 | >20 |
| 32 | >200 | <10 | >20 |

*Dose which reduces the mean ulcer index by 50%.

Table V shows investigations regarding the antihepatotoxic action ($ED_{25;50}$) of the compounds according to the invention after oral application to wakeful rats and the lethal action after intraperitoneal application on the mouse ($LD_{50}$) as well as the therapeutic quotient ($TQ=LD_{50}/ED_{50}$ or $LD_{50}/ED_{25}$).

TABLE V

Antihepatotoxic Effect, Toxicity and Therapeutic Quotient

| Serial No. | Toxicity $LD_{50}$ (mg/kg) mouse i.p. | Antihepatoxic Effect $ED_{25}$* mg/kg per os Rat | $ED_{50}$* mg/kg per os Rat | TQ $LD_{50}/ED_{25}$ | TQ $LD_{50}/ED_{50}$ |
|---|---|---|---|---|---|
| 1 | 1070** | 200 | >300 | 5.4 | <3.6 |
| 22 | 750 | <3 | 15 | >250 | 50 |
| 23 | 120 | 15 | 22 | 8 | 5.5 |
| 24 | 130 | ~9 | 14 | ~14.4 | 9.3 |
| 25 | 110 | 10 | 30 | 11 | 3.7 |
| 26 | 210 | 1.6 | 2.8 | 131.3 | 75 |
| 27 | 300 | 1.6 | 2.8 | 187.5 | 107.1 |
| 28 | 140 | 3 | 12 | 46.7 | 11.7 |
| 30 | >200 | 10 | | >20 | |
| 31 | 180 | <1 | 3.5 | >180 | 51.4 |
| 34 | 260 | <30 | | | 8.7 |
| 37 | ~150 | ≲10 | | ≳15 | |

*$ED_{25}$ or $ED_{50}$ = which shortens (by 25 and 50%, respectively) the hexobarbital narcosis of rats suffering from liver damage by $CCl_4$.
**$LD_{50}$ (per os) cited from Herrmann et al. Arzneim.-Forsch. 27 (1977) 467.

Table VI shows (for representative compounds of formula Ic according to the invention) the influence on bile secretion (choleresis) of narcotized rats after intraduodenal application ($ED_{50}$), the lethal action on the mouse ($LD_{50}$) after intraperitoneal application and also the therapeutic quotient ($TQ=LD_{50}/ED_{50}$).

TABLE VI

Bile Secretion, Toxicity and Therapeutic Quotient

| Serial No. | Toxicity $LD_{50}$ (mg/kg) (Mouse i.p.) | Bile Secretion $ED_{50}$*** (mg/kg) (Rat i.d.) | TQ ($LD_{50}/ED_{50}$) |
|---|---|---|---|
| 1 | 1070** | 40 | 26.8 |
| 22 | 750 | 8 | 93.8 |
| 27 | 300 | 10 | 30 |
| 36 | 190 | 1 | 190 |

***$ED_{50}$ = dose which brings about an increase in the bile secretion (liquid volume; 30-min. fraction) by a maximum of 50%
**$LD_{50}$ (p.o.) cited from Herrmann et al., Arzneim.-Forsch. 27 (1977) 467.

Table VII shows (for representative compounds of formula Ic according to the invention) the influence on pancreatic secretion of narcotized rats after intraduodenal application ($ED_{50}$) and the lethal action on the mouse ($LD_{50}$) after intraperitoneal application, as well as the therapeutic quotient ($TQ=LD_{50}/ED_{50}$).

TABLE VII

Pancreatic Secretion, Toxicity and Therapeutic Quotient

| Serial No. | Toxicity $LD_{50}$ [mg/kg] (Mouse, i/p) | Pancreatic Secretion $ED_{50}$* [mg/kg] (Rat, i/d) | TQ [$LD_{50}/ED_{50}$] |
|---|---|---|---|
| 1 | 1070** | 35 | 31 |
| 22 | 750 | ~2 | ~375 |
| 23 | 120 | 1 | 120 |
| 25 | 110 | 1 | 110 |
| 26 | 210 | 2.5 | 84 |
| 29 | ~250 | 1.7 | ~147 |
| 30 | >200 | <1.0 | >200 |
| 31 | 180 | 1 | 180 |
| 33 | 170 | 2 | 85 |
| 35 | 120 | 1.5 | 80 |
| 36 | 190 | 5 | 38 |
| 37 | ~150 | 1.5 | ~100 |

*$ED_{50}$ = dose which brings about an increase in pancreatic secretion (liquid volume; 30-min. fraction) of a maximum of 50%
**$LD_{50}$ (per os) cited from Hermann et al., Arzneim.-Forsch. 27 (1977) 467.

Table VIII shows the results of an investigation of the influence of representative compounds of formula Ic according to the invention on glucose formation from lactate and pyruvate in the isolated perfused liver of fasting rats, the inhibition of glucose formation being shown for a substance concentration of 0.2 mmole/liter in the perfusate and the $ED_{50}$—determined from 4 concentrations in the range of from 0.02 to 1.00 mmol/liter—and the lethal action on the mouse ($LD_{50}$) after intraperitoneal application.

TABLE VIII

Inhibition of the Formation of Glucose from Lactate and Pyruvate in the Isolated Perfused Liver of Rats and Toxicity on the Mouse

| Serial No. | Glucose Formation % change | $ED_{50}$* (mg/l) | $LD_{50}$ (i.p.) (mg/kg) |
|---|---|---|---|
| 20 | −1 | >1000 | 213*** |
| 21 | −3 | >1000 | 150**** |
| 31 | −79 | 43 | 180 |
| 24 | −99 | 23 | 130 |
| 25 | −77 | 34 | 110 |
| 26 | −51 | 76 | 210 |
| 28 | −89 | 25 | 140 |
| 29 | −93 | 23 | ~250 |

*$ED_{50}$ = dose which brings about an inhibition of formation of glucose from lactate and pyruvate of a maximum of 50%
***cited from Soling H.D., Creutzfeldt, W., Int. Biguanid Symp., Aachen 1960, Stuttgart, Thieme Verlag
****cited from Bertarelli, P., Boll. chim. farm. 97 (1958) 396

The compounds of formula Ic according to the invention are characterized, as compared with the comparison compounds 20 and 21, by a considerably stronger inhibition of the formation of glucose from lactate and pyruvate. Whereas compounds 20 and 21 exert practically no inhibition at the concentrations used, with the compounds of formula Ic inhibition effects of up to 99% are achieved.

EXAMPLE 70

4-[(p-chloro-N-(α-naphthyl)benzamido]butyric acid $R^1$=p-chlorophenyl, R=α-naphthyl, n=3

4.0 g of α-naphthylamine, 3.6 g of ethyldiisopropylamine, 5.5 g of ethyl 4-bromobutyrate and 20 ml of cyclohexane are heated to boiling together for 3 hours under reflux. After cooling, the formed precipitate is filtered off, and the filtrate is concentrated by evaporation in vacuo. The residue (after evaporation) is dissolved in 30 ml of benzene. After the addition of 3.5 g of ethyldiisopropylamine thereto, a mixture of 4.7 g of p-chlorobenzoyl chloride and 10 ml of benzene is added (accompanied by agitation) drop by drop at room temperature over a period of 30 minutes. The agitation is then continued for a further hour, the precipitate is filtered off, and the filtrate concentrated by evaporation. The evaporation residue is dissolved in 50 ml of benzene and is mixed with a solution of 2.0 g of potassium hydroxide in 20 ml of ethanol. After allowing the resulting solution to stand at room temperature for 12 hours, it is extracted twice with 50 ml of water on each occasion. The combined aqueous phases are washed once with diethyl ether and then acidified with dilute hydrochloric acid. The precipitate is filtered off and recrystallized from a 1:1 mixture of isopropyl alcohol and water to obtain 6.3 g (61.3% of theory) of 4-{p-chloro-[N-(α-naphthyl)]-benzamido}butyric acid, MP 173° to 174°.

EXAMPLE 71

4-{2,4-dichloro-[N-(α-naphthyl)]benzamido}butyric acid $R^1$ = 2,4-dichlorophenyl, R = α-naphthyl, n = 3

This compound is obtained by the process described in Example 70, but using 2,4-dichlorobenzoyl chloride. The title compound, MP 134° to 136°, is crystallized from (1:1) isopropyl alcohol/water.

EXAMPLE 72

4-{m-trifluoromethyl-[N-(α-naphthyl)]benzamido}-butyric acid $R^1$ = m-trifluoromethylphenyl, R = α-naphthyl, n = 3

This compound is obtained according to the process of Example 70, but using m-trifluoromethylbenzoyl chloride. The title compound, MP 128° to 129°, is crystallized from (1:1) isopropyl alcohol/water.

EXAMPLE 73

4-{o-hydroxy-[N-(α-naphthyl)]benzamido}butyric acid $R^1$ = o-hydroxyphenyl, R = α-naphthyl, n = 3

This compound is obtained by the process of Example 70, but using o-acetoxybenzoyl chloride. The title compound, MP 126° to 128°, is crystallized from (1:1) ethanol/water.

EXAMPLE 74

4-{5-chloro-2-methoxy-[N-(α-naphthyl)]benzamido}-butyric acid $R^1$ = 5-chloro-2-methoxyphenyl, R = α-naphthyl, n = 3

This compound is obtained by the process of Example 70, but using 5-chloro-2-methoxybenzoyl chloride. The title compound, MP 170° to 171°, is crystallized from isopropyl alcohol.

EXAMPLE 75

4-{3,4,5-trimethoxy-[N-(α-naphthyl)]benzamido}-butyric acid

This compound is obtained by the process of Example 70, but using 3,4,5-trimethoxybenzoyl chloride. The title compound, MP 143° to 145°, is crystallized from (2:1) isopropyl alcohol/diethyl ether.

EXAMPLE 76

4-[N-(α-naphthyl)acetamido]butyric acid $R^1$ = —CH$_3$, R = α-naphthyl, n = 3

This compound is produced by the process of Example 70, but using acetyl chloride. The title compound, MP 117° to 119° is crystallized from cyclohexane.

EXAMPLE 77

5-{p-chloro-[N-(α-naphthyl)]benzamido}valeric acid $R^1$ = p-chlorophenyl, R = α-naphthyl, n = 4

(a) Ethyl 5-{p-chloro-[N-(α-naphthyl)]benzamido}valerate 7.2 g of α-naphthylamine, 6.5 g of ethyldiisopropylamine, 10.5 g of ethyl 5-bromovalerate and 40 ml of cyclohexane are heated to boiling under reflux for 20 hours. After cooling, the resulting precipitate is filtered off, and the filtrate is concentrated in vacuo. The evaporation residue is taken up in 80 ml of benzene. After the addition of 6.8 g of ethyldiisopropylamine, a mixture of 9.2 g of p-chlorobenzoyl chloride and 20 ml of benzene is added drop by drop over a period of 1 hour and accompanied by agitation at room temperature. After 24 hours the reaction mixture is diluted with diethyl ether, and the precipitate is filtered off. The filtrate is washed successively with water, dilute hydrochloric acid and sodium bicarbonate solution; it is then dried and concentrated by evaporation. The evaporation residue is purified by chromatography over a silica gel column (eluting agent: dichloromethane) and is then recrystallized from a (1:1) mixture of cyclohexane and petrol ether (BP 50° to 70° C.) to obtain 13.2 g (64% of theory) of ethyl 5-{p-chloro-[N-(α-naphthyl)]benzamido}valerate, MP 74° to 75°.

(b) 5-{p-chloro-[N-(α-naphthyl)]benzamido}valeric acid 12.8 g of ethyl 5-{p-chloro-[N-(α-naphthyl]benzamido}-valerate in 100 ml of benzene are mixed with a solution of 2.6 g of potassium hydroxide in 20 ml of ethanol. After 2 days the solvent is distilled off, the residue is then dissolved in water, and the resulting aqueous solution is washed with diethyl ether and then acidified with dilute hydrochloric acid. The reaction product is extracted with diethyl ether, and the residue (remaining after drying and distilling off the solvent) is recrystallized from ethyl acetate/petrol ether (1:1) to obtain 10.6 g (88.9% of theory) of 5-{p-chloro-[N-(α-naphthyl)]benzamido}valeric acid, MP 169° to 170°.

EXAMPLE 78

6-{p-chloro-[N-(α-naphthyl)]benzamido}caproic acid $R^1$ = p-chlorophenyl, R = α-naphthyl, n = 5

Following the process of Example 77a (but replacing ethyl 5-bromovalerate with ethyl 6-bromocaproate) ethyl 6-{p-chloro-[N-(α-naphthyl)]benzamido}caproate, MP 76.5° to 77.5° is obtained from cyclohexane/petrol ether (1:1). By saponification of this ester according to Example 77b 6-{p-chloro-[N-(α-naphthyl)]benzamido}caproic acid, MP 131° to 132° is obtained from ethyl acetate/petrol ether (1:1).

EXAMPLE 79

4-{p-chloro-[N-(α-naphthyl)]benzamido}valeric acid $R^1$ = p-chlorophenyl, R = α-naphthyl, n = 4

Following the process of Example 70, but replacing ethyl 4-bromobutyrate by ethyl 4-bromovalerate, 4-{p-chloro-[N-(α-naphthyl)]benzamido}valeric acid, MP 119° to 120° is obtained from ethyl acetate/petrol ether (1:1).

EXAMPLE 80

4-{p-chloro-[N-(7-methoxy-1-naphthyl)]benzamido}-butyric acid $R^1$ = p-chlorophenyl, R = 7-methoxy-1-naphthyl, n = 3

10.4 g of 1-amino-7-methoxynaphthalene, 7.8 g of ethyldiisopropylamine, 11.8 g of ethyl 4-bromobutyrate and 50 ml of cyclohexane are heated to boiling under reflux for 5 hours. After cooling, the precipitate is filtered off, the filtrate is concentrated by evaporation and the evaporation residue is taken up in 70 ml of benzene. After the addition of 7.8 g of ethyl diisopropylamine and 10.5 g of p-chlorobenzoyl chloride thereto, the mixture is agitated at room temperature for 2 hours. The residue (which remains after filtering off the precipitate and concentrating the filtrate by evaporation) is purified chromatographically (aluminum oxide column; eluting agent: dichloromethane) to obtain 12.3 g (48.1% of theory) of ethyl-4-{p-chloro-[N-(7-methoxy-1-naphthyl)]benzamido}butyrate, MP 92° to 94°, from isopropyl alcohol.

By the saponification of 9.0 g of this ester according to the process of 77b, 7.4 g (88% of theory) of 4-{p-chloro-[N-(7-methoxy-1-naphthyl)]benzamido}butyric acid, MP 148° to 150°, is obtained from isopropyl alcohol.

EXAMPLE 81

4-{p-chloro-[N-(4-ethoxy-1-naphthyl)]benzamido}-butyric acid $R^1$ = p-chlorophenyl, R = 4-ethoxy-1-naphthyl, n = 3

Following the process of Example 70, but replacing α-naphthylamine by 1-amino-4-naphthol-ethyl ether, 4-{p-chloro-[N-(4-ethoxy-1-naphthyl)]benzamido}-butyric acid, MP 111° to 113° is obtained from ethyl acetate/petrol ether (1:1).

EXAMPLE 82

4-[N-(1,2,3,4-tetrahydro-1-naphthyl)acetamido]butyric acid $R^1$ = —CH$_3$, R = 1,2,3,4-tetrahydro-1-naphthyl, n = 3

14.7 g of 1-amino-1,2,3,4-tetrahydronaphthalene and 9.7 g of ethyl 4-bromobutyrate are stirred together for 48 hours at room temperature. After addition of 200 ml of diethyl ether thereto the resulting precipitate is filtered off, and the filtrate is shaken with dilute hydrochloric acid. The hydrochloric acid extract is neutralized (pH approx. 7) with dilute ammonia solution. The separated oil is taken up in diethyl ether, and the residue (10.9 g), which remains after drying and distilling off the solvent, is taken up in 100 ml of benzene. After the addition of 5.9 g of ethyldiisopropylamine thereto, 3.6 g of acetyl chloride are added slowly and dropwise while stirring. After 3 hours the resulting reaction mixture is mixed with 200 ml of diethyl ether and shaken successively with water, dilute hydrochloric acid and sodium bicarbonate solution. The residue (12.4 g), remaining after drying and distilling off the solvent, is taken up in 100 ml of benzene and mixed with a solution of 3.0 g of potassium hydroxide in 20 ml of ethanol. After 24 hours the mixture is shaken out with water, and the aqueous phase is acidified. The initial oily precipitate is taken up in dichloromethane. After distilling off the solvent, the product crystallizes out after several days. It is recrystallized from a mixture (2:1) of isopropyl alcohol and petrol ether to obtain 7.9 g (57.7% of theory) of 4-[N-(1,2,3,4-tetrahydro-1-naphthyl)acetamido]butyric acid, MP 141° to 142°.

EXAMPLE 83

4-[N-(1,2,3,4-tetrahydro-1-naphthyl)isobutyramido]-butyric acid $R^1$ = —CH(CH$_3$)$_2$, R = 1,2,3,4-tetrahydro-1-naphthyl, n = 3

Following the process of Example 82, but using isobutyryl chloride instead of acetyl chloride, 4-[N-(1,2,3,4-tetrahydro-1-naphthyl)isobutyramido]butyric acid, MP 92.5° to 93.5°, is obtained.

EXAMPLE 84

Sodium 4-[N-(6-methoxy-1,2,3,4-tetrahydro-1-naphthyl)propionamido]butyrate $R^1$ = —CH$_2$—CH$_3$, R = 6-methoxy-1,2,3,4-tetrahydro-1-naphthyl, n = 3

Following the process of Example 82 and replacing 1-amino-1,2,3,4-tetrahydro]naphthalene and acetyl chloride by 6-methoxy-1-amino-1,2,3,4-tetrahydronaphthalene and propionyl chloride, 4-[N-(6-methoxy-1,2,3,4-tetrahydro-1-naphthyl)propionamido]butyric acid is obtained as a viscous oil which does not crystallize even after several weeks. A solution of 8.9 g of this acid in 90 ml of isopropanol is mixed with a sodium isopropylate solution, which is produced by dissolving 0.60 g of sodium in 50 ml of isopropanol. The solvent is distilled off, and the residue is mixed with anhydrous diethyl ether. After a certain time it solidifies to form a solid crystal mass. This is ground down and washed several times with anhydrous diethyl ether to obtain 8.3 g (87.3% of theory) of the sodium salt of 4-[N-(6-methoxy-1,2,3,4-tetrahydro-1-naphthyl)propionamido]butyric acid as colorless hygroscopic crystals which melt without a sharp melting point at 75° to 85°.

EXAMPLE 85

Sodium salt of 4-[N-(6-methoxy-1,2,3,4-tetrahydro-1-naphthyl)isobutyramido]butyric acid $R^1$ = —CH(CH$_3$)$_2$, R = 6-methoxy-1,2,3,4-tetrahydro-1-naphthyl, n = 3

The title compound is produced as in Example 84, but using isobutyryl chloride instead of propionyl chloride. It forms strongly-hydroscopic crystals which melt without a sharp melting point at from 90° to 95°.

EXAMPLE 86

5-[N-(α-naphthyl)isobutyramido]valeric acid $R^1$ = —CH(CH$_3$)$_2$, R = α-naphthyl, n = 4

This compound [MP = 93° to 94° from diethyl ether/petrol ether (1:1)] is produced by the process of Example 70, but using ethyl 5-bromovalerate instead of ethyl 4-bromobutyrate and using isobutyryl chloride instead of p-chlorobenzoyl chloride.

EXAMPLE 87

5-[p-chloro-N-(indan-5-yl)benzamido]valeric acid $R^1$=p-chlorophenyl, R=indan-5-yl, n=4

(a) Ethyl 5-(indan-5-ylamino)valerate 13.3 g of 5-aminoindane, 23.0 g of ethyl 5-bromovalerate and 14.2 g of ethyl diisopropylamine are stirred together for 12 hours at 50°. After addition of diethyl ether thereto, the resulting precipitate is filtered off, the solvent is removed, and all volatile components are distilled off from the residue at 50° under a pressure of $10^{-2}$ mm Hg. The residue (which is left) is recrystallized from petrol ether to obtain 8.3 g (55.7% of theory) of ethyl 5-(indan-5-ylamino)valerate, MP 61° to 63°.

(b) 5-{p-chloro-[N-(indan-5-yl)]benzamido}valeric acid 6.3 g of ethyl 5-(indan-5-ylamino)valerate and 3.1 g of ethyl diisopropylamine are reacted in 50 ml of benzene with 4.2 g of p-chlorobenzoyl chloride. The resulting residue (left after filtering off the precipitate and concentrating the filtrate by evaporation) is saponified as described in Example 77b. Recrystallization of the crude product from ethyl acetate/petrol ether (1:2) yields 7.9 g (88.1% of theory) of 5-{p-chloro-[N-(indan-5-yl)]benzamido}valeric acid, MP 132° to 134°.

EXAMPLE 88

4-{3,4-dichloro-[N-(indan-5-yl)]benzamido}butyric acid $R^1$=3,4-dichlorophenyl, R=indan-5-yl, n=3

Following the process of Example 87, but using ethyl 4-bromobutyrate instead of ethyl 5-bromovalerate and using 3,4-dichlorobenzoyl chloride instead of p-chlorobenzoyl chloride, yields 4-{3,4-dichloro-[N-(indan-5-yl)]benzamido}-butyric acid, MP 58° to 59°, from ethyl acetate/petrol ether (1:2).

EXAMPLE 89

Ampoules containing 600 mg of 4-[N-(α-naphthyl)-acetamido]butyric acid; size of batch: 250 kg.

25.0 kg of 1,2-propyleneglycol and 150.0 kg of double-distilled water are placed in a vessel. 15.0 kg of 4-[N-(α-naphthyl)acetamido]butyric acid are added thereto before adding slowly, while stirring, caustic soda solution (10 percent by weight NaOH). When a solution is obtained, the pH is adjusted to from 7.5 to 8.0. Sodium pyrosulfite 0.0625 kg is added and the mixture is stirred until everything has dissolved. The resulting solution is made up to 250 kg with double-distilled water. The solution is charged into 10-ml ampoules and sterilized in an autoclave for 30 minutes at 120°.

EXAMPLE 90

Ampoules containing 600 mg of 4-{5-chloro-2-methoxy-[N-(α-naphthyl)]benzamido}-butyric acid; size of batch: 250 kg.

50.0 kg of 1,2-propyleneglycol and 150.0 kg of double-distilled water are placed in a vessel to which 15 kg of 4-{5-chloro-2-methoxy-[N-(α-naphthyl)]benzamido}-butyric acid are then added while stirring. Then caustic soda solution (10 percent by weight NaOH) is added, and the resulting mixture is adjusted to a pH of 8.0. It is made up to 250 kg with double-distilled water. The obtained solution is charged into 10-ml ampoules and sterilized in an autoclave for 30 minutes at 120°.

EXAMPLE 91

Tablets containing 50 mg of 6-{p-chloro-[N-(α-naphthyl)]benzamido}caproic acid.

25.0 kg of 6-{p-chloro-[N-(α-naphthyl)]benzamido}-caproic acid, 35.0 kg of lactose and 26.0 kg of maize starch are granulated with 21.5 kg of polyvinylpyrrolidone (molecular weight: approx. 25,000) in about 6 liters of water. The resulting granulate is sieved through a sieve with a mesh width of 1.25 mm and, after drying, is admixed with 8.0 kg of carboxymethylcellulose, 2.5 kg of talcum and 1.0 kg of magnesium stearate. Thus-produced dry granulate is pressed into tablets with a diameter of 8 mm, a weight of 250 mg and a hardness of from 5 to 6 kg.

In a similar manner tablets containing sodium 4-[N-(6-methoxy-1,2,3,4-tetrahydro-1-naphthyl)propionamido]-butyrate or 4-{3,4-dichloro-[N-(indan-5-yl)]benzamido}butyric acid are prepared.

EXAMPLE 92

Tablets containing 100 mg of 4-{p-chloro-[N-(α-naphthyl)]benzamido}valeric acid.

40.0 kg of 4-{p-chloro-[N-(α-naphthyl)]benzamido}-valeric acid, 24.0 kg of lactose and 16.0 kg of maize starch are granulated with 4.0 kg of polyvinylpyrrolidone (molecular weight: approx. 25,000) in about 5.5 liters of water and pressed through a sieve of a mesh width of 1.25 mm. After drying, 10.0 kg of carboxymethylcellulose, 4.0 kg of talcum and 2.0 kg of magnesium stearate are admixed therewith. Using an eccentric machine, the resulting granulate is pressed into tablets with a diameter of 9 mm, a weight of 250 mg and a hardness of from 4 to 5 kg.

EXAMPLE 93

Tablets containing 300 mg of 5-[N-(α-naphthyl)-isobutyramido]valeric acid.

60.0 kg of 5-[N-(α-naphthyl)isobutyramido]valeric acid, 12.0 kg of lactose and 8.0 kg of maize starch are granulated with 4.0 kg of polyvinylpyrrolidone (molecular weight: approx. 25,000) in about 6 liters of water and are pressed through a sieve with a mesh width of 1.25 mm. After drying, 10.0 kg of carboxymethylcellulose, 4.0 kg of talcum and 2.0 kg of magnesium stearate are admixed therewith. On a rotary pelleting machine the resulting granulate is pressed into tablets with a diameter of 11 mm, a weight of 500 mg and a hardness of from 6 to 7 kg.

EXAMPLE 94

10,000 capsules with an active principle content of 50 mg are produced from the following components: 500 g of 6-{p-chloro-[N-(α-naphthyl)]benzamido}caproic acid, 495 g of microcrystalline cellulose and 5 g of amorphous silica. The active principle in finely-powdered form, the cellulose and the silica are thoroughly mixed and packed into hard gelatin (size 4) capsules.

Pharmacology

The acyl-(bicyclic aryl)aminoalkanoic acids of formula Id and of pharmacologically-acceptable salts thereof exert a marked protective action on the stomach and cause an increase in pancreatic secretion in rats. They also exert a positive action (liver protection and choleresis) on the liver and bile of rats and are superior to known commercial preparations, such as Piprozoline and Carbenoxolone in this regard. In addition, they exert an inhibitive effect on glucose formation from lactate and pyruvate in the liver of rats, for which purpose they are superior to known commercial preparations, such as Buformin and Phenformin.

In subsequent tables investigated compounds are marked by a serial number, which has been allocated to them as follows:

| Serial No. | Name of Compound |
|---|---|
| 1 | Piprozoline |
| 19 | Carbenoxolone |
| 20 | Buformin |
| 21 | Phenformin |
| 38 | 4-{p-chloro-[N(α-naphthyl)]benzamido}butyric acid |
| 39 | 4-[N-(α-naphthyl)acetamido]butyric acid |
| 40 | 4-{3,4,5-trimethoxy-[N-(α-naphthyl) benzamido]-butyric acid |
| 41 | 4-{2,4-dichloro-[N-(αnaphthyl)]benzamido}-butyric acid |
| 42 | 4-{m-trifluoromethyl-[N-(α-naphthyl)]benzamido}-butyric acid |
| 43 | 4-{p-chloro-[N-(4-ethoxy-1-naphthyl)]benzamido}-butyric acid |
| 44 | 4-{5-chloro-2-methoxy-[N-(α-naphthyl)]benzamido}-butyric acid |
| 45 | 4-{p-chloro-[N-(α-naphthyl)]benzamido}valeric acid |
| 46 | 4-{p-chloro-[N-(7-methoxy-1-naphthyl)]benzamido}butyric acid |
| 47 | 5-{p-chloro-[N-(α-naphthyl)]benzamido}valeric acid |
| 48 | 6{p-chloro-[N-(α-naphthyl)]benzamido}caproic acid |
| 49 | 4-[N-(1,2,3,4-tetrahydro-1-naphthyl)acetamido]-butyric acid |
| 50 | 4-[N-(1,2,3,4-tetrahydro-1-naphthyl)isobutyramido]butyric acid |
| 51 | 5-[N-(α-naphthyl)isobutyramido]valeric acid |
| 52 | Sodium 4-[N-(6-methoxy-1,2,3,4-tetrahydro-1-naphthyl)propionamido]butyrate |
| 53 | 4-{3,4-dichloro-[N-(indan-5-yl)]benzamido}-butyric acid |
| 54 | 5-{p-chloro-[N-(indan-5-yl)]benzamido}valeric acid, |

Table IX shows the stomach-protective action (reversal of the stomach ulcer caused by the ligature of the pylorus and administering 100 mg/kg of acetylsalicylic acid per os) after intraduodenal application in the rat, the lethal action after intraperitoneal administration in the mouse and also the therapeutic quotient ($TQ = LD_{50}/ED_{50}$) of representative compounds of formula Id according to the invention.

TABLE IX

| | Stomach Protection Action | | |
|---|---|---|---|
| Compound | Toxicity $LD_{50}$ (mg/kg) (mouse i.p.) | Antiulcerogenic Action $Ed_{50}$* mg/kg intraduodenally | TQ $LD_{50}/ED_{50}$ |
| 19 | 120 | 50 | 2.4 |
| 43 | 70 | 10 | 7 |
| 45 | 180 | <10 | >18 |
| 51 | >200 | <10 | ~20 |
| 52 | >200 | <10 | >20 |
| 53 | 180 | <10 | >18 |
| 54 | 160 | ≳10 | ≲16 |

*$ED_{50}$ = dose which reduces the mean ulcer index by 50%.

Table X shows the influence on the pancreatic secretion of narcotized rats after intraduodenal application ($ED_{50}$), the lethal action on the mouse ($LD_{50}$) after intraperitoneal application of representative compounds of formula Id according to the invention and also the therapeutic quotient ($TQ = LD_{50}/ED_{50}$).

TABLE X

| | Pancreatic Secretion, Toxicity and Therapeutic Quotient | | |
|---|---|---|---|
| Serial No. | Toxicity $LD_{50}$ (mg/kg) (mouse i.p.) | Pancreatic Secretion $ED_{50}{}^+$ (mg/kg) (rat, i.d.) | TQ $LD_{50}/ED_{50}$ |
| 1 | 1070++ | 35 | 31 |
| 38 | 140 | 2.5 | 56 |
| 39 | 750 | ~1.5 | ~500 |
| 41 | 240 | 7.5 | 32 |
| 42 | 160 | <1 | >160 |
| 43 | 70 | 0.7 | 100 |
| 44 | 270 | <1 | >270 |
| 45 | 180 | ~1 | ~180 |
| 46 | 120 | 0.3 | 400 |
| 47 | 170 | 2 | 85 |
| 48 | 160 | ~1 | ~160 |
| 49 | >200 | ~5 | ≳40 |
| 50 | >200 | ~3 | ≳66.7 |
| 52 | >200 | <1 | >200 |
| 53 | 180 | <1 | >180 |

$^+ED_{50}$ = dose which brings about an increase in pancreatic secretion (liquid volume; 30-minute fraction) by a maximum of 50%.
$^{++}LD_{50}$ (p.o.) cited from Herrmann et al., Arzneim. Forsch. 27 (1977) 467.

Table XI shows investigations on the antihepatotoxic action ($ED_{25;50}$) of compounds of formula Id according to the invention after oral application to wakeful rats and the lethal action after intraperitoneal application on the mouse ($LD_{50}$), as well as the therapeutic quotient ($TQ = LD_{50}/ED_{25}$ or $LD_{50}/ED_{50}$).

TABLE XI

| | Antihepatotoxicity, Toxicity and Therapeutic Quotient | | | | |
|---|---|---|---|---|---|
| Compound | Toxicity $LD_{50}$ (mg/kg) (mouse i.p.) | Antihepatotoxid Effect (rat p.o.) | | TQ | |
| | | $ED_{25}{}^+$ | $ED_{50}{}^+$ | $\frac{LD_{50}}{ED_{25}}$ | $\frac{LD_{50}}{ED_{50}}$ |
| 1 | 1070++ | 200 | >300 | 5.4 | <3.6 |
| 38 | 140 | ~5 | 40 | ~28 | 3.5 |
| 39 | 750 | <10 | 50 | >75 | 15 |
| 40 | 360 | 17 | ≳30 | 21.2 | ≲12 |
| 41 | 240 | 10 | 26 | 24 | 9.2 |
| 44 | 270 | ~30 | | ~9 | |
| 45 | 180 | ~15 | | ~12 | |
| 46 | 120 | 7 | 16 | 17.1 | 7.5 |
| 48 | 160 | ~7 | | ~22.9 | |
| 49 | >200 | <10 | | >20 | |
| 53 | 180 | 10 | | 18 | |

$^+ED_{25}$ and $ED_{50}$ = the dose which shortens (by 25% and 50%, respectively) the hexobarbital narcosis of rats suffering from liver damage by $CCl_4$.
$^{++}LD_{50}$ (p.o.), cited from Herrmann et al., Arzneim. Forsch. 27 (1977) 467.

Table XII shows the influence on bile secretion (choleresis) of narcotized rats after intraduodenal application ($ED_{50}$), the lethal action on the mouse ($LD_{50}$) after intraperitoneal application of representative compounds of formula Id according to the invention and the therapeutic quotient ($TQ = LD_{50}/ED_{50}$).

TABLE XII

| | Bile Secretion, Toxicity and Therapeutic Quotient | | |
|---|---|---|---|
| Compound | Toxicity $LD_{50}$ (mg/kg) (mouse i.p.) | Bile Secretion $ED_{50}{}^{+++}$ (mg/kg) (rat i.d.) | TQ $LD_{50}/ED_{50}$ |
| 1 | 1070++ | 40 | 26.8 |
| 40 | 360 | 8 | 45 |

$^{+++}ED_{50}$ = dose which brings about an increase in bile secretion (liquid volume; 30-minute fraction) by a maximum of 50%.
$^{++}LD_{50}$ (p.o.) cited from Herrmann et al., Arzneim. Forsch. 27, (1977) 467.

Table XIII shows the results of an investigation of the influence of representative compounds of formula Id according to the invention on glucose formation from lactate and pyruvate in the isolated perfused liver of fasting rats, the inhibition of glucose formation being shown for a substance concentration of 0.2 mmol/liter in the perfusate, the $ED_{50}$—determined from 4 concentrations in the range from 0.02 to 1.00 mmol/liter—and the lethal action on the mouse ($LD_{50}$) after intraperitoneal application.

TABLE XIII

Inhibition of Glucose Formation from lactate and Pyruvate in the isolated perfused Rat Liver and Toxicity on the Mouse

| Serial No. | Glucose Formation % change | $ED_{50}$* (mg/l) | $LD_{50}$ (i.p.) (mg/kg) |
|---|---|---|---|
| 20 | −1 | >1000 | 213*** |
| 21 | −3 | >1000 | 150**** |
| 38 | −48 | 81 | 140 |
| 47 | −86 | 31 | 170 |
| 48 | −82 | 24 | 160 |
| 50 | −33 | 97 | >200 |

*$ED_{50}$ = dose which brings about an inhibition of formation of glucose from lactate and pyruvate of a maximum of 50%.
***cited from Soling, H.D., and Creutzfeldt, W., Int. Biguanid Symp., Aachen 1960, Stuttgart, Thieme Verlag
****cited from Bertarelli, P., Boll. chim. farm. 97 (1958) 396.

Compounds of formula Id according to the invention are characterized (as compared with comparative compounds 20 and 21) by a considerably stronger inhibition of glucose formation from lactate and pyruvate. Whereas compounds 20 and 21 exert practically no inhibition at the concentrations used, inhibition effects of up to 86% are obtained with compounds of formula Id according to the invention.

The determination of the pharmacological properties was carried out by the following methods:

Influence on the Pancreatic and Bile Secretion of the Narcotized Rat

Execution of experiment:

Male Sprague-Dawley rats (body weight from 250 to 300 g) are narcotized with 1.2 g/kg urethane i.m. Then the abdominal cavity is opened medially, the bile duct is ligatured shortly above the place where it leads into the duodenum and also near to the hepatic duct, and both sections are catheterized towards the liver.

As in the rat all the pancreatic ducts lead out into the central section of the bile duct; it is possible in this way to discharge the pancreatic secretion separately from the distal (ligatured) section and the bile separately from the proximal section of the bile duct.

The quantities of pancreatic juice and bile juice obtained are measured at intervals of 30 minutes over a period from 2 hours before to 3 hours after the intraduodenal (V. jugularis externa) administration of the compounds to be tested (quantity of liquid administered 5 ml/kg).

The body temperature of the animals is maintained at 36° to 38° C. by means of electric blankets and radiation; the temperature is monitored rectally.

Evaluation:

The liquid volumes of the 30-minute fractions after the administration of the substance are related in each case to the quantity of bile or pancreatic juice secreted prior to the application of the substance (=100%, mean of the last two measurements). The maximum percentage increase in the pancreatic or bile secretion is represented in dependence upon dose, and from this the $ED_{50}$ is determined by interpolation.

Test for Antihepatotoxic Effect

Influence on the Duration of Hexobarbital Sleep of the Rat after Liver Damage by $CCl_4$ Execution of test:

In accordance with VOGEL et al. [*Arzneim.-Forsch.*, 25 (1975) 82], liver cell damage is produced in fasting female Sprague-Dawley rats (190±10 g body weight, 10 animals/dose per test batch) by oral administration of carbon tetrachloride (0.15 mg/kg $CCl_4$ in 2.5 ml/kg olive oil), and the extent of this damage is determined by prolonging the sleeping periods induced by hexobarbital sodium (50 mg/ml/kg i.v.; caudal vein, duration of injection 45 to 60 seconds) 47 hours after the administration of the $CCl_4$. The compounds to be tested are administered 1 hour prior to the administration of $CCl_4$ orally in a liquid volume of 10 ml/kg.

Evaluation

The antihepatotoxic effect of the compounds to be tested (sodium salts in aqueous solution) is determined by the reduction of the prolongation of sleeping period caused by the $CCl_4$ liver cell damage in the groups treated, as compared with the prolongation of the sleeping period of the $CCl_4$ control group (=100%). The $ED_{50}$ is determined by interpolation from the dose/effect curve.

Determination of Toxicity

The toxicity investigations are carried out on female NMRI mice (body weight 22 to 26 g). The animals (5 animals per dose) are given food and water ad lib. Different doses of the substances are administered intraperitoneally. The duration of observation is 14 days. The $LD_{50}$, i.e. the dose at which 50% of the animals die, is determined graphically from the dose/effect curve.

Testing the Antiulcerogenic Action

The ulcer provocation is carried out on rats which have been made to fast for 24 hours (female, 180 to 200 g) by ligature of the pylorus (under ether narcosis) and the oral application of 100 mg/10 ml/kg acetylsalicylic acid. The administration of the substances was carried out intraduodenally (2.5 ml/kg) immediately after the ligature of the pylorus. The closure of the wound was carried out by means of Michel clamps. 4 hours after this, the animals were autopsied (while inebriated with ether) by dislocation of the atlas, and the stomach was resected. The stomach, opened longitudinally, is fixed on a cork board and, using a stereomicroscope with an enlargement of 10×, the number and size (=diameter) of any ulcers present were determined. The product of the degree of severity (according to the following scale of points) and the number of ulcers was used as the individual ulcer index.

Scale of points:

| | |
|---|---|
| No ulcer | 0 |
| Diam. 0.1–1.4 mm | 1 |
| 1.5–2.4 mm | 2 |
| 2.5–3.4 mm | 3 |
| 3.5–4.4 mm | 4 |
| 4.5–5.4 mm | 5 |
| >5.5 mm | 6 |

As a measure of antiulcerogenic effect the reduction in the mean ulcer index of each treated group, as compared with that of the control group (=100%), was used.

Determination of the Inhibition of the Formation of Glucose in the isolated perfused Rat Liver For this purpose young male Sprague-Dawley rats (160 to 200 g) are used. The rats are kept in cages of up to 5 animals in a temperature-controlled room (23° C.) with a fixed day/night rhythm (12/12 hours).

Food is withheld from the animals for from 20 to 22 hours prior to the operation. They are allowed to take water ad lib. The operation and the perfusion of the liver are carried out using the technique of R. Scholz et al. [*Eur. J. Biochem.* 38 (1973) 64 to 72]. The perfusion liquid used is Krebs-Henseleit bicarbonate buffer (pH 7.4), which is saturated with an oxygen/carbon dioxide mixture (95/5) and contains 1.6 mmol/liter of L-lactate and 0.2 mmol/liter of pyruvate. The perfusion liquid is pumped into the liver via a cannula inserted into the portal vein. The effluent perfusion liquid is collected via a cannula inserted into the Vena cava. The liver is perfused for about 2 hours. The test compounds are infused for 16 minutes each from the 32nd to the 80th minute after the perfusion in increasing concentrations (0.02 to 1.00 mmol/liter).

Samples of the effluent perfusion liquid are collected at one-minute intervals and analyzed for glucose, lactate and pyruvate (using standard enzymatic methods). The percentages shown in Table VIII relate to the condition occurring before and after the administration of the compounds, the changes caused solely by lactate and pyruvate being set as being equal to 100%.

The preceding disclosure adequately apprises those of ordinary skill in the relevant art:

a. what the subject invention is, including its metes and bounds;

b. how to make and use the novel compounds from known chemicals or from chemicals which are synthesized by established and recognized procedures from available starting materials;

c. how to prepare the novel compositions; and d. how to use the compounds and the compositions, and makes it clear that changes in structure and composition components are readily made without departing from the spirit or scope of the instant teachings.

What is claimed is:

1. An acyl($\gamma$-, $\delta$- or $\epsilon$-)aminoalkanoic acid of the formula

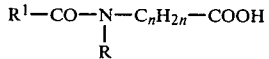

wherein

R is a member selected from the group consisting of optionally-substituted and optionally-hydrogenated biphenylyl, optionally-substituted and optionally-hydrogenated bicyclic aryl with from 8 to 12 ring carbon atoms and a radical of the formula

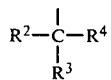

$R^1$ is aliphatic hydrocarbyl, alicyclic hydrocarbyl, phenyl or substituted phenyl;

$R^2$ is —H, alkyl, alkenyl or alkynyl;

$R^3$ is —H, alkyl, cycloalkyl, phenyl, substituted phenyl or, together with $R^4$, alkylene;

$R^4$ is alkyl, cycloalkyl, phenyl, substituted phenyl, phenalkyl, substituted phenalkyl or, together with $R^3$, alkylene; $R^4$ has at least 3 carbon atoms when $R^4$ is alkyl, $R^2$ is —H or methyl, $R^3$ is —H, and $R^1$ is alkyl, phenyl or substituted phenyl;

or $R^2$, $R^3$ and $R^4$, together with the carbon atom to which each is bound, are adamantyl; and n is 3, 4 or 5;

any substituent on a ring carbon atom being a member selected from the group consisting of halo, lower alkyl, hydroxy, lower alkoxy, lower alkylmercapto, lower aliphatic hydrocarbyl carbonyloxy, amino, monosubstituted amino, disubstituted amino, nitro, trifluoromethyl; any substituent of monosubstituted amino or of disubstituted amino being independently selected from the group consisting of lower alkyl and lower aliphatic hydrocarbyl carbonyloxy; and any substituent of substituted phenylalkyl being a nuclear substituent;

a salt of such acylaminoalkanoic acid with a base or an ester of such acid with a lower alkanol, a phenalkanol or a nuclearly-substituted phenalkanol.

2. An acylaminoalkanoic acid according to claim 1 of the formula

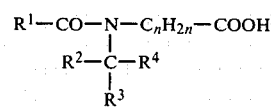

wherein $R^1$ is aliphatic hydrocarbyl, alicyclic hydrocarbyl, phenyl or substituted phenyl;

$R^2$ is —H, alkyl, alkenyl or alkynyl;

$R^3$ is —H, alkyl, cycloalkyl, phenyl, substituted phenyl or, together with $R^4$, alkylene;

$R^4$ is alkyl, cycloalkyl, phenyl, substituted phenyl, phenalkyl, substituted phenalkyl or, together with $R^3$, alkylene;

or $R^2$, $R^3$ and $R^4$, together with the carbon atom to which each is bound, are adamantyl; and n is 3, 4 or 5;

or a salt thereof with an inorganic or an organic base.

3. A compound according to claim 2 wherein $R^1$ is lower aliphatic hydrocarbyl.

4. A compound according to claim 3 wherein $R^4$ is alkyl.

5. A compound according to claim 3 wherein $R^4$ is cycloalkyl.

6. A compound according to claim 3 wherein $R^4$ is phenyl.

7. A compound according to claim 3 wherein $R^4$ is substituted phenyl.

8. A compound according to claim 3 wherein $R^4$ is phenalkyl.

9. A compound according to claim 3 wherein $R^4$ is substituted phenalkyl.

10. A compound according to claim 3 wherein $R^3$ and $R^4$, together, are alkylene with from 2 to 8 carbon atoms.

11. A compound according to claim 3 wherein $R^2$, $R^3$ and $R^4$, together with the carbon atom to which each is bound, are adamantyl.

12. A compound according to claim 2 wherein $R^1$ is alicyclic hydrocarbyl having from 3 to 10 ring carbon atoms.

13. A compound according to claim 12 wherein $R^4$ is alkyl.

14. A compound according to claim 12 wherein $R^4$ is cycloalkyl.

15. A compound according to claim 12 wherein $R^4$ is phenyl.

16. A compound according to claim 12 wherein $R^4$ is substituted phenyl.

17. A compound according to claim 12 wherein $R^4$ is phenalkyl.

18. A compound according to claim 12 wherein $R^4$ is substituted phenalkyl.

19. A compound according to claim 12 wherein $R^3$ and $R^4$, together, are alkylene with from 2 to 8 carbon atoms.

20. A compound according to claim 12 wherein $R^2$, $R^3$ and $R^4$, together with the carbon atom to which each is bound, are adamantyl.

21. A compound according to claim 2 wherein $R^1$ is optionally-substituted phenyl.

22. A compound according to claim 21 wherein $R^4$ is alkyl.

23. A compound according to claim 21 wherein $R^4$ is cycloalkyl.

24. A compound according to claim 21 wherein $R^4$ is phenyl.

25. A compound according to claim 21 wherein $R^4$ is substituted phenyl.

26. A compound according to claim 21 wherein $R^4$ is phenalkyl.

27. A compound according to claim 21 wherein $R^4$ is substituted phenalkyl.

28. A compound according to claim 21 wherein $R^3$ and $R^4$, together, are alkylene with from 2 to 8 carbon atoms.

29. A compound according to claim 21 wherein $R^2$, $R^3$ and $R^4$, together with the carbon atom to which each is bound, are adamantyl.

30. A compound according to claim 2 wherein $R^1$ is aliphatic hydrocarbyl with from 1 to 5 carbon atoms, alicyclic hydrocarbyl with from 5 to 7 ring carbon atoms or optionally-substituted phenyl of the formula

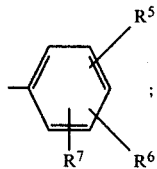

$R^2$ is —H, alkyl with from 1 to 5 carbon atoms, alkenyl with from 2 to 5 carbon atoms or alkynyl with from 2 to 5 carbon atoms;

$R^3$ is —H or alkyl with from 1 to 5 carbon atoms;

$R^4$ is alkyl with from 1 to 5 carbon atoms, each of $R^5$, $R^6$ and $R^7$ is, independently, —H, halo, alkyl with from 1 to 4 carbon atoms, alkoxy with from 1 to 4 carbon atoms, alkanoyloxy with from 2 to 5 carbon atoms, amino, nitro, —OH or trifluoromethyl;

n is 3, 4 or 5;

or a salt thereof with an organic or inorganic base.

31. A compound according to claim 30 wherein $R^1$ is aliphatic hydrocarbyl with from 1 to 5 carbon atoms or optionally-substituted phenyl;

$R^2$ is —H, alkyl with from 1 to 4 carbon atoms or ethynyl;

$R^3$ is —H or alkyl with from 1 to 3 carbon atoms;

$R^5$ is —H; and each of $R^6$ and $R^7$ is, independently, —H, halo, methyl, methoxy, amino or trifluoromethyl.

32. A compound according to claim 31 wherein $R^2$ is —H, methyl or ethynyl;

$R^3$ is —H or methyl;

$R^6$ is —H, chloro, methoxy or trifluoromethyl; and $R^7$ is —H, chloro or methoxy.

33. A compound according to claim 32 wherein n is 3.

34. A compound according to claim 2 wherein $R^1$ is aliphatic hydrocarbyl with from 1 to 5 carbon atoms, alicyclic hydrocarbyl with from 5 to 7 ring carbon atoms or optionally-substituted phenyl of the formula

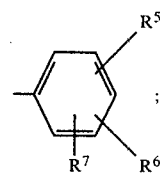

$R^2$ is —H, alkyl with from 1 to 5 carbon atoms, alkenyl with from 2 to 5 carbon atoms or alkynyl with from 2 to 5 carbon atoms;

$R^3$ is —H, alkyl with from 1 to 5 carbon atoms, cycloalkyl with from 5 to 7 ring carbon atoms; or, together with $R^4$, —$(CH_2)_q$;

$R^4$ is cycloalkyl with from 5 to 7 ring carbon atoms or, together with $R^3$, —$(CH_2)_q$;

or $R^2$, $R^3$ and $R^4$, together with the carbon atom to which each is bound, are adamantyl;

each of $R^5$, $R^6$ and $R^7$ is, independently, —H, halo, alkyl with from 1 to 4 carbon atoms, alkoxy with from 1 to 4 carbon atoms, alkanoyloxy with from 2 to 5 carbon atoms, amino, nitro, —OH or trifluoromethyl;

n is 3, 4 or 5; and q is 4, 5, 6 or 7;

or a salt thereof with an organic or inorganic base.

35. A compound according to claim 34 wherein $R^1$ is aliphatic hydrocarbyl with from 1 to 5 carbon atoms or optionally-substituted phenyl;

$R^2$ is —H, alkyl with from 1 to 4 carbon atoms or ethynyl;

$R^3$ is —H, methyl, cyclohexyl or, together with $R^4$, —$(CH_2)_q$;

$R^4$ is cyclohexyl or, together with $R^3$, —$(CH_2)_q$—;

or $R^2$, $R^3$ and $R^4$, together with the carbon atom to which each is bound, are adamantyl-(1);

$R^5$ is —H; and each of $R^6$ and $R^7$ is, independently, —H, halo, methyl, methoxy, amino or trifluoromethyl.

36. A compound according to claim 35 wherein $R^2$ is —H, methyl or ethynyl;

$R^3$ and $R^4$, together, are —$(CH_2)_q$—;

or $R^2$, $R^3$ and $R^4$, together with the carbon atom to which each is bound, are adamantyl-(1);

$R^6$ is —H, chloro, methoxy or trifluoromethyl;

$R^7$ is —H, chloro or methoxy; and q is 5 or 7.

37. A compound according to claim 36 wherein n is 3.

38. A compound according to claim 2 wherein $R^1$ is aliphatic hydrocarbyl with from 1 to 5 carbon atoms, alicyclic hydrocarbyl with from 5 to 7 ring carbon atoms or optionally-substituted phenyl;

$R^2$ is —H or alkyl with from 1 to 5 carbon atoms;

$R^3$ is —H, alkyl with from 1 to 5 carbon atoms or optionally-substituted phenyl;

$R^4$ is optionally-substituted phenyl or optionally-(nuclearly-substituted) phenalkyl, the alkyl of which is —$(CH_2)_p$—;

n is 3, 4 or 5;

p is 1, 2, 3 or 4;

and wherein each optionally-substituted phenyl and the aromatic moiety of the optionally-(nuclearly-substituted) phenalkyl are, independently, embodiments of the formula

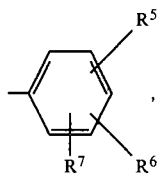

wherein each of $R^5$, $R^6$ and $R^7$ is, independently, —H, halo, —OH, alkyl with from 1 to 4 carbon atoms, alkoxy with from 1 to 4 carbon atoms, alkanoyloxy with from 2 to 5 carbon atoms, amino, nitro or trifluoromethyl;

or a salt thereof with an inorganic or organic base.

39. A compound according to claim 38 wherein $R^1$ is aliphatic hydrocarbyl with from 1 to 5 carbon atoms or optionally-substituted phenyl;

$R^2$ is —H or alkyl with from 1 to 4 carbon atoms;

$R^3$ is —H, alkyl with from 1 to 3 carbon atoms or optionally-substituted phenyl (wherein $R^6$ is —H);

$R^4$ is optionally-substituted phenyl (wherein $R^6$ is —H) or optionally-(nuclearly-substituted) benzyl (wherein $R^6$ is —H);

$R^5$ is —H; and each of $R^6$ and $R^7$ is otherwise, independently, —H, halo, methyl, methoxy, amino or trifluoromethyl.

40. A compound according to claim 39 wherein $R^2$ is —H;

$R^3$ is —H, methyl or optionally-substituted phenyl;

$R^6$ is —H, chloro, methoxy or trifluoromethyl; and $R^7$ is —H, chloro or methoxy.

41. A compound according to claim 40 wherein n is 3.

42. A compound according to claim 2 wherein $R^1$ is aliphatic hydrocarbyl with from 1 to 5 carbon atoms, alicyclic hydrocarbyl with from 5 to 7 ring carbon atoms or optionally-substituted phenyl (=B);

each B is, independently, a radical of the formula

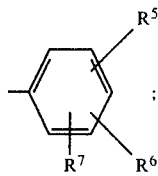

$R^2$ is alkenyl having from 2 to 5 carbon atoms or alkynyl having from 2 to 5 carbon atoms;

$R^3$ is —H or alkyl having from 1 to 5 carbon atoms;

$R^4$ is B or —$(CH_2)_p$—B;

n is 3, 4 or 5;

p is 1, 2, 3 or 4; and each of $R^5$, $R^6$ and $R^7$ is, independently, —H, halo, alkyl with from 1 to 4 carbon atoms, alkoxy with from 1 to 4 carbon atoms, alkanoyloxy with from 2 to 5 carbon atoms, amino, nitro, —OH or trifluoromethyl;

or a salt thereof with an organic or inorganic base.

43. A compound according to claim 42 wherein $R^1$ is aliphatic hydrocarbyl with from 1 to 5 carbon atoms or B;

$R^2$ is ethynyl;

$R^3$ is —H or alkyl with from 1 to 3 carbon atoms;

$R^4$ is $R^7$-phenyl or $R^7$-benzyl;

$R^5$ is —H; and each of $R^6$ and $R^7$ is, independently, —H, halo, methyl, methoxy, amino or trifluoromethyl.

44. A compound according to claim 43 wherein $R^3$ is —H or methyl;

$R^6$ is —H, chloro, methoxy or trifluoromethyl; and $R^7$ is —H, chloro or methoxy.

45. A compound according to claim 44 in which n is 3.

46. The compound according to claim 2 which is N-(p-chloro)benzoyl-4-(1-phenylethylamino)butyric acid or a pharmacologically-compatible salt thereof with an inorganic or an organic base.

47. The compound according to claim 2 which is N-acetyl-4-benzhydrylaminobutyric acid or a pharmacologically-compatible salt thereof with an inorganic or an organic base.

48. The compound according to claim 2 which is N-(p-chloro)benzoyl-4-benzhydrylaminobutyric acid or a pharmacologically-compatible salt thereof with an inorganic or an organic base.

49. The compound according to claim 2 which is N-(p-chloro)benzoyl-4-benzylaminobutyric acid or a pharmacologically-compatible salt thereof with an inorganic or an organic base.

50. An acylaminoalkanoic acid according to claim 2 having a chirality center and in the form of a racemate, an enantiomer or a mixture of enantiomers.

51. A pharmacologically-active and physiologically-acceptable pharmaceutical composition comprising from 0.5 to 1000 milligrams of at least one pharmacologically-active and physiologically-acceptable compound according to claim 2 in combination with a substantially-inert carrier therefor.

52. A process for developing a protective action for the stomach and liver and for increasing pancreas and liver secretion of a warm-blooded animal which comprises administering to the warm-blooded animal an effective amount of at least one physiologically-active and pharmacologically-acceptable compound according to claim 2.

53. A process according to claim 52 wherein the disease treated is based upon insufficient performance of the pancreas.

54. A process according to claim 52 wherein the disease treated is based upon reduced performance of the bile.

55. A process according to claim 52 wherein the disease treated is based upon reduced performance of the liver.

56. A process which comprises administering an effective prophylactic amount of at least one pharmacologically-acceptable and physiologically-active compound according to claim 2 to a mammal subject to being afflicted with a disease based on inadequate performance of the pancreas, of the bile and/or of the liver.

57. An acid or salt according to claim 1 wherein R is optionally-substituted and optionally-hydrogenated biphenylyl.

58. A physiologically-acceptable and pharmacologically-active compound according to claim 57 wherein R is biphenylyl or substituted biphenylyl.

59. A physiologically-acceptable and pharmacologically-active compound according to claim 57 wherein R is at least partially-hydrogenated biphenylyl or at least partially-hydrogenated biphenylyl which is substituted.

60. A physiologically-acceptable and pharmacologically-active compound according to claim 57 wherein $R^1$ is lower aliphatic hydrocarbyl.

61. A physiologically-acceptable and pharmacologically-active compound according to claim 57 wherein $R^1$ is alicyclic hydrocarbyl having from 3 to 10 ring carbon atoms.

62. A physiologically-acceptable and pharmacologically-active compound according to claim 57 wherein $R^1$ is optionally-substituted phenyl.

63. A compound according to claim 57 wherein
$R^1$ is aliphatic hydrocarbyl having from 1 to 7 carbon atoms, alicyclic hydrocarbyl having from 3 to 10 ring carbon atoms or optionally-substituted phenyl of the formula

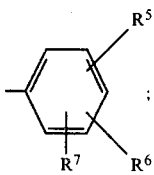

R is a group of one of the formulae:

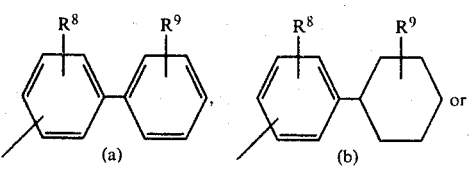

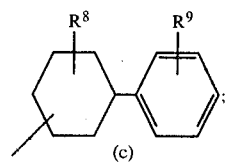

each of $R^5$, $R^6$ and $R^7$ is, independently, a member selected from the group consisting of —H, halo, —OH, alkyl with from 1 to 4 carbon atoms, alkoxy with from 1 to 4 carbon atoms, alkanoyloxy with from 2 to 5 carbon atoms, —$NO_2$ and —$CF_3$;

each of $R^8$ and $R^9$ is, independently, a member selected from the group consisting of —H, halo, methyl, methoxy, —OH and —$NO_2$; and n is 3, 4 or 5;

or a salt thereof with an inorganic or organic base.

64. A compound according to claim 63 wherein
$R^1$ is aliphatic hydrocarbyl having from 1 to 5 carbon atoms, alicyclic hydrocarbyl having from 5 to 7 ring carbon atoms or optionally-substituted phenyl;
R is a group of formula (a) or of formula (b);
$R^5$ is —H;
each of $R^6$ and $R^7$ is, independently, —H, halo, —OH, methoxy, methyl, alkanoyloxy having from 2 to 5 carbon atoms, —$NO_2$ or —$CF_3$; and
one of $R^8$ and $R^9$ is —H, and the other is —H, halo, methyl, methoxy, —OH or —$NO_2$.

65. A compound according to claim 64 wherein
$R^1$ is aliphatic hydrocarbyl with from 1 to 3 carbon atoms or optionally-substituted phenyl;
each of $R^6$ and $R^7$ is, independently, —H, fluoro, chloro, —OH, methyl, methoxy or —$CF_3$; and
one of $R^8$ and $R^9$ is —H, and the other is —H, chloro or methoxy.

66. A physiologically-acceptable and pharmacologically-active compound according to claim 65 wherein
$R^1$ is alkyl with from 1 to 3 carbon atoms, alkenyl with 2 or 3 carbon atoms or optionally-substituted phenyl;
R is a group of formula (a);
$R^6$ is —H, fluoro, chloro, —OH, methoxy or —$CF_3$;
$R^7$ is —H or chloro; and
one of $R^8$ and $R^9$ is —H, and the other is —H or methoxy.

67. A physiologically-acceptable and pharmacologically-active compound according to claim 65 wherein n is 3.

68. A physiologically-acceptable and pharmacologically-active compound according to claim 65 wherein n is 5.

69. A physiologically-acceptable and pharmacologically-active compound according to claim 65 wherein R is optionally-substituted 2-biphenylyl.

70. A pharmaceutical composition having a pharmacologically-active component and therapeutically-acceptable substantially-inert carrier and/or excipient, and wherein the active component comprises from 1 to 95 percent by weight of the composition and from 0.5 to 1000 milligrams of a pharmacologically-active and physiologically-acceptable compound according to claim 57.

71. A process for developing a protective action for the stomach and liver and for increasing pancresas and liver secretion of a warm-blooded animal which comprises administering to the warm-blooded animal an effective amount of at least one physiologically-active and pharmacologically-acceptable compound according to claim 57.

72. A process for treating diabetes which comprises administering to a warm-blooded animal afflicted therewith an effective amount of a pharmacologically-active and physiologically-acceptable compound according to claim 57.

73. An acid or salt according to claim 1 wherein R is optionally-substituted and optionally-hydrogenated bicyclic aryl having from 8 to 12 ring carbon atoms.

74. A physiologically-acceptable and pharmacologically-active compound according to claim 73 wherein R is bicyclic aryl or substituted bicyclic aryl.

75. A physiologically-acceptable and pharmacologically-active compound according to claim 73 wherein R is at least partially-hydrogenated bicyclic aryl or at least partially-hydrogenated bicyclic aryl which is substituted.

76. A physiologically-acceptable and pharmacologically-active compound according to claim 73 wherein $R^1$ is lower aliphatic hydrocarbyl.

77. A physiologically-acceptable and pharmacologically-active compound according to claim 73 wherein $R^1$ is alicyclic hydrocarbyl having from 3 to 10 ring carbon atoms.

78. A physiologically-acceptable and pharmacologically-active compound according to claim 73 wherein $R^1$ is optionally-substituted phenyl.

79. A compound according to claim 73 wherein
$R^1$ is aliphatic hydrocarbyl having from 1 to 7 carbon atoms, alicyclic hydrocarbyl having from 5 to 7 ring carbon atoms or optionally-substituted phenyl of the formula

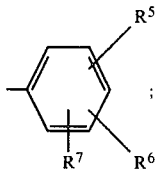

R is an optionally-substituted member selected from the group consisting of indenyl, indanyl, naphthyl, dihydronaphthyl and tetrahydronaphthyl, each having from 0 to 2 substituents independently selected from the group consisting of halo, methyl, lower alkoxy, nitro and —$CF_3$;
each of $R^5$, $R^6$ and $R^7$ is, independently, a member selected from the group consisting of —H, halo, alkyl with from 1 to 4 carbon atoms, alkoxy with from 1 to 4 carbon atoms, alkanoyloxy with from 2 to 5 carbon atoms, nitro, hydroxy and trifluoromethyl; and
n is 3, 4 or 5;
or salts thereof with an inorganic or organic base.

80. A compound according to claim 79 wherein R is an optionally-substituted member selected from the group consisting of 5-indanyl, 1-naphthyl and 1,2,3,4-tetrahydro-(1)-naphthyl.

81. A compound according to claim 80 wherein
$R^1$ is aliphatic hydrocarbyl having from 1 to 5 carbon atoms or optionally-substituted phenyl;
R is 1-naphthyl or substituted 1-naphthyl bearing one or two substituents which are independently selected from the group consisting of chloro, ethoxy, methoxy and nitro; and
each of $R^5$, $R^6$ and $R^7$ is, independently, a member selected from the group consisting of —H, halo, methyl, methoxy, nitro, hydroxy and trifluoromethyl.

82. A compound according to claim 80 wherein
R is 1-(1,2,3,4-tetrahydro)naphthyl or substituted 1-(1,2,3,4-tetrahydro)naphthyl bearing 1 or 2 substituents which are independently selected from the group consisting of chloro, methoxy and nitro;
$R^1$ is aliphatic hydrocarbyl with from 1 to 5 carbon atoms or optionally-substituted phenyl; and
each of $R^5$, $R^6$ and $R^7$ is, independently, a member selected from the group consisting of —H, halo, methyl, methoxy, nitro, hydroxy and trifluoromethyl.

83. A compound according to claim 80 wherein
$R^1$ is aliphatic hydrocarbyl with from 1 to 5 carbon atoms or optionally-substituted phenyl;
R is 5-indanyl or substituted 5-indanyl bearing one or two substituents which are independently selected from the group consisting of chloro, methoxy and nitro; and
each of $R^5$, $R^6$ and $R^7$ is, independently, a member selected from the group consisting of —H, halo, methyl, methoxy, nitro, hydroxy and trifluoromethyl.

84. A physiologically-acceptable and pharmacologically-active compound according to claim 80 wherein
R is 1-naphthyl, monomethoxy-substituted 1-naphthyl, 5-indanyl, monomethoxy-substituted 5-indanyl, 1-tetrahydronaphthyl or monomethoxy-substituted 1-tetrahydronaphthyl;
$R^1$ is alkyl having from 1 to 3 carbon atoms or optionally-substituted phenyl;
$R^5$ is —H;
$R^6$ is —H, chloro, methoxy, hydroxy or trifluoromethyl; and
$R^7$ is —H or chloro.

85. A compound according to claim 84 wherein
R is 1-naphthyl, 5-indanyl or 1-tetrahydronaphthyl;
$R^6$ is —H, chloro, methoxy or trifluoromethyl; and
n is 3.

86. A compound according to claim 84 wherein
R is 1-naphthyl, 5-indanyl or 1-tetrahydronaphthyl;
$R^6$ is —H, chloro, methoxy or trifluoromethyl; and
n is 5.

87. A pharmaceutical composition having pharmacologically-active principle and therapeutically-acceptable substantially-inert carrier and/or excipient, and wherein the active principle comprises from 1 to 95 percent by weight of the composition and from 0.5 to 1000 milligrams of a pharmacologically-active and physiologically-acceptable compound according to claim 73.

88. A process for prophylaxis of diseases which are attributable to stomach or intestine disorders or to inadequate pancreas, bile and/or liver performance and which comprises administering to a warm-blooded animal prone to at least one such afflication an effective amount of a pharmacologically-active and physiologically-acceptable compound according to claim 73.

89. A process for treating a warm-blooded animal afflicted with a stomach or intestine disorder or inadequate pancreas, bile and/or liver performance and which comprises administering to the warm-blooded animal an effective amount of a pharmacologically-active and physiologically-acceptable compound according to claim 73.

90. A process for treating diabetes which comprises administering to a warm-blooded animal afflicted therewith an effective amount of a pharmacologically-active and physiologically-acceptable compound according to claim 73.

91. A pharmaceutical composition having pharmacologically-active principle and therapeutically-acceptable substantially-inert carrier and/or excipient, and wherein the active principle comprises from 1 to 95 percent by weight of the composition and from 0.5 to 1000 milligrams of at least one pharmacologically-active and physiologically acceptable compound according to claim 1.

92. A pharmaceutically-acceptable salt according to claim 1.

93. The compound according to claim 28 which is N-(p-chloro)benzoyl-4-cyclooctylaminobutyric acid.

94. An acid according to claim 1.

95. An ester according to claim 1.

96. An acylaminoalkanoic acid according to claim 1 wherein

R is an optionally-substituted member selected from the group consisting of bihenylyl, cyclohexylphenyl, phenylcyclohexyl, indenyl, indanyl, naphthyl, dihydronaphthyl and tetrahydronaphthyl; or a radical of the formula

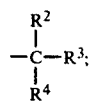

$R^1$ is alkyl with from 1 to 7 carbon atoms, alkenyl or alkynyl with from 2 to 7 carbon atoms, cycloalkyl or cycloalkenyl with from 3 to 10 carbon atoms, or optionally-substituted phenyl;

$R^2$ is —H, alkyl with from 1 to 7 carbon atoms, alkenyl with from 2 to 7 carbon atoms or alkynyl with from 2 to 7 carbon atoms;

$R^3$ is —H, alkyl with from 1 to 7 carbon atoms, cycloalkyl with from 3 to 10 carbon atoms, optionally-substituted phenyl or, together with $R^4$, alkylene with from 2 to 8 carbon atoms;

$R^4$ is alkyl with from 1 to 7 carbon atoms, cycloalkyl with from 3 to 10 carbon atoms, optionally-substituted phenyl, optionally-substituted phenalkyl with from 1 to 4 carbon atoms in the alkyl chain or, together with $R^3$, alkylene with from 2 to 8 carbon atoms; $R^4$ has at least 3 carbon atoms when $R^4$ is alkyl, $R^2$ is —H or methyl, $R^3$ is —H and $R^1$ is alkyl or optionally-substituted phenyl; or $R^2$, $R^3$ and $R^4$, together with the carbon atom to which each is bound, are adamantyl; and n is 3, 4 or 5;

a salt of such acylaminoalkanoic acid with an inorganic or organic base or an ester of such acid with an alkanol with from 1 to 7 carbon atoms in the alkyl radical or an optionally-substituted phenalkanol with from 1 to 4 carbon atoms in the alkyl chain;

each "optionally-substituted" meaning:
unsubstituted or substituted with at most 3 substituents which are independently selected from the group consisting of halo, alkyl with from 1 to 7 carbon atoms, hydroxy, alkoxy with from 1 to 7 carbon atoms, alkylmercapto with from 1 to 7 carbon atoms, alkyl, alkenyl or alkynyl carbonyloxy with from 1 to 7 carbon atoms in the alkyl or 2 to 7 carbon atoms in the alkenyl or alkynyl radical, amino, monosubstituted amino, disubstituted amino, nitro and trifluoromethyl;

any substituent of monosubstituted amino or of disubstituted amino being independently selected from the group consisting of alkyl with from 1 to 4 carbon atoms and alkanoyl with from 2 to 5 carbon atoms;

and any substituent of optionally-substituted phenalkyl being a nuclear substituent.

97. An acylaminoalkanoic acid according to claim 1 wherein n is 5.

98. An acylaminoalkanoic acid according to claim 1 wherein n is 4.

99. An acylaminoalkanoic acid according to claim 1 wherein n is 3.

100. An acylaminoalkanoic acid according to claim 99 wherein $R^4$ has from 1 to 5 carbon atoms when it is alkyl.

* * * * *

UNITED STATES PATENT AND TRADEMARK OFFICE
CERTIFICATE OF CORRECTION

PATENT NO. : 4,243,678

DATED : January 6, 1981

INVENTOR(S) : Walter KRASTINAT

It is certified that error appears in the above-identified patent and that said Letters Patent are hereby corrected as shown below:

On the title page, left column, first line below "Foreign Application Priority Data", "78865" should read --78805--. Column 2, line 20, "is" should read --R is--. Claim 96, line 4 (column 77, line 37), "bihenylyl" should read --biphenyl-yl--.

Signed and Sealed this

Seventh Day of April 1981

[SEAL]

Attest:

RENE D. TEGTMEYER

*Attesting Officer*   *Acting Commissioner of Patents and Trademarks*